United States Patent
Viti et al.

(10) Patent No.: US 12,071,623 B2
(45) Date of Patent: Aug. 27, 2024

(54) IL-34 ANTISENSE AGENTS AND METHODS OF USING SAME

(71) Applicant: Nogra Pharma Limited, Dublin (IE)

(72) Inventors: Francesca Viti, Salorino (CH); Marie McNulty, Dublin (IE); Salvatore Bellinvia, Mendrisio (CH)

(73) Assignee: Nogra Pharma Limited, Dublin (IE)

(*) Notice: Subject to any disclaimer, the term of this patent is extended or adjusted under 35 U.S.C. 154(b) by 0 days.

(21) Appl. No.: 18/246,845

(22) PCT Filed: May 17, 2022

(86) PCT No.: PCT/EP2022/063300
§ 371 (c)(1),
(2) Date: Mar. 27, 2023

(87) PCT Pub. No.: WO2022/243299
PCT Pub. Date: Nov. 24, 2022

(65) Prior Publication Data
US 2024/0093197 A1 Mar. 21, 2024

Related U.S. Application Data

(60) Provisional application No. 63/201,887, filed on May 17, 2021.

(51) Int. Cl.
| | |
|---|---|
| *C07H 21/02* | (2006.01) |
| *C07H 21/04* | (2006.01) |
| *C12N 15/113* | (2010.01) |

(52) U.S. Cl.
CPC ...... *C12N 15/1136* (2013.01); *C12N 2310/14* (2013.01); *C12N 2310/321* (2013.01); *C12N 2310/3341* (2013.01)

(58) Field of Classification Search
CPC .................. C12N 15/113; C12N 2310/11
See application file for complete search history.

(56) References Cited

U.S. PATENT DOCUMENTS

| | | | |
|---|---|---|---|
| 7,618,814 | B2 | 11/2009 | Bentwich |
| 2013/0028889 | A1 | 1/2013 | Hnik et al. |
| 2014/0273232 | A1 | 9/2014 | Zhang et al. |
| 2017/0204407 | A1 | 7/2017 | Gilbert et al. |
| 2018/0113139 | A1 | 4/2018 | Bellinvia et al. |
| 2018/0338992 | A1 | 11/2018 | McNulty et al. |
| 2023/0002770 | A1 | 1/2023 | Viti et al. |

FOREIGN PATENT DOCUMENTS

| | | |
|---|---|---|
| JP | 2014520873 A | 8/2014 |
| KR | 20150104275 A | 9/2015 |
| WO | WO-2009090639 A2 | 7/2009 |
| WO | WO-2010054826 A1 | 5/2010 |
| WO | WO-2010062399 A2 | 6/2010 |
| WO | WO-2010149960 A1 | 12/2010 |
| WO | WO-2013011021 A1 | 1/2013 |
| WO | WO-2013119716 A1 | 8/2013 |
| WO | WO-2014036357 A1 | 3/2014 |
| WO | WO-2015028454 A2 | 3/2015 |
| WO | WO-2016016262 A1 | 2/2016 |
| WO | WO-2016057800 A1 | 4/2016 |
| WO | WO-2017089555 A1 | 6/2017 |
| WO | WO-2019023551 A1 | 1/2019 |
| WO | WO-2021094616 A1 | 5/2021 |

OTHER PUBLICATIONS

Elbashir et al. (The EMBO Journal, vol. 20, No. 23, pp. 6877-6888, 2001).*
Adler, J., et al., Magnetization transfer helps detect intestinal fibrosis in an animal model of Crohn disease, Radiology, 259(1): 127-135 (2011).
Bertrand, et al., Comparison of antisense oligonucleotides and siRNAs in cell culture and in vivo, Biochem Biophys Res Commun, 296(4): 1000-1004 (2002).
Dhuri, K., et al., Antisense Oligonucleotides: An Emerging Area in Drug Discovery and Development, J Clin Med, 9(6): 2004 (2020).
Dinallo, V., et al., Neutrophil Extracellular Traps Sustain Inflammatory Signals in Ulcerative Colitis, J Crohns Colitis, 13(6): 772-784 (2019).
Franzè, E., et al., Interleukin-34 sustains pro-tumorigenic signals in colon cancer tissue, Oncotarget, 9(3): 3432-3445 (2017).
Franzè et al., Interleukin-34 sustains inflammatory pathways in the gut, Clin Sci 129(3):271-80 (2015).
Franzé, et al., A Functional Role for IL-34 in Sustaining Inflammatory Pathways in IBD, Abstract P.06.5, Abstracts of the 20th National Congress of Digestive Diseases, Mar. 19-22, 2014, Digestive and Liver Disease, 46, Supplement 2:S72 (2014).
Ge, Y., et al., Immunomodulation of Interleukin-34 and its Potential Significance as a Disease Biomarker and Therapeutic Target, Int J Biol Sci, 15(9): 1835-1845 (2019).
Grünweller, A., et al., Locked nucleic acid oligonucleotides: the next generation of antisense agents?, BioDrugs, 21(4): 235-243 (2007).
Jepsen, J.S., et al., LNA-antisense rivals siRNA for gene silencing, Curr Opin Drug Discov Devel, 7(2): 188-194 (2004).
Johannes, L., et al., Current Challenges in Delivery and Cytosolic Translocation of Therapeutic RNAs, Nucleic Acid Ther, 28(3): 178-193 (2018).
Khvorova, A., et al., The chemical evolution of oligonucleotide therapies of clinical utility, Nat Biotechnol, 35(3): 238-248 (2017).
Maccioni, F., et al., Value of T2-weighted magnetic resonance imaging in the assessment of wall inflammation and fibrosis in Crohn's disease, Abdom Imaging, 37(6): 944-957 (2012).
Masteller, E.L., et al., Targeting IL-34 in chronic inflammation, Drug Discov Today, 19(8):1212-1216 (2014).

(Continued)

*Primary Examiner* — Amy Rose Hudson

(57) ABSTRACT

Disclosed herein polynucleotides complementary to IL-34, including IL-34 antisense oligonucleotides and IL-34 NAs, and methods for treating inflammatory diseases, such as an inflammatory bowel disease, and/or fibrosis, associated with elevated activity or expression of IL-34. Also disclosed are pharmaceutical compositions containing a polynucleotide complementary to IL-34, for example, an IL-34 antisense oligonucleotide or an IL-34 siRNA, useful for treating inflammatory diseases and/or fibrosis and manufacture of medicaments containing a disclosed polynucleotide to be used in treating inflammatory diseases and/or fibrosis.

11 Claims, 3 Drawing Sheets

Specification includes a Sequence Listing.

(56) References Cited

OTHER PUBLICATIONS

Nakamichi, Y., et al., IL-34 and CSF-1: similarities and differences, J Bone Miner Metab, 31(5):486-495 (2013).

Nakamichi, Y., et al., Spleen serves as a reservoir of osteoclast precursors through vitamin D-induced IL-34 expression in osteopetrotic op/op mice, Proc Natl Acad Sci U S A, 109(25):10006-10011 (2012).

Nylund, K., et al., Quantitative contrast-enhanced ultrasound comparison between inflammatory and fibrotic lesions in patients with Crohn's disease, Ultrasound Med Biol, 39(7): 1197-1206 (2013).

Pazahr, S., et al., Magnetization transfer for the assessment of bowel fibrosis in patients with Crohn's disease: initial experience, MAGMA, 26(3): 291-301 (2013).

PCT/EP2015/067306 International Search Report and Written Opinion mailed Dec. 11, 2015.

PCT/EP2016/078833 International Search Report and Written Opinion mailed Apr. 19, 2017.

PCT/EP2020/082281 International Search Report and Written Opinion mailed Apr. 6, 2021.

PCT/EP2022/063300 International Search Report and Written Opinion mailed Sep. 23, 2022.

Quaia, E., et al., The value of small bowel wall contrast enhancement after sulfur hexafluoride-filled microbubble injection to differentiate inflammatory from fibrotic strictures in patients with Crohn's disease, Ultrasound Med Biol, 38(8): 1324-1332 (2012).

Rettig, G.R., et al., Progress Toward In Vivo Use of siRNAs-II, Mol Ther, 20(3): 483-512 (2012).

Stidham, R.W., et al., Ultrasound elasticity imaging for detecting intestinal fibrosis and inflammation in rats and humans with Crohn's disease, Gastroenterology, 141(3): 819-826 (2011).

Vickers, et al., Efficient reduction of target RNAs by small interfering RNA and RNase H-dependent antisense agents, J Biol Chem, 278(9): 7108-7118 (2003).

Wang, Y., et al., Interleukin-34, a cytokine crucial for the differentiation and maintenance of tissue resident macrophages and Langerhans cells, Eur J Immunol, 44(6):1575-1581 (2014).

Written Opinion of the International Searching Authority for International Application No. PCT/EP2015/067306, mailed Dec. 11, 2015 (8 pages).

Written Opinion of the International Searching Authority for PCT/EP2016/078833, mailed Apr. 19, 2017 (10 pages).

Yoshino, T., et al., IL-34 Antibody Ameliorates Experimental Colitis by Alternating IL-12p40 Expression in Macrophages, American Gastroenterological Association Abstract 22, Gastroenterology, 148(4): S-8 (2015).

Yu, G., et al., Activation of the interleukin-34 inflammatory pathway in response to influenza A virus infection, Am J Med Sci, 349(2): 145-150 (2015).

Zwicker, S., et al., Interleukin 34: a new modulator of human and experimental inflammatory bowel disease, Clin Sci (Lond), 129(3):281-290 (2015).

U.S. Appl. No. 15/778,688, filed May 24, 2018, Abandoned.

U.S. Appl. No. 17/755,943, filed May 12, 2022, Pending.

Li, M., et al., MicroRNA-31 Negatively Regulates Interleukin-34 Expression In Vitro, J Mol Cell Immunol, 48(6): 597-607 (2019).

Yu, R.Z., et al., Clinical pharmacokinetics of second generation antisense oligonucleotides, Expert Opin Drug Metab Toxicol, 9(2): 169-182 (2013).

* cited by examiner

SEQUENCE LISTING

<160> NUMBER OF SEQ ID NOS: 52

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctcaccaaga cccacag                                                    17

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggctttgggc cgcaccagct                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctttgggccg caccagcttc                                                 20

<210> SEQ ID NO 4
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 4
tgggccgcac cagcttcagg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccatgaccc ggaagcagtt                                                 20

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtttcatgt actgaag                                                    17

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctttgggccg caccagcttc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccatgaccc ggaagcagtt                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctttgggccg caccagcttc                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 10
ctttgggccg caccagcttc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctttgggccg caccagcttc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctttgggccg caccagcttc                                              20

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggccgcacca gcttc                                                   15

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctttgggccg caccag                                                  16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgacccggaa gcagtt                                                  16

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctttgggccg caccagcttc        20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tccatgaccc ggaagcagtt        20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctttgggccg caccagcttc        20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tccatgaccc ggaagcagtt        20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctttgggccg caccagcttc        20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tccatgaccc ggaagcagtt        20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 22
ctttgggccg caccagcttc                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tccatgaccc ggaagcagtt                                                  20

<210> SEQ ID NO 24
<211> LENGTH: 1793
<212> TYPE: DNA
<213> ORGANISM: Homo sapiens

<400> SEQUENCE: 24
catcagacgg gaagcctgga ctgtgggttg ggggcagcct cagcctctcc aacctggcac      60
ccactgcccg tggcccttag gcacctgctt ggggtcctgg agccccttaa ggccaccagc     120
aaatcctagg agaccgagtc ttggcacgtg aacagagcca gatttcacac tgagcagctg     180
cagtcggaga aatcagagaa agcgtcaccc agccccagat tccgaggggc ctgccaggga     240
ctctctcctc ctgctccttg gaaaggaaga ccccgaaaga cccccaagcc accggctcag     300
acctgcttct gggctgccat gggacttgcg gccaccgccc ccggctgtc ctccacgctg      360 ccgggcagat aagggcagct gctgcccttg gggcacctgc tcactcccgc agcccagcca     420
ctcctccagg gccagccctt ccctgactga gtgaccacct ctgctgcccc gaggccatgt     480
aggccgtgct taggcctctg tggacacact gctggggacg gcgcctgagc tctcaggggg     540
acgaggaaca ccaccatgcc ccggggcttc acctggctgc gctatcttgg gatcttcctt     600
ggcgtggcct tggggaatga gcctttggag atgtggccct tgacgcagaa tgaggagtgc     660
actgtcacgg gttttctgcg ggacaagctg cagtacagga gccgacttca gtacatgaaa     720
cactacttcc ccatcaacta caagatcagt gtgccttacg agggggtgtt cagaatcgcc     780
aacgtcacca gctgaggggc ccaggtgagc gagcgggagc tgcggtatct gtgggtcttg     840
gtgagcctca gtgccactga gtcggtgcag gacgtgctgc tcgagggcca cccatcctgg     900
aagtacctgc aggaggtgga gacgctgctg ctgaatgtcc agcagggcct cacggatgtg     960
gaggtcagcc caaggtgga atccgtgttg tccctcttga atgccccagg gccaaacctg    1020
aagctggtgc ggcccaaagc cctgctggac aactgcttcc gggtcatgga gctgctgtac    1080
tgctcctgct gtaaacaaag ctccgtccta aactggcagg actgtgaggt gccaagtcct    1140
cagtcttgca gcccagagcc ctcattgcag tatgcggcca cccagctgta ccctccgccc    1200
ccgtggtccc ccagctcccc gcctcactcc acgggctcgg tgaggccggt cagggcacag    1260
ggcgagggcc tcttgccctg agcaccctgg atggtgactg cggataggggg cagccagacc    1320 agctcccaca ggagttcaac tgggtctgag acttcaaggg gtggtggtgg gagcccccct    1380
tgggagagga cccctgggaa gggtgttttt cctttgaggg ggattctgtg ccacagcagg    1440
gctcagcttc ctgccttcca tagctgtcat ggcctcacct ggagcggagg ggacctgggg    1500
acctgaaggt ggatggggac acagctcctg gcttctcctg gtgctgccct cactgtcccc    1560
ccgcctaaag ggggtactga gcctcctgtg gcccgcagca gtgagggcac agctgtgggt    1620
```

```
tgcaggggag acagccagca cggcgtggcc attctatgac cccccagcct ggcagactgg      1680
ggagctgggg gcagagggcg gtgccaagtg ccacatcttg ccatagtgga tgctcttcca      1740
gtttcttttt tctattaaac accccacttc ctttggaaaa aaaaaaaaa aaa              1793

<210> SEQ ID NO 25
<211> LENGTH: 1779
<212> TYPE: DNA
<213> ORGANISM: Homo sapiens

<400> SEQUENCE: 25
ctcgaagctc ggcgtctgtg atggtctacg gggctttcga ggtgatcagg cagcgtcagt        60
cttcagccgc taagccgaga aggagtcagt cagagagcct tgggccagag ttccaggggc       120
tctgggagtg gctgccagag ccagatttca cactgagcag ctgcagtcgg agaaatcaga       180
gaaagcgtca cccagcccca gattccgagg ggcctgccag ggactctctc ctcctgctcc       240
ttggaaagga agaccccgaa agaccccaa gccaccggct cagacctgct tctgggctgc        300
catgggactt gcggccaccg ccccccggct gtcctccacg ctgccgggca gataagggca       360
gctgctgccc ttggggcacc tgctcactcc cgcagcccag ccactcctcc agggccagcc       420
cttccctgac tgagtgacca cctctgctgc cccgaggcca tgtaggccgt gcttaggcct       480
ctgtggacac actgctgggg acggcgcctg agctctcagg gggacgagga acaccaccat       540
gccccggggc ttcacctggc tgcgctatct tgggatcttc cttggcgtgg ccttggggaa       600
tgagcctttg agatgtggc ccttgacgca gaatgaggag tgcactgtca cgggttttct        660
gcgggacaag ctgcagtaca ggagccgact tcagtacatg aaacactact tccccatcaa       720
ctacaagatc agtgtgcctt acgaggggt gttcagaatc gccaacgtca ccaggctgca       780
gagggcccag gtgagcgagc gggagctgcg gtatctgtgg gtcttggtga gcctcagtgc       840
cactgagtcg gtgcaggacg tgctgctcga gggccaccca tcctggaagt acctgcagga       900
ggtggagacg ctgctgctga atgtccagca gggcctcacg gatgtggagg tcagccccaa       960
ggtggaatcc gtgttgtccc tcttgaatgc cccagggcca aacctgaagc tggtgcggcc      1020
caaagccctg ctggacaact gcttccgggt catggagctg ctgtactgct cctgctgtaa      1080
acaaagctcc gtcctaaact ggcaggactg tgaggtgcca agtcctcagt cttgcagccc      1140
agagccctca ttgcagtatg cggccaccca gctgtaccct ccgccccgt ggtcccccag       1200 ctccccgcct cactccacgg gctcggtgag gccggtcagg gcacagggcg agggcctctt      1260
gccctgagca ccctggatgg tgactgcgga taggggcagc cagaccagct cccacaggag      1320
ttcaactggg tctgagactt caagggtgtg gtgtgggagc ccccttggg agaggacccc       1380 tgggaagggt gtttttcctt tgagggggat tctgtgccac agcagggctc agcttcctgc      1440
cttccatagc tgtcatggcc tcacctggag cggagggggac ctggggacct gaaggtggat     1500
ggggacacag ctcctggctt ctcctggtgc tgccctcact gtcccccgc ctaaagggg        1560 tactgagcct cctgtggccc gcagcagtga gggcacagct gtgggttgca ggggagacag      1620
ccagcacggc gtggccattc tatgaccccc cagcctggca gactggggag ctggggcag       1680 agggcggtgc caagtgccac atcttgccat agtggatgct cttccagttt cttttttcta      1740
ttaaacaccc cacttccttt ggaaaaaaaa aaaaaaaa                              1779

<210> SEQ ID NO 26
<211> LENGTH: 1796
<212> TYPE: DNA
<213> ORGANISM: Homo sapiens
```

<400> SEQUENCE: 26

```
catcagacgg gaagcctgga ctgtgggttg ggggcagcct cagcctctcc aacctggcac      60
ccactgcccg tggcccttag gcacctgctt ggggtcctgg agccccttaa ggccaccagc     120
aaatcctagg agaccgagtc ttggcacgtg aacagagcca gatttcacac tgagcagctg     180
cagtcggaga aatcagagaa agcgtcaccc agccccagat tccgaggggc ctgccaggga     240
ctctctcctc ctgctccttg gaaaggaaga ccccgaaaga cccccaagcc accggctcag     300
acctgcttct gggctgccat gggacttgcg gccaccgccc ccggctgtc ctccacgctg      360
ccgggcagat aagggcagct gctgcccttg ggcacctgc tcactcccgc agcccagcca      420
ctcctccagg gccagccctt cctgactga gtgaccacct tgctgcccc gaggccatgt       480
aggccgtgct taggcctctg tggacacact gctggggacg gcgcctgagc tctcaggggg     540
acgaggaaca ccaccatgcc ccggggcttc acctggctgc gctatcttgg gatcttcctt     600
ggcgtggcct tggggaatga gcctttggag atgtggccct tgacgcagaa tgaggagtgc     660
actgtcacgg gttttctgcg ggacaagctg cagtacagga gccgacttca gtacatgaaa     720
cactacttcc ccatcaacta caagatcagt gtgccttacg agggggtgtt cagaatcgcc     780
aacgtcacca ggctgcagag ggcccaggtg agcgagcggg agctgcggta tctgtgggtc     840
ttggtgagcc tcagtgccac tgagtcggtc caggacgtgc tgctcgaggg ccacccatcc     900
tggaagtacc tgcaggaggt ggagacgctg ctgctgaatg tccagcaggg cctcacggat     960
gtggaggtca gccccaaggt ggaatccgtg ttgtccctct tgaatgcccc agggccaaac    1020
ctgaagctgg tgcggcccaa agccctgctg gacaactgct tccgggtcat ggagctgctg    1080
tactgctcct gctgtaaaca aagctccgtc ctaaactggc aggactgtga ggtgccaagt    1140
cctcagtctt gcagcccaga gccctcattg cagtatgcgg ccacccagct gtaccctccg    1200
cccccgtggt cccccagctc cccgcctcac tccacgggct cggtgaggcc ggtcagggca    1260
cagggcgagg gcctcttgcc ctgagcaccc tggatggtga ctgcggatag gggcagccag    1320
accagctccc acaggagttc aactgggtct gagacttcaa ggggtggtgg tgggagcccc    1380
ccttgggaga ggacccctgg gaagggtgtt tttcctttga gggggattct gtgccacagc    1440
agggctcagc ttcctgcctt ccatagctgt catggcctca cctggagcgg aggggacctg    1500
gggacctgaa ggtggatggg gacacagctc ctggcttctc ctggtgctgc cctcactgtc    1560
cccccgccta aaggggtac tgagcctcct gtggcccgca gcagtgaggg cacagctgtg     1620
ggttgcaggg gagacagcca gcacggcgtg gccattctat gacccccag cctggcagac     1680
tggggagctg ggggcagagg gcggtgccaa gtgccacatc ttgccatagt ggatgctctt    1740
ccagtttctt ttttctatta aacaccccac ttcctttgga aaaaaaaaa aaaaaa         1796
```

<210> SEQ ID NO 27
<211> LENGTH: 1747
<212> TYPE: DNA
<213> ORGANISM: Mus musculus

<400> SEQUENCE: 27

```
tctagaaaca aatctgagct gctgtagcgt gtgtcccccg ccctccgaga agactgtagg      60
ctgaacacac aacagcctgt cccacacagc atttactgcc acagccccca aggcacctgc     120
tccaggcctt gagctgctca aagcttccgg cgacggcgac tgtagaagcc cacatcctgg     180
caggtgagca gagctagact tcacgctgag cagctgcagc cgaagaaacc agagaaagcg     240
```

```
ccacccagcc ccagattcca agaggcctgc ctgctgggga ctcccttctc ttcttcctcc    300
tcctcctctt cctcctcctg agaccctcaa agtcactgtc tcacaccagt tcctgagctg    360
caatgggact ggcagccact gccccctggc tgtcctccgc cctgccaagc agatagggcg    420
gtagctaccc caggagtatc tgcccoctct cagcctggac cagcccttto tggacttggt    480
ggccaccttt gctgacctaa ggccatgtag tccctggctc aggcctctgg acacacttct    540
ggggacagtg cctctgctct caggggggcac ccagtgcacc accatgccct ggggactcgc    600
ctggctatac tgtcttggga tcctacttga cgtggctttg ggaaacgaga atttggagat    660
atggactctg acccaagata aggagtgtga ccttacaggc taccttcggg gcaagctgca    720
gtacaagaac cggcttcagt acatgaaaca ttacttcccc atcaactaca ggattgctgt    780
gccttatgag ggggtactca gagtggccaa catcacaagg ctgcagaagg ctcacgtgag    840
tgagcgagag cttcggtacc tgtgggtctt ggtgagtctc aatgccactg agtctgtgat    900
ggatgtactt ctcgagggcc acccgtcctg gaagtatcta caggaggttc agacattgct    960
ggagaacgta cagcggagcc tcatggatgt ggagattggc cctcacgtgg aagctgtgtt   1020
atctcttctg agtactccag gcctaagcct gaagctggtg cggcccaaag ccttgctgga   1080
caactgcttc cgggtcatgg aactgctgta ctgttcttgc tgtaaacaaa gccccatctt   1140
aaaatggcag gactgcgagc tgcccaggct ccatccccac agtccggggt ccttgatgca   1200
atgtacagct acaaatgtgt acccttgtc tcggcagacc cccacctccc tgcccggatc   1260
cccaagctca agccatggct cgttgccctg agcaatctat gtattgaccc tgggtcgggc   1320
cactggatgc atttcagaaa ctggcctgga tctgagacct tcctggatgg tgggtaggta   1380
gcccctttag gaaaggcctt cagggaaagg cctcctgcct tctcttccac acccaggctt   1440
cctgccttct ggtggtatca cggagcctca ggggagggat gtggagggga gggctggttg   1500
ctatccctta cagccaccct tgcttgtggc ccggtccgaa atctgcaaac actgttgccc   1560
cacaggcggg tggccaagaa cgacggggtg cctcctagga tcccaggact tactggggct   1620
tttcagttgt gctgactgtg gggtgctggg ccgaggacca accaaatgcc gtatcttgcc   1680
atgacgatgc tcttctggtt cctttttcta ttaaatggcc atttatttgg tttggcttgc   1740
aaaaaaa                                                              1747

<210> SEQ ID NO 28
<211> LENGTH: 1865
<212> TYPE: DNA
<213> ORGANISM: Mus musculus

<400> SEQUENCE: 28
tctagaaaca aatctgagct gctgtagcgt gtgtcccccg ccctccgaga agactgtagg     60
ctgaacacac aacagcctgt cccacacagc atttactgcc acagccccca aggcacctgc    120
tccaggcctt gagctgctca aagcttccgg cgacggcgac tgtagaagcc cacatcctgg    180
caggtgagca gagctagact tcacgctgag cagctgcagc cgaagaaacc agagaaagcg    240
ccacccagcc ccagattcca agaggcctgc ctgctgggga ctcccttctc ttcttcctcc    300
tcctcctctt cctcctcctg agaccctcaa agtcactgtc tcacaccagt tcctgagctg    360
caatgggact ggcagccact gccccctggc tgtcctccgc cctgccaagc agatagggcg    420
gtagctaccc caggagtatc tgcccoctct cagcctggac cagcccttto tggacttggt    480
ggccaccttt gctgacctaa ggccatgtag tccctggctc aggcctctgg acacacttct    540
ggggacagtg cctctgctct caggggggcac ccagtgcacc accatgccct ggggactcgc    600
```

-continued

```
ctggctatac tgtcttggga tcctacttga cgtggctttg ggaaacgaga atttggagat    660
atggactctg acccaagata aggagtgtga ccttacaggc taccttcggg gcaagctgca    720
gtacaagaac cggcttcagt acatgaaaca ttacttcccc atcaactaca ggattgctgt    780
gccttatgag ggggtactca gagtggccaa catcacaagg ctgcagaagg ctcacgtgag    840
tgagcgagag cttcggtacc tgtgggtctt ggtgagtctc aatgccactg agtctgtgat    900
ggatgtactt ctcgagggcc acccgtcctg gaagtatcta caggaggttc agacattgct    960
ggagaacgta cagcggagcc tcatggccgt tggtgtacac ctgccgggac acgtacttgt   1020
gaccctgctc agccagctgc ctggcctccc cagcccatgg gccagatcat ttgacaccag   1080
ctgggagctt ctgatgatga aggatgtgg agattggccc tcacgtggaa gctgtgttat    1140
ctcttctgag tactccaggc ctaagcctga agctggtgcg gcccaaagcc ttgctggaca   1200
actgcttccg ggtcatggaa ctgctgtact gttcttgctg taaacaaagc cccatcttaa   1260
aatggcagga ctgcgagctg cccaggctcc atccccacag tccggggtcc ttgatgcaat   1320
gtacagctac aaatgtgtac cctttgtctc ggcagacccc cacctccctg cccggatccc   1380
caagctcaag ccatggctcg ttgccctgag caatctatgt attgaccctg gtcgggcca    1440 ctggatgcat ttcagaaact ggcctggatc tgagaccttc ctggatggtg ggtaggtagc   1500
ccctttagga aaggccttca gggaaaggcc tcctgccttc tcttccacac ccaggcttcc   1560
tgccttctgg tggtatcacg gagcctcagg ggagggatgt ggaggggagg gctggttgct   1620
atcccttaca gccacctctg cttgtggccc ggtccgaaat ctgcaaacac tgttgcccca   1680
caggcgggtg gccaagaacg acggggtgcc tcctaggatc ccaggactta ctggggcttt   1740
tcagttgtgc tgactgtggg gtgctgggcc gaggaccaac caaatgccgt atcttgccat   1800
gacgatgctc ttctggttcc tttttctatt aaatggccat ttatttggtt tggcttgcaa   1860
aaaaa                                                               1865
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acaggagccg acttcagtac                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
accaagaccc acagataccg                                                20

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagatgaccc agatcatgtt tgagacc                                    27

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agccagtcca gacgcaggat                                            20

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aacacgtcta tacgc                                                 15

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctgctcaact ttctgcgaag                                            20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctcatctcca cataggtgtc                                            20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggacacagag gtttcagtgg                                            20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggacacagag gtttcagtgg                                               20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggagaatgtt gtgcagtttg c                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggagaatgtt gtgcagtttg c                                             21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctttgggccg caccagcttc                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctttgggccg caccagcttc                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tccatgaccc ggaagcagtt                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
tccatgaccc ggaagcagtt                                                20
```

<210> SEQ ID NO 44
<211> LENGTH: 1775
<212> TYPE: DNA
<213> ORGANISM: Homo sapiens

<400> SEQUENCE: 44

```
agacgggaag cctggactgt gggttggggg cagcctcagc ctctccaacc tggcacccac    60
tgcccgtggc ccttaggcac ctgcttgggg tcctggagcc ccttaaggcc accagcaaat   120
cctaggagac cgagtcttgg cacgtgaaca gagccagatt tcacactgag cagctgcagt   180
cggagaaatc agagaaagcg tcacccagcc ccagattccg aggggcctgc cagggactct   240
ctcctcctgc tccttggaaa ggaagacccc gaaagacccc caagccaccg gctcagacct   300
gcttctgggc tgccatggga cttgcggcca ccgcccccg gctgtcctcc acgctgccgg    360
gcagataagg gcagctgctg cccttggggc acctgctcac tcccgcagcc cagccactcc   420
tccagggcca gcccttccct gactgagtga ccacctctgc tgccccgagg ccatgtaggc   480
cgtgcttagg cctctgtgga cacactgctg gggacggcgc ctgagctctc aggggacga    540
ggaacaccac catgccccgg ggcttcacct ggctgcgcta tcttgggatc ttccttggcg    600
tggccttggg gaatgagcct ttggagatgt ggcccttgac gcagaatgag gagtgcactg    660
tcacgggttt tctgcgggac aagctgcagt acaggagccg acttcagtac atgaaacact    720
acttccccat caactacaag atcagtgtgc cttacgaggg ggtgttcaga atcgccaacg    780
tcaccaggct gcagagggcc caggtgagcg agcgggagct gcggtatctg tgggtcttgg    840
tgagcctcag tgccactgag tcggtgcagg acgtgctgct cgagggccac ccatcctgga    900
agtacctgca ggaggtggag acgctgctgc tgaatgtcca gcagggcctc acggatgtgg    960
aggtcagccc caaggtggaa tccgtgttgt ccctcttgaa tgccccaggg ccaaacctga   1020
agctggtgcg gcccaaagcc ctgctggaca actgcttccg ggtcatggag ctgctgtact   1080
gctcctgctg taaacaaagc tccgtcctaa actggcagga ctgtgaggtg ccaagtcctc   1140
agtcttgcag cccagagccc tcattgcagt atgcggccac ccagctgtac cctccgcccc   1200
cgtggtcccc cagctccccg cctcactcca cgggctcggt gaggccggtc agggcacagg   1260
gcgagggcct cttgccctga gcaccctgga tggtgactgc ggatagggc agccagacca    1320
gctcccacag gagttcaact gggtctgaga cttcaagggg tggtggtggg agccccctt    1380
gggagaggac ccctgggaag ggtgttttc ctttgagggg gattctgtgc cacagcaggg   1440
ctcagcttcc tgccttccat agctgtcatg gcctcacctg gagcggaggg gacctgggga   1500
cctgaaggtg gatggggaca cagctcctgg cttctcctgg tgctgccctc actgtccccc   1560
cgcctaaagg gggtactgag cctcctgtgg cccgcagcag tgagggcaca gctgtgggtt   1620
gcaggggaga cagccagcac ggcgtggcca ttctatgacc ccccagcctg gcagactggg   1680
gagctggggg cagagggcgg tgccaagtgc cacatcttgc catagtggat gctcttccag   1740
tttcttttt ctattaaaca ccccacttcc tttgg                               1775
```

<210> SEQ ID NO 45
<211> LENGTH: 1772
<212> TYPE: DNA
<213> ORGANISM: Homo sapiens

<400> SEQUENCE: 45

| | |
|---|---:|
| agacgggaag cctggactgt gggttggggg cagcctcagc ctctccaacc tggcacccac | 60 |
| tgcccgtggc ccttaggcac ctgcttgggg tcctggagcc ccttaaggcc accagcaaat | 120 |
| cctaggagac cgagtcttgg cacgtgaaca gagccagatt tcacactgag cagctgcagt | 180 |
| cggagaaatc agagaaagcg tcacccagcc ccagattccg aggggcctgc cagggactct | 240 |
| ctcctcctgc tccttggaaa ggaagacccc gaaagacccc caagccaccg gctcagacct | 300 |
| gcttctgggt tgccatggga cttgcggcca ccgcccccg gctgtcctcc acgctgccgg | 360 |
| gcagataagg gcagctgctg cccttggggc acctgctcac tcccgcagcc cagccactcc | 420 |
| tccagggcca gccctttccct gactgagtga ccacctctgc tgccccgagg ccatgtaggc | 480 |
| cgtgcttagg cctctgtgga cacactgctg gggacggcgc ctgagctctc aggggacga | 540 |
| ggaacaccac catgccccgg ggcttcacct ggctgcgcta tcttgggatc ttccttggcg | 600 |
| tggccttggg gaatgagcct ttggagatgt ggcccttgac gcagaatgag gagtgcactg | 660 |
| tcacgggttt tctgcgggac aagctgcagt acaggagccg acttcagtac atgaaacact | 720 |
| acttccccat caactacaag atcagtgtgc cttacgaggg ggtgttcaga atcgccaacg | 780 |
| tcaccaggct gagggcccag gtgagcgagc gggagctgcg gtatctgtgg gtcttggtga | 840 |
| gcctcagtgc cactgagtcg gtgcaggacg tgctgctcga gggccaccca tcctggaagt | 900 |
| acctgcagga ggtggagacg ctgctgctga atgtccagca gggcctcacg gatgtggagg | 960 |
| tcagccccaa ggtggaatcc gtgttgtccc tcttgaatgc cccagggcca aacctgaagc | 1020 |
| tggtgcggcc caaagccctg ctggacaact gcttccgggt catggagctg ctgtactgct | 1080 |
| cctgctgtaa acaaagctcc gtcctaaact ggcaggactg tgaggtgcca agtcctcagt | 1140 |
| cttgcagccc agagccctca ttgcagtatg cggccaccca gctgtaccct ccgccccgt | 1200 |
| ggtccccag ctccccgcct cactccacg gctcggtgag gccggtcagg gcacagggcg | 1260 |
| agggcctctt gccctgagca ccctggatgg tgactgcgga taggggcagc cagaccagct | 1320 |
| cccacaggag ttcaactggg tctgagactt caagggtgg tggtgggagc cccccttggg | 1380 |
| agaggacccc tgggaagggt gttttttcctt tgaggggggat tctgtgccac agcagggctc | 1440 |
| agcttcctgc cttccatagc tgtcatggcc tcacctggag cggaggggac ctggggacct | 1500 |
| gaaggtggat ggggacacag ctcctggctt ctcctggtgc tgccctcact gtcccccgc | 1560 |
| ctaaaggggg tactgagcct cctgtggccc gcagcagtga gggcacagct gtgggttgca | 1620 |
| ggggagacag ccagcacggc gtggccattc tatgaccccc cagcctggca gactggggag | 1680 |
| ctggggcag agggcggtgc caagtgccac atcttgccat agtggatgct cttccagttt | 1740 |
| ctttttctcta ttaaacaccc cacttccttt gg | 1772 |

<210> SEQ ID NO 46
<211> LENGTH: 1696
<212> TYPE: DNA
<213> ORGANISM: Homo sapiens

<400> SEQUENCE: 46

| | |
|---|---:|
| atgatcagag atgtctgcat gaggaacaga ggctgctttg tggattgggg agctcccat | 60 |
| tagcggaggc agagccagat tcacactga gcagctgcag tcggagaaat cagagaaagc | 120 |
| gtcacccagc cccagattcc gaggggcctg ccagggactc tctcctcctg ctccttggaa | 180 |
| aggaagaccc cgaaagaccc ccaagccacc ggctcagacc tgcttctggg ctgccatggg | 240 |
| acttgcggcc accgcccccc ggctgtcctc cacgctgccg ggcagataag ggcagctgct | 300 |
| gcccttgggg cacctgctca ctcccgcagc ccagccactc ctccagggcc agcccttccc | 360 |

```
tgactgagtg accacctctg ctgccccgag gccatgtagg ccgtgcttag gcctctgtgg      420
acacactgct ggggacggcg cctgagctct caggggacg aggaacacca ccatgccccg      480
gggcttcacc tggctgcgct atcttgggat cttccttggc gtggccttgg ggaatgagcc      540
tttggagatg tggcccttga cgcagaatga ggagtgcact gtcacgggtt ttctgcggga      600
caagctgcag tacaggagcc gacttcagta catgaaacac tacttcccca tcaactacaa      660
gatcagtgtg ccttacgagg gggtgttcag aatcgccaac gtcaccaggc tgcagagggc      720
ccaggtgagc gagcgggagc tgcggtatct gtgggtcttg gtgagcctca gtgccactga      780
gtcggtgcag gacgtgctgc tcgagggcca cccatcctgg aagtacctgc aggaggtgga      840
gacgctgctg ctgaatgtcc agcagggcct cacggatgtg gaggtcagcc caaggtgga      900 atccgtgttg tccctcttga atgccccagg gccaaacctg aagctggtgc ggcccaaagc      960
cctgctggac aactgcttcc gggtcatgga gctgctgtac tgctcctgct gtaaacaaag     1020
ctccgtccta aactggcagg actgtgaggt gccaagtcct cagtcttgca gcccagagcc     1080
ctcattgcag tatgcggcca cccagctgta ccctccgccc ccgtggtccc ccagctcccc     1140
gcctcactcc acgggctcgg tgaggccggt cagggcacag ggcgagggcc tcttgccctg     1200
agcaccctgg atggtgactg cggatagggg cagccagacc agctcccaca ggagttcaac     1260
tgggtctgag acttcaaggg gtggtggtgg gagccccct tgggagagga ccctgggaa     1320 gggtgttttt cctttgaggg ggattctgtg ccacagcagg gctcagcttc ctgccttcca     1380
tagctgtcat ggcctcacct ggagcggagg ggacctgggg acctgaaggt ggatggggac     1440
acagctcctg gcttctcctg gtgctgccct cactgtcccc ccgcctaaag ggggtactga     1500
gcctcctgtg gcccgcagca gtgagggcac agctgtgggt tgcaggggag acagccagca     1560
cggcgtggcc attctatgac ccccccagcct ggcagactgg ggagctgggg gcagagggcg     1620
gtgccaagtg ccacatcttg ccatagtgga tgctcttcca gtttcttttt tctattaaac     1680
accccacttc ctttgg                                                     1696

<210> SEQ ID NO 47
<211> LENGTH: 1693
<212> TYPE: DNA
<213> ORGANISM: Homo sapiens

<400> SEQUENCE: 47
atgatcagag atgtctgcat gaggaacaga ggctgctttg tggattgggg agctccccat       60
tagcggaggc agagccagat ttcacactga gcagctgcag tcggagaaat cagagaaagc      120
gtcacccagc cccagattcc gaggggcctg ccagggactc tctcctcctg ctccttggaa      180
aggaagaccc cgaaagaccc ccaagccacc ggctcagacc tgcttctggg ctgccatggg      240
acttgcggcc accgcccccc ggctgtcctc cacgctgccg ggcagataag ggcagctgct      300
gcccttgggg cacctgctca ctcccgcagc ccagccactc ctccagggcc agcccttccc      360
tgactgagtg accacctctg ctgccccgag gccatgtagg ccgtgcttag gcctctgtgg      420
acacactgct ggggacggcg cctgagctct caggggacg aggaacacca ccatgccccg      480
gggcttcacc tggctgcgct atcttgggat cttccttggc gtggccttgg ggaatgagcc      540
tttggagatg tggcccttga cgcagaatga ggagtgcact gtcacgggtt ttctgcggga      600
caagctgcag tacaggagcc gacttcagta catgaaacac tacttcccca tcaactacaa      660
gatcagtgtg ccttacgagg gggtgttcag aatcgccaac gtcaccaggc tgagggccca      720
```

```
ggtgagcgag cgggagctgc ggtatctgtg ggtcttggtg agcctcagtg ccactgagtc    780
ggtgcaggac gtgctgctcg agggccaccc atcctggaag tacctgcagg aggtggagac    840
gctgctgctg aatgtccagc agggcctcac ggatgtggag gtcagcccca aggtggaatc    900
cgtgttgtcc ctcttgaatg ccccagggc  aaacctgaag ctggtgcggc ccaaagccct    960
gctggacaac tgcttccggg tcatggagct gctgtactgc tcctgctgta aacaaagctc   1020
cgtcctaaac tggcaggact gtgaggtgcc aagtcctcag tcttgcagcc agagccctc    1080 attgcagtat gcggccaccc agctgtaccc tccgccccg  tggtccccca gctcccgcc    1140 tcactccacg ggctcggtga ggccggtcag ggcacagggc gagggcctct tgccctgagc   1200
accctggatg gtgactgcgg ataggggcag ccagaccagc tcccacagga gttcaactgg   1260
gtctgagact tcaaggggtg gtggtgggag ccccccttgg gagaggaccc ctgggaaggg   1320 tgttttcct  ttgaggggga ttctgtgcca cagcagggct cagcttcctg ccttccatag   1380
ctgtcatggc ctcacctgga gcggagggga cctggggacc tgaaggtgga tgggacaca   1440 gctcctggct tctcctggtg ctgccctcac tgtccccccg cctaaagggg gtactgagcc   1500
tcctgtggcc cgcagcagtg agggcacagc tgtgggttgc aggggagaca gccagcacgg   1560
cgtggccatt ctatgacccc ccagcctggc agactgggga gctgggggca gagggcggtg   1620
ccaagtgcca catcttgcca tagtggatgc tcttccagtt ctttttttct attaaacacc   1680
ccacttcctt tgg                                                      1693

<210> SEQ ID NO 48
<211> LENGTH: 1762
<212> TYPE: DNA
<213> ORGANISM: Homo sapiens

<400> SEQUENCE: 48
ctcgaagctc ggcgtctgtg atggtctacg gggctttcga ggtgatcagg cagcgtcagt     60
cttcagccgc taagccgaga aggagtcagt cagagagcct tgggccagag ttccaggggc    120
tctgggagtg gctgccagag ccagatttca cactgagcag ctgcagtcgg agaaatcaga    180
gaaagcgtca cccagcccca gattccgagg ggcctgccag ggactctctc ctcctgctcc    240
ttggaaagga agaccccgaa agaccccccaa gccaccggct cagacctgct tctgggctgc    300
catgggactt gcgccaccg  ccccccggct gtcctccacg ctgccgggca gataagggca    360
gctgctgccc ttggggcacc tgctcactcc cgcagcccag ccactcctcc agggccagcc    420
cttccctgac tgagtgacca cctctgctgc cccgaggcca tgtaggccgt gcttaggcct    480
ctgtggacac actgctgggg acggcgcctg agctctcagg gggacgagga acaccaccat    540 gccccgggc  ttcacctggc tgcgctatct tgggatcttc cttggcgtgg ccttggggaa    600
tgagcctttg gagatgtggc ccttgacgca gaatgaggag tgcactgtca cgggttttct    660 gcggacaag  ctgcagtaca ggagccgact tcagtacatg aaacactact tccccatcaa    720
ctacaagatc agtgtgcctt acgaggggt  gttcagaatc gccaacgtca ccaggctgca    780
gagggcccag gtgagcgagc gggagctgcg gtatctgtgg gtcttggtga gcctcagtgc    840
cactgagtcg gtgcaggacg tgctgctcga gggccaccca tcctggaagt acctgcagga    900
ggtggagacg ctgctgctga atgtccagca gggcctcacg gatgtggagg tcagccccaa    960
ggtggaatcc gtgttgtccc tcttgaatgc cccagggcca aacctgaagc tggtgcggcc   1020
caaagccctg ctggacaact gcttccgggt catggagctg ctgtactgct cctgctgtaa   1080
acaaagctcc gtcctaaact ggcaggactg tgaggtgcca agtcctcagt cttgcagccc   1140
```

| | |
|---|---|
| agagccctca ttgcagtatg cggccaccca gctgtaccct ccgccccgt ggtccccag | 1200 |
| ctccccgcct cactccacgg gctcggtgag gccggtcagg gcacagggcg agggcctctt | 1260 |
| gccctgagca ccctggatgg tgactgcgga tagggcagc cagaccagct cccacaggag | 1320 |
| ttcaactggg tctgagactt caaggggtgg tggtgggagc cccccttggg agaggacccc | 1380 |
| tgggaagggt gtttttcctt tgagggggat tctgtgccac agcagggctc agcttcctgc | 1440 |
| cttccatagc tgtcatggcc tcacctggag cggaggggac ctgggacct gaaggtggat | 1500 |
| ggggacacag ctcctggctt ctcctggtgc tgccctcact gtcccccgc ctaaagggg | 1560 |
| tactgagcct cctgtggccc gcagcagtga gggcacagct gtgggttgca ggggagacag | 1620 |
| ccagcacggc gtggccattc tatgaccccc cagcctggca gactggggag ctggggcag | 1680 |
| agggcggtgc caagtgccac atcttgccat agtggatgct cttccagttt ctttttttcta | 1740 |
| ttaaacaccc cacttccttt gg | 1762 |

<210> SEQ ID NO 49
<211> LENGTH: 1613
<212> TYPE: DNA
<213> ORGANISM: Homo sapiens

<400> SEQUENCE: 49

| | |
|---|---|
| acactgagca gctgcagtcg gagaaatcag agaaagcgtc acccagcccc agattccgag | 60 |
| gggcctgcca gggactctct cctcctgctc cttggaaagg aagaccccga agaccccca | 120 |
| agccaccggc tcagacctgc ttctgggctg ccatgggact tgcggccacc gccccccggc | 180 |
| tgtcctccac gctgccgggc agataagggc agctgctgcc cttggggcac ctgctcactc | 240 |
| ccgcagccca gccactcctc cagggccagc ccttccctga ctgagtgacc acctctgctg | 300 |
| ccccgaggcc atgtaggccg tgcttaggcc tctgtggaca cactgctggg gacggcgcct | 360 |
| gagctctcag ggggacgagg aacaccacca tgccccgggg cttcacctgg ctgcgctatc | 420 |
| ttgggatctt cctttggcgtg gccttgggga atgagccttt ggagatgtgg cccttgacgc | 480 |
| agaatgagga gtgcactgtc acgggttttc tgcgggacaa gctgcagtac aggagccgac | 540 |
| ttcagtacat gaaacactac ttccccatca actacaagat cagtgtgcct tacgaggggg | 600 |
| tgttcagaat cgccaacgtc accaggctga gagggcccca ggtgagcgag cgggagctgc | 660 |
| ggtatctgtg ggtcttggtg agcctcagtg ccactgagtc ggtgcaggac gtgctgctcg | 720 |
| agggccaccc atcctggaag tacctgcagg aggtggagac gctgctgctg aatgtccagc | 780 |
| agggcctcac ggatgtggag gtcagccca aggtggaatc cgtgttgtcc ctcttgaatg | 840 |
| ccccagggcc aaacctgaag ctggtgcggc ccaaagccct gctggacaac tgcttccggg | 900 |
| tcatggagct gctgtactgc tcctgctgta aacaaagctc cgtcctaaac tggcaggact | 960 |
| gtgaggtgcc aagtcctcag tcttgcagcc cagagccctc attgcagtat gcggccaccc | 1020 |
| agctgtaccc tccgccccg tggtccccca gctcccgcc tcactccacg ggctcggtga | 1080 |
| ggccggtcag ggcacagggc gagggcctct tgccctgagc accctggatg gtgactgcgg | 1140 |
| ataggggcag ccagaccagc tcccacagga gttcaactgg gtctgagact tcaaggggtg | 1200 |
| gtggtgggag ccccccttgg gagaggaccc ctggaaggg tgttttcct ttgaggggga | 1260 |
| ttctgtgcca cagcagggct cagcttcctg ccttccatag ctgtcatggc ctcacctgga | 1320 |
| gcggagggga cctggggacc tgaaggtgga tggggacaca gctcctggct ctcctggtg | 1380 |
| ctgccctcac tgtcccccg cctaaagggg gtactgagcc tcctgtggcc cgcagcagtg | 1440 |

| | | | | |
|---|---|---|---|---|
| agggcacagc | tgtgggttgc | aggggagaca | gccagcacgg | cgtggccatt | ctatgacccc | 1500 |
| ccagcctggc | agactgggga | gctgggggca | gagggcggtg | ccaagtgcca | catcttgcca | 1560 |
| tagtggatgc | tcttccagtt | tcttttttct | attaaacacc | ccacttcctt | tgg | 1613 |

<210> SEQ ID NO 50
<211> LENGTH: 1610
<212> TYPE: DNA
<213> ORGANISM: Homo sapiens

<400> SEQUENCE: 50

| | | | | | |
|---|---|---|---|---|---|
| acactgagca | gctgcagtcg | gagaaatcag | agaaagcgtc | acccagcccc | agattccgag | 60 |
| gggcctgcca | gggactctct | cctcctgctc | cttggaaagg | aagaccccga | agaccccca | 120 |
| agccaccggc | tcagacctgc | ttctgggctg | ccatgggact | tgcggccacc | gccccccggc | 180 |
| tgtcctccac | gctgccgggc | agataagggc | agctgctgcc | cttggggcac | ctgctcactc | 240 |
| ccgcagccca | gccactcctc | cagggccagc | ccttccctga | ctgagtgacc | acctctgctg | 300 |
| ccccgaggcc | atgtaggccg | tgcttaggcc | tctgtggaca | cactgctggg | gacggcgcct | 360 |
| gagctctcag | ggggacgagg | aacaccacca | tgccccgggg | cttcacctgg | ctgcgctatc | 420 |
| ttgggatctt | ccttggcgtg | gccttgggga | atgagccttt | ggagatgtgg | cccttgacgc | 480 |
| agaatgagga | gtgcactgtc | acgggttttc | tgcgggacaa | gctgcagtac | aggagccgac | 540 |
| ttcagtacat | gaaacactac | ttccccatca | actacaagat | cagtgtgcct | tacgagggg | 600 |
| tgttcagaat | cgccaacgtc | accaggctga | gggcccaggt | gagcgagcgg | gagctgcggt | 660 |
| atctgtgggt | cttggtgagc | ctcagtgcca | ctgagtcggt | gcaggacgtg | ctgctcgagg | 720 |
| gccacccatc | ctggaagtac | ctgcaggagg | tggagacgct | gctgctgaat | gtccagcagg | 780 |
| gcctcacgga | tgtggaggtc | agccccaagg | tggaatccgt | gttgtccctc | ttgaatgccc | 840 |
| cagggccaaa | cctgaagctg | gtgcggccca | agccctgct | ggacaactgc | ttccgggtca | 900 |
| tggagctgct | gtactgctcc | tgctgtaaac | aaagctccgt | cctaaactgg | caggactgtg | 960 |
| aggtgccaag | tcctcagtct | tgcagcccag | agccctcatt | gcagtatgcg | ccacccagc | 1020 |
| tgtaccctcc | gccccgtgg | tcccccagct | ccccgcctca | ctccacgggc | tcggtgaggc | 1080 |
| cggtcagggc | acagggcgag | ggcctcttgc | cctgagcacc | ctggatggtg | actgcggata | 1140 |
| ggggcagcca | gaccagctcc | cacaggagtt | caactgggtc | tgagacttca | aggggtggtg | 1200 |
| gtgggagccc | ccttgggag | aggacccctg | ggaagggtgt | ttttcctttg | aggggattc | 1260 |
| tgtgccacag | cagggctcag | cttcctgcct | tccatagctg | tcatggcctc | acctggagcg | 1320 |
| gaggggacct | ggggacctga | aggtggatgg | ggacacagct | cctggcttct | cctggtgctg | 1380 |
| ccctcactgt | cccccgcct | aaaggggta | ctgagcctcc | tgtggcccgc | agcagtgagg | 1440 |
| gcacagctgt | gggttgcagg | ggagacagcc | agcacggcgt | ggccattcta | tgaccccca | 1500 |
| gcctggcaga | ctggggagct | gggggcagag | ggcggtgcca | agtgccacat | cttgccatag | 1560 |
| tggatgctct | tccagtttct | tttttctatt | aaacacccca | cttcctttgg | | 1610 |

<210> SEQ ID NO 51
<211> LENGTH: 1515
<212> TYPE: DNA
<213> ORGANISM: Homo sapiens

<400> SEQUENCE: 51

| | | | | | |
|---|---|---|---|---|---|
| ggaaggcgct | acagacccgc | tggcatagtt | agctgggagg | gacactaaga | tcagatagag | 60 |
| caggaaggaa | agtggtgtgg | ggcgtgggtg | actgaagagt | cattttatca | agttgaaacc | 120 |

```
agaatccagg atgattcgat ctcctgaatg ccgggctgga aaacccagca acgagctttg    180
aaaacatatc acccggacac caggggcaga ggctgttctg ggcgggaggt tgtgcctgcc    240
ccacggagcg acagaagcgg ggagaccaga cgtcgaccct gaggcgtgcc tcctgggggg    300
ctccagtggc cggcatggga tcttgggatc ttccttggcg tggccttggg gaatgagcct    360
ttggagatgt ggcccttgac gcagaatgag gagtgcactg tcacgggttt tctgcgggac    420
aagctgcagt acaggagccg acttcagtac atgaaacact acttccccat caactacaag    480
atcagtgtgc cttacgaggg ggtgttcaga atcgccaacg tcaccaggct gcagagggcc    540
caggtgagcg agcgggagct gcggtatctg tgggtcttgg tgagcctcag tgccactgag    600
tcggtgcagg acgtgctgct cgagggccac ccatcctgga agtacctgca ggaggtggag    660
acgctgctgc tgaatgtcca gcagggcctc acggatgtgg aggtcagccc caaggtggaa    720
tccgtgttgt ccctcttgaa tgccccaggg ccaaacctga agctggtgcg gcccaaagcc    780
ctgctggaca actgcttccg ggtcatggag ctgctgtact gctcctgctg taaacaaagc    840
tccgtcctaa actggcagga ctgtgaggtg ccaagtcctc agtcttgcag cccagagccc    900
tcattgcagt atgcggccac ccagctgtac cctccgcccc cgtggtcccc cagctccccg    960
cctcactcca cgggctcggt gaggccggtc agggcacagg gcgagggcct cttgccctga   1020
gcaccctgga tggtgactgc ggatagggggc agccagacca gctcccacag gagttcaact   1080
gggtctgaga cttcaagggg tggtggtggg agccccctt gggagaggac ccctgggaag   1140 ggtgttttc ctttgagggg gattctgtgc cacagcaggg ctcagcttcc tgccttccat   1200
agctgtcatg gcctcacctg gagcggaggg gacctgggga cctgaaggtg gatgggaca   1260 cagctcctgg cttctcctgg tgctgccctc actgtccccc cgcctaaagg gggtactgag   1320
cctcctgtgg cccgcagcag tgagggcaca gctgtgggtt gcaggggaga cagccagcac   1380
ggcgtggcca ttctatgacc ccccagcctg gcagactggg gagctggggg cagagggcgg   1440
tgccaagtgc cacatcttgc catagtggat gctcttccag tttcttttt ctattaaaca   1500 cccccacttcc tttgg                                                   1515

<210> SEQ ID NO 52
<211> LENGTH: 1512
<212> TYPE: DNA
<213> ORGANISM: Homo sapiens

<400> SEQUENCE: 52
ggaaggcgct acagacccgc tggcatagtt agctgggagg gacactaaga tcagatagag     60
caggaaggaa agtggtgtgg ggcgtgggtg actgaagagt cattttatca agttgaaacc    120
agaatccagg atgattcgat ctcctgaatg ccgggctgga aaacccagca acgagctttg    180
aaaacatatc acccggacac caggggcaga ggctgttctg ggcgggaggt tgtgcctgcc    240
ccacggagcg acagaagcgg ggagaccaga cgtcgaccct gaggcgtgcc tcctgggggg    300
ctccagtggc cggcatggga tcttgggatc ttccttggcg tggccttggg gaatgagcct    360
ttggagatgt ggcccttgac gcagaatgag gagtgcactg tcacgggttt tctgcgggac    420
aagctgcagt acaggagccg acttcagtac atgaaacact acttccccat caactacaag    480
atcagtgtgc cttacgaggg ggtgttcaga atcgccaacg tcaccaggct gagggcccag    540
gtgagcgagc gggagctgcg gtatctgtgg gtcttggtga gcctcagtgc cactgagtcg    600
gtgcaggacg tgctgctcga gggccaccca tcctggaagt acctgcagga ggtggagacg    660
```

| | | | | | |
|---|---|---|---|---|---|
| ctgctgctga | atgtccagca | gggcctcacg | gatgtggagg | tcagcccaa | ggtggaatcc | 720
| gtgttgtccc | tcttgaatgc | cccagggcca | aacctgaagc | tggtgcggcc | caaagccctg | 780
| ctggacaact | gcttccgggt | catggagctg | ctgtactgct | cctgctgtaa | acaaagctcc | 840
| gtcctaaact | ggcaggactg | tgaggtgcca | agtcctcagt | cttgcagccc | agagccctca | 900
| ttgcagtatg | cggccaccca | gctgtaccct | ccgcccccgt | ggtccccag | ctccccgcct | 960
| cactccacgg | gctcggtgag | gccggtcagg | gcacagggcg | agggcctctt | gccctgagca | 1020
| ccctggatgg | tgactgcgga | tagggcagc | cagaccagct | cccacaggag | ttcaactggg | 1080
| tctgagactt | caagggtgg | tggtgggagc | ccccttggg | agaggacccc | tgggaagggt | 1140
| gttttccctt | tgagggggat | tctgtgccac | agcagggctc | agcttcctgc | cttccatagc | 1200
| tgtcatggcc | tcacctggag | cggaggggac | ctgggacct | gaaggtggat | ggggacacag | 1260
| ctcctggctt | ctcctggtgc | tgccctcact | gtccccccgc | ctaaaggggg | tactgagcct | 1320
| cctgtggccc | gcagcagtga | gggcacagct | gtgggttgca | ggggagacag | ccagcacggc | 1380
| gtggccattc | tatgacccc | cagcctggca | gactggggag | ctggggcag | agggcggtgc | 1440
| caagtgccac | atcttgccat | agtggatgct | cttccagttt | cttttttcta | ttaaacaccc | 1500
| cacttcctt | gg | | | | | 1512

IL-34 ANTISENSE AGENTS AND METHODS OF USING SAME

CROSS REFERENCE TO RELATED APPLICATIONS

This application is the U.S. National Stage entry of International Application No. PCT/EP2022/063300, filed May 17, 2022, which claims the benefit of and priority to U.S. Provisional Patent Application No. 63/201,887, filed May 17, 2021, the disclosure of each are hereby incorporated by reference in their entireties for all purposes.

SEQUENCE LISTING

This instant application contains a Sequence Listing which has been filed electronically in ASCII format and is hereby incorporated by reference in its entirety. Said ASCII copy, created Nov. 17, 2022, is named GIU-068WOUS_SL.txt and is 41,790 bytes in size.

BACKGROUND

Interleukin-34 (IL-34) is a recently discovered cytokine functionally overlapping with macrophage colony stimulating factor (M-CSF, also known as MCSF1 and MCSF-1), a mediator of inflammation and osteoclastogenesis in bone-degenerative diseases such as rheumatoid arthritis. Inflammatory diseases, both acute and chronic, are an important disease category that is still not completely understood.

For example, rheumatoid arthritis (RA) is a chronic autoimmune and inflammatory disorder of the joints and bones suffered by approximately 1.3 million patients in the United States. Among those afflicted with RA, the prevalence of work disability associated with RA was around 35% in the United States, with an overall health care cost of more than $19.3 billion. Osteoarthritis (OA) is a chronic inflammatory disease of the joints, an involves mechanical wear and destruction of the smooth cartilage joint surface that caps the bones in the joints. OA is the most common form of arthritis and affects 32.5 million adults in the United States, with an overall health care cost of more than $136 billion. No medical cure currently exists for RA or OA.

Inflammatory bowel disease is a chronic inflammatory disorder of the gastrointestinal tract suffered by approximately 1.4 million patients in the United States. It is one of the five most prevalent gastrointestinal disease burdens in the United States, with an overall health care cost of more than $1.7 billion. Each year in the United States, inflammatory bowel disease accounts for more than 700,000 physician visits, 100,000 hospitalizations, and disability in 119,000 patients. No medical cure currently exists, so disease management requires a lifetime of care.

The two most common forms of inflammatory bowel disease are Crohn's disease and ulcerative colitis. Although Crohn's disease can affect the entire gastrointestinal tract, it primarily affects the ileum (the distal or lower portion of the small intestine) and the large intestine. Ulcerative colitis primarily affects the colon and the rectum. The etiology of inflammatory bowel disease is not completely understood, although both environmental and genetic factors are believed to play a role in the disease. Environmental components may include alterations in flora of the gut which are affected by exposure to ingested foods and medications.

Inflammatory bowel disease is associated with abdominal pain, vomiting, diarrhea, rectal bleeding, severe cramps, muscle spasms, weight loss, malnutrition, fever, and anemia. Patients with inflammatory bowel disease may also suffer from skin lesions, joint pain, eye inflammation, and liver disorders, and children suffering from ulcerative colitis may suffer from growth defects. Although rarely fatal, these symptoms decrease quality of life for patients.

Thus, there is a pressing need to develop reliable methods of treating inflammatory disorders such as rheumatoid arthritis, osteoarthritis, or inflammatory bowel disease. There is a further need to identify methods of treatment that provide effective and permanent relief from symptoms across a broad spectrum of patients and which are not associated with negative side effects or cycles of inflammation and remission.

SUMMARY

The present application provides compositions of polynucleotides complementary to IL-34, or a portion thereof, and methods of using the compositions.

Disclosed herein, in certain embodiments, are polynucleotides, comprising a nucleotide sequence according to: (a) 5'-CTTTGGGCCGCACCAGCTTC-3' (SEQ ID NO: 3) or (b) 5'-TCCATGACCCGGAAGCAGTT-3' (SEQ ID NO: 5), wherein at least one cytidine of the nucleotide sequence is chemically modified, and at least one nucleoside is a 2'-O-(2-methoxyethyl) (2'-MOE) nucleoside; or a pharmaceutically acceptable salt thereof. In some embodiments, no more than 10 nucleosides of the polynucleotide are chemically modified. In some embodiments, the polynucleotide comprises six 2'-MOE nucleosides. In some embodiments, the polynucleotide comprises eight 2'-MOE nucleosides. In some embodiments, the polynucleotide comprises a nucleotide sequence is selected from the group consisting of: (a) 5'-CxTxTxTxGGGCXGCACCAGCxTxTxCx-3' (SEQ ID NO: 40), wherein Cx is 2'-O-(2-methoxyethyl)cytidine, Tx is 2'-O-(2-methoxyethyl)thymidine, and X is 5-methylcytidine; (b) 5'-CxTxTxTGGGCXGCACCAGCTxTxCx-3' (SEQ ID NO: 41), wherein Cx is 2'-O-(2-methoxyethyl)cytidine, Tx is 2'-O-(2-methoxyethyl)thymidine, and X is 5-methylcytidine; (c) 5'-TxexCxAxTGACCXG-GAAGCAxGxTxTx-3' (SEQ ID NO: 42), wherein Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; and (d) 5'-TxCxCxATGACCXGGAAGCAGxTxTx-3' (SEQ ID NO: 43), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine; or a pharmaceutically acceptable salt thereof. In some embodiments, the polynucleotide is complementary to IL-34. In some embodiments, the polynucleotide is an IL-34 antisense oligonucleotide. In some embodiments, the polynucleotide is an IL-34 siRNA. In some embodiments, at least one internucleoside linkage of the polynucleotide is selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, and an aminoalkylphosphoramidate linkage, a thiophosphoramidate linkage, thionoalkylphosphonate linkage, a thionoalkylphosphotriester linkage, a thiophosphate linkage, a selenophosphate linkage, and a boranophosphate linkage. In some embodiments, at least one internucleoside linkage of the polynucleotide is a phosphorothioate linkage. In some embodiments, all internucleoside linkages of the polynucleotide are phosphorothioate linkages. In some embodiments, the polynucleotide is 20, 21, 22, 23, 24, 25, 26, 27, 28, 29, or 30 nucleotides in length. In some embodiments, the polynucleotide is 20 nucleotides in length or 20-25, 20-30, 20-35, 25-30, 25-35, or 30-35 nucleotides in length. In some embodiments, the polynucleotide is no more than 20, 25, or 30 nucleotides in length. In some embodiments, the polynucleotide is from 20 to 25 nucleotides in length. In some embodiments, the polynucleotide is 20 nucleotides in length.

Disclosed herein, in certain embodiments, are pharmaceutical compositions, comprising (a) a polynucleotide disclosed herein, or a pharmaceutically acceptable salt thereof, and (b) a pharmaceutically acceptable excipient. In some embodiments, the pharmaceutical composition is suitable for topical, parenteral, oral, pulmonary, intratracheal, intranasal, transdermal, or intraduodenal administration.

Disclosed herein, in certain embodiments, are methods of treating an inflammatory disease in a patient in need thereof, the method comprising administering to the patient in need thereof an effective amount of a polynucleotide disclosed herein, or a pharmaceutically acceptable salt thereof, or a pharmaceutical composition disclosed herein. In some embodiments, the inflammatory disease is associated with altered IL-34 expression. In some embodiments, the method inhibits inflammatory cytokine production in cells of the patient. In some embodiments, the method reduces or inhibits an IL-34 mediated inflammatory response in cells of the patient. In some embodiments, the method reduces or inhibits IL-34-mediated macrophage colony-stimulating factor receptor (M-CSFR-1) signaling in cells of the patient. In some embodiments, the cell is an intestinal cell. In some embodiments, the cell is an intestinal stromal cell. In some embodiments, the cell forms part of an intestinal fibrostricture. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are methods of preventing or treating a cancer associated with altered IL-34 expression in a patient in need thereof, the method comprising administering to the patient in need thereof an effective amount of a polynucleotide disclosed herein, or a pharmaceutically acceptable salt thereof, or a pharmaceutical composition disclosed herein. In some embodiments, the cancer has elevated IL-34 expression. In some embodiments, the cancer is colon cancer.

Disclosed herein, in certain embodiments, are methods of reducing or eliminating a fibrotic stricture in a patient suffering from an inflammatory disease, the method comprising administering an effective amount of a polynucleotide disclosed herein, or a pharmaceutically acceptable salt thereof, or a pharmaceutical composition disclosed herein. In some embodiments, the fibrotic stricture is located in the intestine. In some embodiments, the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, Sjogren's syndrome (SS), obesity, chronic inflammation, pulmonary sarcoidosis, skin lesions, a CNS inflammatory disease, and an autoimmune disease. In some embodiments, the inflammatory disease is an inflammatory bowel disease. In some embodiments, the inflammatory bowel disease is selected from the group consisting of Crohn's disease, gastroduodenal Crohn's disease, Crohn's (granulomatous) colitis, inflammatory Crohn's disease, fibrostricturing Crohn's disease, ulcerative colitis, collagenous colitis, lymphocytic colitis, ischaemic colitis, diversion colitis, Behcet's disease, microscopic colitis, ulcerative proctitis, proctosigmoiditis, jejunoileitis, left-sided colitis, pancolitis, ileocolitis, ileitis, and indeterminate colitis. In some embodiments, the inflammatory bowel disease is inflammatory Crohn's disease. In some embodiments, the inflammatory bowel disease is fibrostricturing Crohn's disease. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are methods for preventing or treating fibrosis, the method comprising administering to a patient in need thereof a therapeutically effective amount of a polynucleotide disclosed herein, or a pharmaceutically acceptable salt thereof, or a pharmaceutical composition disclosed herein. In some embodiments, the fibrosis is intestinal fibrosis. In some embodiments, the fibrosis is pulmonary fibrosis. In some embodiments, the fibrosis is synovial fibrosis. In some embodiments, the fibrosis is selected from the group consisting of renal fibrosis, cardiac fibrosis, endomyocardial fibrosis, myelofibrosis, retroperitoneal fibrosis, and nephrogenic systemic fibrosis. In some embodiments, the patient is also suffering from Crohn's disease. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are methods of preventing or treating intestinal fibrosis, the method comprising administering to a patient in need thereof, a pharmaceutically effective amount of a polynucleotide disclosed herein, or a pharmaceutically acceptable salt thereof, or a pharmaceutical composition disclosed herein. In some embodiments, the patient is also suffering from Crohn's disease. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are methods of preventing or treating pulmonary fibrosis, the method comprising administering to a patient in need thereof, a pharmaceutically effective amount of a polynucleotide disclosed herein, or a pharmaceutically acceptable salt thereof, or a pharmaceutical composition disclosed herein. In some embodiments, the patient is also suffering from Crohn's disease. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are methods of preventing or treating synovial fibrosis, the method comprising administering to a patient in need thereof, a pharmaceutically effective amount of a polynucleotide disclosed herein, or a pharmaceutically acceptable salt thereof, or a pharmaceutical composition disclosed herein. In some embodiments, the polynucleotide is administered intraarticularly, rectally, topically, parenterally, orally, pulmonarily, intratracheally, intranasally, transdermally, or intraduodenally. In some embodiments, the polynucleotide is administered orally. In some embodiments, the patient is a human.

Disclosed herein, in certain embodiments, are uses of a polynucleotide disclosed herein, or a pharmaceutically acceptable salt thereof, in the manufacture of a medicament for treating an inflammatory disease. In some embodiments, the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, or Sjogren's syndrome (SS), obesity, chronic inflammation, pulmonary sarcoidosis, skin lesions, a CNS inflammatory disease, and an autoimmune disease. In some embodiments, the inflammatory disease is rheumatoid arthritis or osteoarthritis. In some embodiments, the inflammatory disease is an inflammatory bowel disease. In some embodiments, the inflammatory bowel disease is selected from the group consisting of Crohn's disease, inflammatory Crohn's disease, fibrostricturing Crohn's disease, gastroduodenal Crohn's disease, Crohn's (granulomatous) colitis, ulcerative colitis, collagenous colitis, lymphocytic colitis, ischaemic colitis, diversion colitis, Behcet's disease, microscopic colitis, ulcerative proctitis, proctosigmoiditis, jejunoileitis, left-sided colitis, pancolitis, ileocolitis, ileitis, and indeterminate colitis. In some embodiments, the inflammatory bowel disease is inflammatory Crohn's disease. In some embodiments, the inflammatory bowel disease is fibrostricturing Crohn's disease.

Disclosed herein, in certain embodiments, are polynucleotides disclosed herein, or a pharmaceutically-acceptable salt thereof, for use as a medicament.

Disclosed herein, in certain embodiments, are polynucleotides disclosed herein, or a pharmaceutically-acceptable salt thereof, for use in the treatment of an inflammatory disease. In some embodiments, the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, or Sjogren's syndrome (SS), obesity, chronic inflammation, pulmonary sarcoidosis, skin lesions, a CNS inflammatory disease, and an autoimmune disease. In some embodiments, the inflammatory disease is an inflammatory bowel disease. In some embodiments, the inflammatory bowel disease is selected from the group consisting of Crohn's disease, inflammatory Crohn's disease, fibrostricturing Crohn's disease, gastroduodenal Crohn's disease, Crohn's (granulomatous) colitis, ulcerative colitis, collagenous colitis, lymphocytic colitis, ischaemic colitis, diversion colitis, Behcet's disease, microscopic colitis, ulcerative proctitis, proctosigmoiditis, jejunoileitis, left-sided colitis, pancolitis, ileocolitis, ileitis, and indeterminate colitis. In some embodiments, the inflammatory bowel disease is inflammatory Crohn's disease. In some embodiments, the inflammatory bowel disease is fibrostricturing Crohn's disease.

Disclosed herein, in certain embodiments, are polynucleotides disclosed herein, or a pharmaceutically-acceptable salt thereof, for use in the treatment of fibrosis. In some embodiments, the fibrosis is intestinal fibrosis. In some embodiments, the fibrosis is pulmonary fibrosis. In some embodiments, the fibrosis is synovial fibrosis. In some embodiments, the fibrosis is selected from the group consisting of renal fibrosis, cardiac fibrosis, endomyocardial fibrosis, myelofibrosis, retroperitoneal fibrosis, and nephrogenic systemic fibrosis.

DETAILED DESCRIPTION

Figure 1:
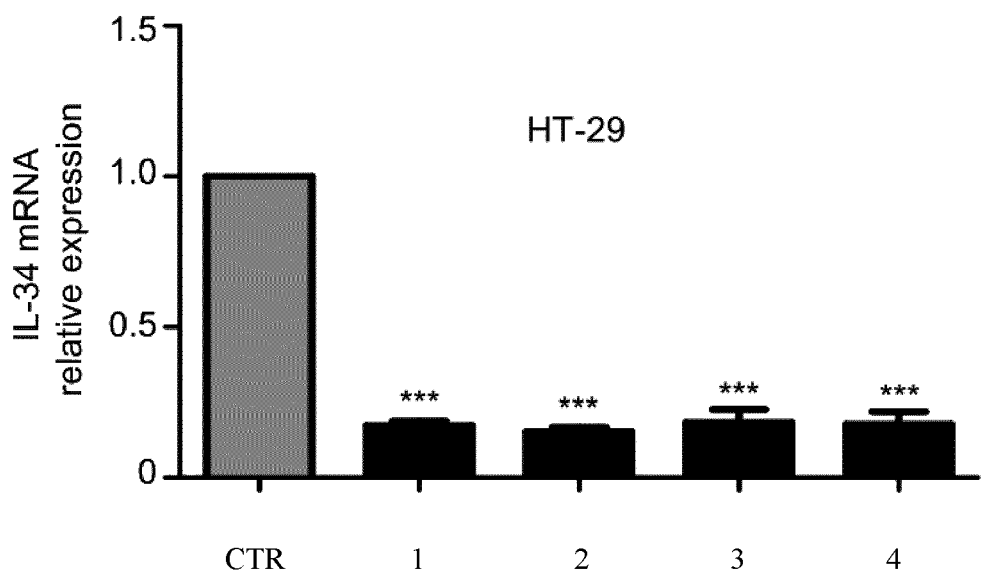
FIG. 1 shows the results of the IL-34 ASOs on the modulation of IL-34 expression in cultured HT-29 cells. IL-34 RNA transcripts were evaluated by real-time PCR. Levels are normalized to β-actin. (CTR=scrambled ASO, 1=SEQ ID NO: 17, 2=SEQ ID NO: 19, 3=SEQ ID NO: 42, 4=SEQ ID NO: 43). Values are mean±SEM of four experiments. Differences among groups were compared using 1-way analysis of variance followed by the Dunnett's post hoc test. IL-34 ASOs vs CTR, ***P<0.001.

Disclosed herein, inter alia, are polynucleotides that are complementary to an IL-34 nucleic acid, or a portion thereof (e.g., IL-34 antisense oligonucleotides) and comprising one or more chemically modified nucleoside, compositions comprising said oligonucleotides, and methods of using the compositions for treating, reducing, or inhibiting a disease or disorder, such as an autoimmune or inflammatory diseases (e.g., rheumatoid arthritis (RA), osteoarthritis (OA), Crohn's disease or ulcerative colitis) or fibrosis.

Definitions

As used herein, "oligonucleotide" or "polynucleotide" are used interchangeably and refers to short DNA or RNA molecules. In some embodiments, oligonucleotides comprise 2'-deoxyribonucleotides (oligodeoxyribonucleotides), which can be modified at the phosphate backbone or at the 2' sugar position. In some embodiments, oligonucleotides of the disclosure have one or more phosphorothioate (PS) backbone modifications, where one or more of the non-bridging oxygen atoms in the phosphate backbone is replaced with a sulfur atom. In some embodiments, a "phosphorothioate oligonucleotide" or "PS oligonucleotide" has at least one internucleoside linkage that is an O,O-linked phosphorothioate linkage (i.e., a phosphorothioate linkage). In some embodiments, a PS oligonucleotide has all internucleoside linkages being O,O-linked phosphorothioate linkages (i.e., a phosphorothioate linkage).

As used herein, "antisense therapeutics" are a class of nucleic acid-based compounds that can be used to inhibit gene expression. Antisense therapeutics may be single- or double-stranded deoxyribonucleic acid (DNA)-based, ribonucleic acid (RNA)-based, mixed DNA and RNA-based, or DNA/RNA chemical analogue compounds. In some embodiments, antisense therapeutics comprise antisense oligonucleotides. In general, antisense therapeutics are designed to include a nucleotide sequence that is complementary or nearly complementary to an mRNA or pre-mRNA sequence transcribed from a given gene in order to promote binding between the antisense therapeutic and the pre-mRNA or mRNA. Without being bound by theory, it is believed that in most instances antisense therapeutics act by binding to an mRNA or pre-mRNA, thereby inhibiting protein translation, altering pre-mRNA splicing into mature mRNA, and/or causing destruction of mRNA. In most instances, the antisense therapeutic nucleotide sequence is complementary to a portion of a targeted gene's or mRNA's sense sequence.

As used herein, "IL-34 antisense therapeutics" are oligonucleotide-based compounds that include an oligonucleotide sequence complementary to an IL-34 gene sense, IL-34 pre-mRNA sense, and/or IL-34 mRNA sense sequence, or a portion thereof. IL-34 antisense therapeutics described herein can also be nucleotide chemical analog-based compounds capable of binding to an IL-34 gene sense, IL-34 pre-mRNA sense, and/or IL-34 mRNA sense sequence, or a portion thereof. In some embodiments, IL-34 antisense therapeutics may include IL-34 antisense oligonucleotides, IL-34 shRNAs, IL-34 siRNAs, IL-34 PNAs, IL-34 LNAs, miRNAs, and IL-34 morpholino oligomers.

As used herein, "antisense oligonucleotides" (ASOs) are short synthetic oligonucleotide-based sequences comprising sequences complementary to a target RNA sequence such as a mRNA that encodes a target protein (e.g., IL-34). Without being bound to a particular theory, antisense oligonucleotide sequences can hybridize to a complementary region in an mRNA molecule thereby producing a double-stranded hybrid that can lead to the activation of ubiquitous catalytic enzymes, such as RNase H, which degrade DNA/RNA hybrid strands thus preventing protein translation. Without being bound by theory, an antisense oligonucleotide provided herein can hybridize to its target sequence as RNA or DNA. Accordingly, in some embodiments, if a DNA sequence is provided as a target, the corresponding RNA sequence (including uracil instead of thymine) is included in an ASO as described herein. In some embodiments, ASOs described herein comprise chemically modified nucleosides.

The number of nucleotides included in antisense oligonucleotides described herein can vary. ASOs are typically between 8 to 50 nucleotides in length, for example, 20 nucleotides in length. In some embodiments, the antisense oligonucleotide is from 15-20, 15-25, 15-30, 15-35, 20-25, 20-30, 20-35, 25-30, 25-35, or 30-35 nucleotides in length. In particular embodiments, the antisense oligonucleotide is from 15-25 nucleotides in length. In particular embodiments, the antisense oligonucleotide is from 20-25 nucleotides in length. In some embodiments, the antisense oligonucleotide is 15, 16, 17, 18, 19, 20, 21, 22, 23, 24, 25, 26, 27, 28, 29, 30, 31, 32, 33, 34, or 35 nucleotides in length. In some embodiments an antisense oligonucleotide described herein includes a maximum number of nucleotides. In some embodiments, an antisense oligonucleotide is no more than 15, 16, 17, 18, 19, 20, 21, 22, 23, 24, 25, 30, or 35 nucleotides in length.

As used herein, "chemically modified nucleoside" means any nucleoside other than adenosine, cytidine, thymidine, guanosine, or uridine. A chemically modified nucleoside may comprise a modified sugar moiety and/or a modified nucleobase. In some embodiments, a chemically modified nucleosides disclosed may be a locked nucleic acid (LNA), e.g., LNA cytidine, LNA thymidine, LNA adenosine, or LNA guanosine. In some embodiments, chemically modified nucleosides comprise 2'-O-methyl ("2'-OMe") ribonucleosides, for example, 2'-O-methylcytidine, 2'-O-methylguanosine, 2'-O-methylthymidine, 2'-O-methyluridine, and/or 2'-O-methyladenosine. In other embodiments, a chemically modified nucleoside comprises a 5-methylpyrimidine, for example, 5-methylcytosine; and/or a 5-methylpurine, for example, 5-methylguanine. In some embodiments, chemically modified nucleosides can include any of the following chemically-modified nucleosides: 5-methyl-2'-O-methylcytidine, 5-methyl-2'-O-methylthymidine, 5-methylcytidine, 5-methyluridine, and/or 5-methyl-2'-deoxycytidine. In some embodiments disclosed herein, chemically modified nucleosides can include a stabilized terminal 5'-phosphate or phosphatase-resistant analogue of 5'-phosphate, e.g., 5'-methyl phosphonate, 5'-methylenephosphonate, a 5'-methylenephosphonate analog, 5'-E-vinyl phosphonate (5'-E-VP), 5'-phosphorothioate, and a 5'-C-methyl analog; a 2'-O-methyl ribonucleoside, e.g., 2'-O-methylcytidine, 2'-O-methylguanosine, 2'-O-methyluridine, 2'-O-methylthymidine, and 2'-O-methyladenosine; a 5-methylpyrimidine, e.g., 5-methylcytosine; a 5-methylpurine, e.g., 5-methylguanine; 5-methyl-2'-O-methylcytidine; 5-methyl-2'-O-methylthymidine; 5-methylcytidine; 5-methyluridine; or 5-methyl 2'-deoxycytidine.

Additionally, in some embodiments, chemically modified nucleosides described herein include 2'-O-(2-methoxyethyl) ("2'-MOE") nucleosides, 2'-deoxy-2'-fluoro nucleosides, 2'-fluoro-β-D-arabinonucleosides, bridged nucleosides, LNA nucleosides, constrained ethyl (cET) nucleosides, tricyclo-DNA (tcDNA) nucleosides, 2'-O,4'-C-ethylene linked nucleic acid (ENA) nucleosides, and/or peptide nucleic acids (PNA).

As used herein, "internucleoside linkage" means the connection between the 3' position of a nucleoside and the 5' position of an adjacent nucleoside. A "modified internucleoside linkage" refers to a connection between the 3' position of a nucleoside and the 5' position of an adjacent nucleoside that is not natural. In some embodiments, a modified internucleoside linkage includes, but is not limited to: a phosphorothioate linkage; a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, an aminoalkylphosphoramidate linkage, a thiophosphoramidate linkage, a thionoalkylphosphonate linkage, a thionoalkylphosphotriester linkage, a thiophosphate linkage, a selenophosphate linkage, or a boranophosphate linkage.

Peptide nucleic acids (PNAs) are short, artificially synthesized polymers with a structure that mimics DNA or RNA. PNAs include a backbone composed of repeating N-(2-aminoethyl)-glycine units linked by peptide bonds.

Locked nucleic acids (LNAs) are oligonucleotide sequences that include one or more modified RNA nucleotides in which the ribose moiety is modified with an extra bridge connecting the 2' oxygen and 4' carbon. LNAs are believed to have higher Tm's than analogous oligonucleotide sequences.

Morpholino oligomers are oligonucleotide compounds that include DNA bases attached to a backbone of methylenemorpholine rings linked through phosphorodiamidate groups. Morpholino oligomers of the present invention can be designed to bind to specific RNA sequences of interest (e.g., IL-34 mRNA or IL-34 pre-mRNA sequences of interest), thereby preventing gene expression.

Small hairpin RNAs (shRNAs) are generally RNA molecules with a hairpin-like structure that can be used to silence gene expression. shRNAs are generally expressed from plasmids encoding the shRNA sequence, and can be expressed from viral vectors to allow lentiviral, adenoviral, or adeno-associated viral expression. Without being bound by theory, it is believed that shRNA inhibits gene expression by taking advantage of RNA interference (RNAi) processes. In brief, the shRNA transcript is processed by Drosha and Dicer, and then loaded onto the RNA-induced silencing complex (RISC), allowing targeting of specific mRNA, and either mRNA degradation or repression of protein translation.

Small interfering RNAs (siRNAs) are double-stranded RNA molecules of approximately 20-25 base pairs in length (but which can also be, for example, 18-30 base pairs in length) that take advantage of RNAi machinery (e.g., Drosha and RISC) to bind and target mRNA for degradation. siRNAs are not dependent upon plasmids or vectors for expression, and can generally be delivered directly to a target cell, for instance, by transfection.

MicroRNAs (miRNAs) are small non-coding RNA molecule containing about 22 nucleotides that function in RNA silencing and post-transcriptional regulation of gene expression. miRNAs include sequences that are complementary to portions of an mRNA sequence. miRNAs are produced from long, single-stranded RNA molecules exhibiting highly specific stem—loop structures. Artificial miRNAs are designed by replacing the mature 21 nucleotide sequence of naturally occurring miRNA sequences with 21 nucleotide sequences from a target, for example, an IL-34 mRNA target.

As used herein, "IL-34 inhibitors" comprise, but are not limited to, nucleotide-based inhibitors of IL-34 (for example, IL-34 small hairpin RNAs (shRNAs), IL-34 microRNAs (miRNAs), IL-34 small interfering RNAs (siRNAs), and IL-34 antisense oligonucleotides, including IL-34 antisense oligonucleotides that include LNA nucleotides, peptide nucleic acids (PNAs), and morpholino oligomers), and compositions that include such compounds. In some embodiments, IL-34 levels (e.g., IL-34 mRNA or protein levels) and/or activity (e.g., biological activity, for example, IL-34 receptor stimulation) can be decreased using IL-34 inhibitors. In some embodiments, IL-34 inhibitors comprise IL-34 antisense oligonucleotides comprising one or more chemically modified nucleoside.

As used herein, "IL-34 antisense oligonucleotide" or "IL-34 ASO" is understood to refer to an oligonucleotide comprising a nucleic acid sequence that is complementary to a nucleic acid sequence in an mRNA molecule transcribed from the IL-34 gene, or a portion thereof. More specifically, such an oligonucleotide can be complementary to the nucleic acid sequence in the coding region of such an mRNA, or a portion thereof. In some embodiments, an IL-34 antisense oligonucleotide possesses the inherent functional property of targeting the IL-34 gene, its RNA or protein products, or another molecular entity whose activity or expression impinges upon the activity or expression of IL-34 or its products either exclusively or with a high degree of specificity. In some embodiments, an IL-34 antisense oligonucleotide can reduce the expression of IL-34 when introduced into a cell (e.g., an immune cell, such as a PBMC, dendritic cell, or B-cell). In some embodiments, an IL-34 antisense oligonucleotide can reduce expression of an mRNA transcribed from the gene. In some embodiments, an IL-34 antisense oligonucleotide can reduce expression of a protein encoded by the gene. In some embodiments, an IL-34 antisense oligonucleotide can reduce secretion of a protein encoded by the gene from the cell into which the IL-34 antisense oligonucleotide was introduced. In some embodiments, an IL-34 antisense oligonucleotide comprises the sequence of SEQ ID NOs: 40-43, or pharmaceutically acceptable salts thereof.

Throughout the description and claims of this specification the word "comprise" and other forms of the word, such as "comprising" and "comprises," means including but not limited to, and is not intended to exclude, for example, other additives, components, integers, or steps.

"Optional" or "optionally" means that the subsequently described event or circumstance can or cannot occur, and that the description includes instances where the event or circumstance occurs and instances where it does not.

As used herein, the term "about" or "approximately," when used in reference to a quantitative value, includes the recited quantitative value itself, unless specifically stated otherwise. As used herein, the term "about" or "approximately" refers to a ±10% variation from the recited quantitative value unless otherwise indicated or inferred from the context.

The terminology used herein is for the purpose of describing particular embodiments only, and is not intended to limit the scope of the present disclosure. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

Unless otherwise defined, all technical and scientific terms used herein have the same meaning as commonly understood by one of ordinary skill in the art to which this disclosure belongs. In the case of conflict, the present specification will control. Although methods and materials similar or equivalent to those described herein can be used in the practice or testing of the present disclosure, suitable methods and materials are described below.

Polynucleotides Complementary to IL-34

Disclosed herein, inter alia, are polynucleotides complementary to IL-34. In some embodiments, the polynucleotide comprises the nucleotide sequence: 5'-CTTTGGGC-CGCACCAGCTTC-3' (SEQ ID NO: 3), or 5'-TC-CATGACCCGGAAGCAGTT-3' (SEQ ID NO: 5); 5'-CTTTGGGCXGCACCAGCTTC-3' (SEQ ID NO: 7); or 5'-TCCATGACCXGGAAGCAGTT-3' (SEQ ID NO: 8), wherein a X is 5-methylcytidine, at least one cytidine of the nucleotide sequence is chemically modified, and at least one nucleoside is a 2'-O-(2-methoxyethyl) (2'-MOE) nucleoside, or a pharmaceutically acceptable salt thereof. In some embodiments, the polynucleotide comprises a nucleotide sequence selected from the group consisting of:

a. 5'-CxTxTxTxGGGCXGCACCAGCxTxTxCx-3' (SEQ ID NO: 40), wherein Cx is 2'-O-(2-methoxyethyl) cytidine, Tx is 2'-O-(2-methoxyethyl)thymidine, and X is 5-methylcytidine;

b. 5'-CxTxTxTGGGCXGCACCAGCTxTxCx-3' (SEQ ID NO: 41), wherein Cx is 2'-O-(2-methoxyethyl) cytidine, Tx is 2'-O-(2-methoxyethyl)thymidine, and X is 5-methylcytidine;

c. 5'-TxCxCxAxTGACCXGGAAGCAxGxTxTx-3' (SEQ ID NO: 42), wherein Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; and d. 5'-TxCxCxATGACCXGGAAGCAGxTxTx-3' (SEQ ID NO: 43), wherein Cx is 2'-O-(2-methoxyethyl) cytidine, Tx is 2'-O-(2-methoxyethyl)thymidine, Gx is 2'-O-(2-methoxyethyl)guanosine, and X is 5-methylcytidine;

or a pharmaceutically acceptable salt thereof.

In some embodiments, the polynucleotide is an IL-34 antisense oligonucleotide (ASO).

In some embodiments, the polynucleotide is an siRNA. In some embodiments, the siRNA is an IL-34 siRNA that comprises the nucleotide sequence of any one of SEQ ID NO: 3, 5, 7, or 8 or SEQ ID NO: 40-43. In some embodiments, the polynucleotide is a part of an siRNA complex. In some embodiments, the siRNA is an siRNA duplex.

In some embodiments, the polynucleotide is an IL-34 inhibitor. In some embodiments, the IL-34 inhibitor is an IL-34 ASO or a composition comprising such an IL-34 ASO. In some embodiments, the IL-34 ASOs are short synthetic oligonucleotide sequences complementary to an IL-34 transcript (for example, an IL-34 mRNA transcript) or a portion thereof.

In some embodiments, an IL-34 ASO comprises a nucleotide sequence complementary to a portion of an IL-34 mRNA sequence, for example, a mouse or human IL-34 mRNA sequence.

In some embodiments, an IL-34 ASO comprises a nucleotide sequence complementary to a portion of an IL-34 gene sequence, for example a mouse or human IL-34 gene sequence.

In some embodiments, an IL-34 ASO comprises a nucleotide sequence that is complementary or nearly complementary to a portion of an IL-34 mRNA transcript variant, or a portion thereof, for example, human IL-34 mRNA sequence of NCBI Reference Sequence NM_001172771.1 (SEQ ID NO: 24), NM_001172772.1 (SEQ ID NO: 25), NM_152456.2 (SEQ ID NO:26), NM_152456.3 (SEQ ID NO: 44), NM_001172771.2 (SEQ ID NO: 45), NM_001393493.1 (SEQ ID NO: 46), NM_001393495.1 (SEQ ID NO: 47), NM_001172772.2 (SEQ ID NO: 48), NM_001393494.1 (SEQ ID NO: 49), NM_001393496.1 (SEQ ID NO: 50), NM_001393497.1 (SEQ ID NO: 51), or NM_001393498.1 (SEQ ID NO: 52); or mouse IL-34 mRNA sequence of NCBI Reference Sequence NM_001135100.2 (SEQ ID NO: 27) or NM_029646.3 (SEQ ID NO: 28).

In some embodiments, an IL-34 ASO can target IL-34 mRNAs produced from IL-34 genes of one or more species, for example, mouse and human IL-34 mRNA transcripts. For example, an IL-34 ASO can target an IL-34 mRNA of a mammalian IL-34 gene, for example, a human (i.e., *Homo sapiens*) IL-34 gene or a mouse (i.e., *Mus musculus*) IL-34 gene. In particular embodiments, the IL-34 ASO targets a human IL-34 mRNA. In some embodiments, the IL-34 ASO includes a nucleotide sequence that is complementary to a nucleotide sequence of an IL-34 gene or an IL-34 mRNA, or a portion thereof.

In some embodiments, IL-34 ASOs include but are not limited to, an IL-34 ASO that comprises the nucleotide sequence: 5'-CTCACCAAGACCCACAG-3' (SEQ ID NO: 1); 5'-GGCTTTGGGCCGCACCAGCT-3' (SEQ ID NO: 2); 5'-CTTTGGGCCGCACCAGCTTC-3' (SEQ ID NO: 3); 5'-TGGGCCGCACCAGCTTCAGG-3' (SEQ ID NO: 4); 5'-TCCATGACCCGGAAGCAGTT-3' (SEQ ID NO: 5); 5'-TGTTTCATGTACTGAAG-3' (SEQ ID NO: 6); 5'-CTTTGGGCXGCACCAGCTTC-3' (SEQ ID NO: 7); or 5'-TCCATGACCXGGAAGCAGTT-3' (SEQ ID NO: 8), wherein X is 5-methylcytidine.

In some embodiments, the IL-34 ASO comprises the nucleotide sequence 5'-CTTTGGGCCGCACCAGCTTC-3' (SEQ ID NO: 3). In some embodiments, the IL-34 ASO comprises the nucleotide sequence 5'-TCCATGACCCG-GAAGCAGTT-3' (SEQ ID NO:5).

In some embodiments, the IL-34 ASO comprises chemically modified nucleosides. In some embodiments, a chemically modified nucleoside disclosed herein includes, but is not limited to: a locked nucleic acid (LNA) nucleoside, e.g., LNA cytidine, LNA thymidine, LNA adenosine, or LNA guanosine; a nucleoside having a stabilized terminal 5'-phosphate or phosphatase-resistant analogue of 5'-phosphate, e.g., 5'-methyl phosphonate, 5'-methylenephosphonate, a 5'-methylenephosphonate analog, 5'-E-vinyl phosphonate (5'-E-VP), 5'-phosphorothioate, and a 5'-C-methyl analog; a 2'-O-methyl ribonucleoside, e.g., 2'-O-methylcytidine, 2'-O-methylguanosine, 2'-O-methyluridine, 2'-O-methylthymidine, and 2'-O-methyladenosine; a 5-methylpyrimidine, e.g., 5-methylcytosine; a 5-methylpurine, e.g., 5-methylguanine; 5-methyl-2'-O-methylcytidine; 5-methyl-2'-O-methylthymidine; 5-methylcytidine; 5-methyluridine; or 5-methyl 2'-deoxycytidine.

In some embodiments, the IL-34 ASO comprises a 2'-O-methyl ribonucleoside, e.g., 2'-O-methylcytidine, 2'-O-methylguanosine, 2'-O-methyluridine, 2'-O-methylthymidine, and 2'-O-methyladenosine.

In some embodiments, the IL-34 ASO comprises the nucleotide sequence 5'-CTTTGGGCXGCACCAGCTTC-3' (SEQ ID NO: 7), wherein X is 5-methylcytidine. In some embodiments the IL-34 ASO comprises the nucleotide sequence 5'-TCCATGACCXGGAAGCAGTT-3' (SEQ ID NO: 8), wherein X is 5-methylcytidine.

In some embodiments, the ASO comprises a 2'-O-methyl ("2'-OMe") ribonucleoside.

In some embodiments, the ASO has a sequence at least 90% identical to 5'-CxTxTxTxGGGCXGC-ACCAGCxTxTxCx-3' (SEQ ID NO: 40), in which Cx is 2'-O-(2-methoxyethyl)cytidine, Tx is 2'-O-(2-methoxyethyl) thymidine, and X is 5-methylcytidine. In some embodiments, the ASO has a sequence at least 95% identical to 5'-CxTxTxTxGGGCXGCACCAGCxTxTxCx-3' (SEQ ID NO: 40), in which Cx is 2'-O-(2-methoxyethyl)cytidine, Tx is 2'-O-(2-methoxyethyl)thymidine, and X is 5-methylcytidine. In some embodiments, the ASO has a sequence according to 5'-CxTxTxTxGGGCXGCACCAGCxTxTxCx-3' (SEQ ID NO: 40), in which Cx is 2'-O-(2-methoxyethyl) cytidine, Tx is 2'-O-(2-methoxyethyl)thymidine, and X is 5-methylcytidine.

In some embodiments, the ASO has a sequence at least 90% identical to 5'-CxTxTxTGGGC-XGCACCAGCTxTxCx-3' (SEQ ID NO: 41) in which Cx is 2'-O-(2-methoxyethyl)cytidine, Tx is 2'-O-(2-methoxyethyl) thymidine, and X is 5-methylcytidine. In some embodiments, the ASO has a sequence at least 95% identical to 5'-CxTxTxTGGGCXGCACCAGCTxTxCx-3' (SEQ ID NO: 41) in which Cx is 2'-O-(2-methoxyethyl)cytidine, Tx is 2'-O-(2-methoxyethyl)thymidine, and X is 5-methylcytidine. In some embodiments, the ASO has a sequence according to 5'-CxTxTxTGGGCXGCACCAGCTxTxCx-3' (SEQ ID NO: 41) in which Cx is 2'-O-(2-methoxyethyl)cytidine, Tx is 2'-O-(2-methoxyethyl)thymidine, and X is 5-methylcytidine.

In some embodiments, the ASO has a sequence at least 90% identical to 5'-TxCxCxAxTGACCXGGAAGCAxGxTxTx-3' (SEQ ID NO: 42), in which Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine. In some embodiments, the ASO has a sequence at least 95% identical to 5'-TxCxCxAxTGACCXGGAAGCAxGxTxTx-3' (SEQ ID NO: 42), in which Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine. In some embodiments, the ASO has a sequence according to 5'-TxCxCxAxTGACCXGGAAGCAxGxTxTx-3' (SEQ ID NO: 42), in which Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine.

In some embodiments, the ASO has a sequence at least 90% identical to 5'-TxexCxATGACCXGGAAGCAGx-TxTx-3' (SEQ ID NO: 43), in which Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine. In some embodiments, the ASO has a sequence at least 95% identical to 5'-TxCxCxATCiACCXGGAAC-iCAGxTxTx-3' (SEQ ID NO: 43), in which Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine. In some embodiments, the ASO has a sequence according to 5'-TxCxCxATGACCXG-GAAGCAGxTxTx-3' (SEQ ID NO: 43), in which Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine. In some embodiments, contemplated compositions disclosed herein may include a pharmaceutically acceptable salt.

In some embodiments described herein, an IL-34 ASO is a gapmer compound. Gapmer compounds are oligonucleotide sequences that include 5' and 3' flanking groups of modified nucleotides (referred to as region A' and C'). These flanking groups of modified nucleotides are thought to protect the internal group of nucleotides (referred to as region B') from nuclease degradation. Together, the 5' and 3' flanking groups and the internal group form a (5' to 3') A'-B'-C' structure. The internal group of nucleotides is usually from 6 to 10 nucleotides in length. In some embodiments the internal group of oligonucleotides is 10-14 molecules in length. Each 5' or 3' group of flanking nucleotides can be 3, 4, 5, 6, or more nucleotides in length. The 5' and 3' group of flanking nucleotides in a gapmer compound can be the same number of nucleotides in length. Flanking groups of modified nucleotides include, for example, 2'-MOE, 2'-OMe, and LNA nucleotides. Gapmer compound sequences can also incorporate modifications including modified internucleoside linkages (for example, phosphorothioate linkages), 2'-MOEs, 2'-OMes, LNA nucleosides, PNAs, 5-methylcytidine, and other chemically modified nucleosides described herein.

In some embodiments, the gapmer is from 15-20, 15-25, 15-30, 15-35, 20-25, 20-30, 20-35, 25-30, 25-35, or 30-35 nucleotides in length. In particular embodiments, the antisense oligonucleotide is from 15-25 nucleotides in length. In particular embodiments, the antisense oligonucleotide is from 20-25 nucleotides in length. In some embodiments, the antisense oligonucleotide is 15, 16, 17, 18, 19, 20, 21, 22, 23, 24, 25, 26, 27, 28, 29, 30, 31, 32, 33, 34, or 35 nucleotides in length. In some embodiments the gapmer is 20 nucleotides in length.

In some embodiments, region A' consists of 3 or 4 nucleotide analogues, such as 2'-MOE, region B' consists of 12 or 14 DNA bases, and region C' consists of 3 or 4 nucleotide analogues such as 2'-MOE. Such gapmer designs include (A'-B'-C') 3-12-3, 3-14-3, 4-12-4, and 4-14-4.

In some embodiments, region A' consists of 5 or 6 nucleotide analogues, such as 2'-MOE, region B' consists of 8 or 10 DNA bases, and region C' consists of 5 or 6 nucleotide analogues such as 2'-MOE. Such gapmer designs include (A'-B'-C') 5-10-5 and 6-8-6.

In some embodiments the ASO comprises a gapmer of the structure 5'-NxNxNxNNNNNNNNNNNNNNxNxNx-3', wherein N comprises any nucleotide or chemically modified nucleotide and Nx comprises a 2'-O-methyl ("2'-OMe") ribonucleoside. In some embodiments the ASO comprises a gapmer of the structure 5'-NxNxNxNxNNN-NNNNNNNNNxNxNxNx-3', wherein N comprises any nucleotide or chemically modified nucleotide and Nx comprises a 2'-O-methyl ("2'-OMe") ribonucleoside. In some embodiments the ASO comprises a gapmer of the structure 5'-NxNxNxNxNxNNNNNNNNNNxNxNxNxNx-3', wherein N comprises any nucleotide or chemically modified nucleotide and Nx comprises a 2'-O-methyl ("2'-OMe") ribonucleoside. In some embodiments the ASO comprises a gapmer of the structure 5'-NxNxNxNxNxNxNN-NNNNNNNxNxNxNxNxNx-3', wherein N comprises any nucleotide or chemically modified nucleotide and Nx comprises a 2'-O-methyl ("2'-OMe") ribonucleoside. In some embodiments the ASO comprises a gapmer of the structure 5'-NxNxNxNxNxNxNxNNNNNNNxNxNxNxNxNxNx-3', wherein N comprises any nucleotide or chemically modified nucleotide and Nx comprises a 2'-O-methyl ("2'-OMe") ribonucleoside.

In some embodiments the ASO comprises a gapmer of the structure 5'-NxNxNxNNNNNXNNNNNNNNxNxNx-3', wherein N comprises any nucleotide or chemically modified nucleotide, X comprises a 5-methylcytidine, and Nx comprises a 2'-O-methyl ("2'-OMe") ribonucleoside. In some embodiments the ASO comprises a gapmer of the structure 5'-NxNxNxNxNNNNXNNNNNNNNxNxNxNx-3', wherein N comprises any nucleotide or chemically modified nucleotide, X comprises a 5-methylcytidine, and Nx comprises a 2'-O-methyl ("2'-OMe") ribonucleoside. In some embodiments the ASO comprises a gapmer of the structure 5'-NxNxNxNNNNNXNNNNNNNNxNxNx-3', wherein N comprises any nucleotide or chemically modified nucleotide, X comprises a 5-methylcytidine, and Nx comprises a 2'-O-methyl ("2'-OMe") ribonucleoside. In some embodiments the ASO comprises a gapmer of the structure 5'-NxNxNxNxNNNNNXNNNNNNNNxNxNxNx-3', wherein N comprises any nucleotide or chemically modified nucleotide, X comprises a 5-methylcytidine, and Nx comprises a 2'-O-methyl ("2'-OMe") ribonucleoside.

In some embodiments, an IL-34 ASO gapmer includes 2'-MOE nucleosides and the sequence of the IL-34 ASO is selected from one of the following:

5'-CxTxTxTxGGGCXGCACCAGCxTxTxCx-3' (SEQ ID NO: 40), wherein Cx is 2'-O-(2-methoxyethyl) cytidine, Tx is 2'-O-(2-methoxyethyl)thymidine, and X is 5-methylcytidine;

5'-CxTxTxTGGGCXGCACCAGCTxTxCx-3' (SEQ ID NO: 41), wherein Cx is 2'-O-(2-methoxyethyl)cytidine, Tx is 2'-O-(2-methoxyethyl)thymidine, and X is 5-methylcytidine;

5'-TxCxCxAxTGACCXGGAAGCAxGxTxTx-3' (SEQ ID NO: 42), wherein Cx is 2'-O-(2-methoxyethyl) cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; and 5'-TxCxCxATGACCXGGAAGCAGxTxTx-3' (SEQ ID NO: 43), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine, or a pharmaceutically acceptable salt thereof.

In some embodiments, the first, seventeenth, and twentieth nucleosides of SEQ ID NO: 3 (relative to the 5' end) are each independently substituted with 2'-O-(2-methoxyethyl) cytidine; the second, third, fourth, eighteenth, and nineteenth nucleosides of SEQ ID NO: 3 are each independently substituted with 2'-O-(2-methoxyethyl)thymidine; and the ninth nucleoside of SEQ ID NO: 3 is substituted with 5-methylcytidine, resulting in an IL-34 ASO comprising the nucleotide sequence of SEQ ID NO: 40.

In some embodiments, the first and twentieth nucleosides of SEQ ID NO: 3 (relative to the 5' end) are each independently substituted with 2'-O-(2-methoxyethyl)cytidine; the second, third, eighteenth, and nineteenth nucleosides of SEQ ID NO: 3 are each independently substituted with 2'-O-(2-methoxyethyl)thymidine; and the ninth nucleoside of SEQ ID NO: 3 is substituted with 5-methylcytidine, resulting in an IL-34 ASO comprising the nucleotide sequence of SEQ ID NO: 41.

In some embodiments, an IL-34 ASO comprises the nucleotide sequence of SEQ ID NO: 5, wherein at least one nucleoside is a 2'-MOE nucleoside. For example, in some embodiments, the first, nineteenth, and twentieth nucleosides of SEQ ID NO: 5 (relative to the 5' end) are each independently substituted with 2'-O-(2-methoxyethyl)thymidine; the second, and third nucleosides of SEQ ID NO: 5 are each independently substituted with 2'-O-(2-methoxyethyl)cytidine; the fourth and seventeenth nucleosides of SEQ ID NO: 5 are each independently substituted with 2'-O-(2-methoxyethyl)adenosine; the eighteenth nucleoside of SEQ ID NO: 5 is substituted with 2'-O-(2-methoxyethyl)guanosine; and the tenth nucleoside of SEQ ID NO: 5 is substituted with 5-methylcytidine, resulting in an IL-34 ASO comprising the nucleotide sequence of SEQ ID NO: 42.

In some embodiments, an IL-34 ASO comprises the nucleotide sequence of SEQ ID NO: 5, wherein at least one nucleoside is a 2'-MOE nucleoside. For example, in some embodiments, the first, nineteenth, and twentieth nucleosides of SEQ ID NO: 5 (relative to the 5' end) are each independently substituted with 2'-O-(2-methoxyethyl)thymidine; the second, and third nucleosides of SEQ ID NO: 5 are each independently substituted with 2'-O-(2-methoxyethyl)cytidine; the eighteenth nucleoside of SEQ ID NO: 5 is substituted with 2'-O-(2-methoxyethyl)guanosine; and the tenth nucleoside of SEQ ID NO: 5 is substituted with 5-methylcytidine, resulting in an IL-34 ASO comprising the nucleotide sequence of SEQ ID NO: 43.

For example, in some embodiments, an IL-34 ASO comprises the nucleotide sequence of SEQ ID NO: 3, wherein at least one nucleoside is a 2'-MOE nucleoside. For example, in some embodiments, the first, seventeenth, and twentieth nucleosides of SEQ ID NO: 3 (relative to the 5' end) are each independently substituted with 2'-O-(2-methoxyethyl)cytidine; the second, third, fourth, eighteenth, and nineteenth nucleosides of SEQ ID NO: 3 are each independently substituted with 2'-O-(2-methoxyethyl)thymidine; the fifth and sixteenth nucleosides of SEQ ID NO: 3 are each independently substituted with 2'-O-(2-methoxyethyl)guanosine; and the ninth nucleoside of SEQ ID NO: 3 is substituted with 5-methylcytidine, resulting in an IL-34 ASO comprising the nucleotide sequence of SEQ ID NO: 16.

In some embodiments, the first, seventeenth, and twentieth nucleosides of SEQ ID NO: 3 (relative to the 5' end) are each independently substituted with 2'-O-(2-methoxyethyl) cytidine; the second, third, fourth, eighteenth, and nineteenth nucleosides of SEQ ID NO: 3 are each independently substituted with 2'-O-(2-methoxyethyl)thymidine; the fifth, sixth and sixteenth nucleosides of SEQ ID NO: 3 are each independently substituted with 2'-O-(2-methoxyethyl)guanosine; the fifteenth nucleoside of SEQ ID NO: 3 is substituted with 2'-O-(2-methoxyethyl)adenosine; and the ninth nucleoside of SEQ ID NO: 3 is substituted with 5-methylcytidine, resulting in an IL-34 ASO comprising the nucleotide sequence of SEQ ID NO: 18.

In some embodiments, the first, eighth, eleventh, thirteenth, fourteenth, seventeenth, and twentieth nucleosides of SEQ ID NO: 3 (relative to the 5' end) are each independently substituted with 2'-O-(2-methoxyethyl)cytidine; all thymidines of SEQ ID NO: 3 are each independently substituted with 2'-O-(2-methoxyethyl)thymidine; all guanosines of SEQ ID NO: 3 are each independently substituted with 2'-O-(2-methoxyethyl)guanosine; all adenosines of SEQ ID NO:3 are each independently substituted with 2'-O-(2-methoxyethyl)adenosine; and the ninth nucleoside of SEQ ID NO: 3 is substituted with 5-methylcytidine, resulting in an IL-34 ASO comprising the nucleotide sequence of SEQ ID NO: 20.

In other embodiments, one or more nucleoside(s) in SEQ ID NO: 3 may be substituted with 2'-MOE nucleosides other than those substituted in any one of SEQ ID NO: 16, 18, 20, 40, or 41. In still other embodiments, SEQ ID NO: 3 may be substituted with 2'-MOE nucleosides at one or more positions other than those substituted in any one of SEQ ID NO: 16, 18, 20, 40, or 41.

In some embodiments, an IL-34 ASO comprises the nucleotide sequence of SEQ ID NO: 5, wherein at least one nucleoside is a 2'-MOE nucleoside. For example, in some embodiments, the first, fifth, nineteenth, and twentieth nucleosides of SEQ ID NO: 5 (relative to the 5' end) are each independently substituted with 2'-O-(2-methoxyethyl)thymidine; the second, third, and sixteenth nucleosides of SEQ ID NO: 5 are each independently substituted with 2'-O-(2-methoxyethyl)cytidine; the fourth and seventeenth nucleosides of SEQ ID NO: 5 are each independently substituted with 2'-O-(2-methoxyethyl)adenosine; the eighteenth nucleoside of SEQ ID NO: 5 is substituted with 2'-O-(2-methoxyethyl)guanosine; and the tenth nucleoside of SEQ ID NO: 5 is substituted with 5-methylcytidine, resulting in an IL-34 ASO comprising the nucleotide sequence of SEQ ID NO: 17.

In some embodiments, the first, fifth, nineteenth, and twentieth nucleosides of SEQ ID NO: 5 (relative to the 5' end) are each independently substituted with 2'-O-(2-methoxyethyl)thymidine; the second, third, and sixteenth nucleosides of SEQ ID NO: 5 are each independently substituted with 2'-O-(2-methoxyethyl)cytidine; the fourth and seventeenth nucleosides of SEQ ID NO: 5 are each independently substituted with 2'-O-(2-methoxyethyl)adenosine; the sixth, fifteenth, and eighteenth nucleosides of SEQ ID NO: 5 are each independently substituted with 2'-O-(2-methoxyethyl)guanosine; and the tenth nucleoside of SEQ ID NO: 5 is substituted with 5-methylcytidine, resulting in an IL-34 ASO comprising the nucleotide sequence of SEQ ID NO: 19.

In some embodiments, the second, third, eighth, ninth, and sixteenth nucleosides of SEQ ID NO: 5 (relative to the 5' end) are each independently substituted with 2'-O-(2-methoxyethyl)cytidine; all thymidines of SEQ ID NO: 5 are each independently substituted with 2'-O-(2-methoxyethyl) thymidine; all guanosines of SEQ ID NO: 5 are each independently substituted with 2'-O-(2-methoxyethyl) guanosine; all adenosines of SEQ ID NO: 5 are each independently substituted with 2'-O-(2-methoxyethyl)adenosine; and the tenth nucleoside of SEQ ID NO: 5 is substituted with 5-methylcytidine, resulting in an IL-34 ASO comprising the nucleotide sequence of SEQ ID NO: 21.

In other embodiments, one or more nucleoside(s) in SEQ ID NO: 5 may be substituted with 2'-MOE nucleosides other than those substituted in any one of SEQ ID NO: 17, 19, 21, 42, or 43. In still other embodiments, SEQ ID NO: 5 may be substituted with 2'-MOE nucleosides at one or more positions other than those substituted in any one of SEQ ID NO: 17, 19, 21, 42, or 43.

In some embodiments, an ASO described herein includes at least one modified internucleoside linkage. As used herein, "internucleoside linkage" means the connection between the 3' position of a nucleoside and the 5' position of an adjacent nucleoside. A "modified internucleoside linkage" refers to a connection between the 3' position of a nucleoside and the 5' position of an adjacent nucleoside that is not natural. In some embodiments, a modified internucleoside linkage includes, but is not limited to: a phosphorothioate linkage; a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, an aminoalkylphosphoramidate linkage, a thiophosphoramidate linkage, a thionoalkylphosphonate linkage, a thionoalkylphosphotriester linkage, a thiophosphate linkage, a selenophosphate linkage, or a boranophosphate linkage.

In some embodiments, ASOs described herein includes at least one chemically modified nucleoside and at least one modified internucleoside linkage. In some embodiments, ASOs described herein includes at least one chemically modified nucleoside or at least one modified internucleoside linkage.

IL-34 ASOs described herein, can include chemically modified nucleosides, including modified ribonucleosides and modified deoxyribonucleosides. Chemically modified nucleosides include, but are not limited to, 2'-O-(2-methoxyethyl) modifications, for example, 2'-O-(2-methoxyethyl) guanosine, 2'-O-(2-methoxyethyl)adenosine, 2'-O-(2-methoxyethyl)cytosine, 2'-O-(2-methoxyethyl)uridine, and 2'-O-(2-methoxyethyl)thymidine. Chemically modified nucleosides also include, but are not limited to, locked nucleic acid (LNA), 2'-O-methyl, 2'-fluoro, and 2'-fluoro-β-D-arabinonucleotide (FANA) modifications. Chemically modified nucleosides that can be included in IL-34 ASOs described herein are described in Johannes and Lucchino, (2018) "Current Challenges in Delivery and Cytosolic Translocation of Therapeutic RNAs" *Nucleic Acid Ther.* 28(3): 178-93; Rettig and Behlke, (2012) "Progress toward in vivo use of siRNAs-II" *Mol Ther* 20:483-512; and Khvorova and Watts, (2017) "The chemical evolution of oligonucleotide therapies of clinical utility" *Nat Biotechnol.*, 35(3):238-48, the contents of each of which are incorporated by reference herein. In certain embodiments, the disclosure provides mixed modalities of polynucleotide complementary to IL-34, or a portion thereof, e.g., a combination of an IL-34 peptide nucleic acid (PNA) and an IL-34 locked nucleic acid (LNA).

IL-34 ASOs described herein can include chemical modifications that promote stabilization of an oligonucleotide's terminal 5'-phosphate and phosphatase-resistant analogs of 5'-phosphate. Chemical modifications that promote oligonucleotide terminal 5'-phosphate stabilization or which are phosphatase-resistant analogs of 5'-phosphate include, but are not limited to, 5'-methyl phosphonate, 5'-methylenephosphonate, 5'-methylenephosphonate analogs, 5'-E-vinyl phosphonate (5'-E-VP), 5'-phosphorothioate, and 5'-C-methyl analogs. Chemical modifications that promote ASO terminal 5'-phosphate stabilization and phosphatase-resistant analogues of 5'-phosphate are described in Khvorova and Watts, (2017) "The chemical evolution of oligonucleotide therapies of clinical utility" *Nat Biotechnol.*, 35(3): 238-48, the contents of which are incorporated by reference herein.

In some embodiments described herein, IL-34 ASOs described herein can include chemically modified nucleosides, including 2'-O-methyl ribonucleosides, for example, 2'-O-methylcytidine, 2'-O-methylguanosine, 2'-O-methyluridine, 2'-O-methylthymidine, and/or 2'-O-methyladenosine. IL-34 ASOs described herein can include one or more chemically modified nucleosides, wherein the chemically modified nucleosides comprise bases, including a 5-methylpyrimidine, for example, 5-methylcytosine, and/or a 5-methylpurine, for example, 5-methylguanine. IL-34 ASOs described herein can include any of the following chemically modified nucleosides: 5-methyl-2'-O-methylcytidine, 5-methyl-2'-O-methylthymidine, 5-methylcytidine, 5-methyluridine, and/or 5-methyl 2'-deoxycytidine.

In some embodiments, IL-34 ASOs described herein include an IL-34 ASO that includes the nucleotide sequence: 5'-CTCACCAAGACCCACAG-3' (SEQ ID NO: 1), wherein at least one nucleoside is a chemically modified nucleoside and/or at least one linkage is a modified internucleoside linkage; 5'-GGCTTTGGGCCGCACCAGCT-3' (SEQ ID NO: 2), wherein at least one nucleoside is a chemically modified nucleoside and/or at least one linkage is a modified internucleoside linkage; 5'-CTTTGGGCCGCACCAGCTTC-3' (SEQ ID NO: 3), wherein at least one nucleoside is a chemically modified nucleoside and/or at least one linkage is a modified internucleoside linkage; 5'-TGGGCCGCACCAGCTTCAGG-3' (SEQ ID NO: 4), wherein at least one nucleoside is a chemically modified nucleoside and/or at least one linkage is a modified internucleoside linkage; 5'-TCCATGACCCG-GAAGCAGTT-3' (SEQ ID NO: 5), wherein at least one nucleoside is a chemically modified nucleoside and/or at least one linkage is a modified internucleoside linkage; or 5'-TGTTTCATGTACTGAAG-3' (SEQ ID NO: 6), wherein at least one nucleoside is a chemically modified nucleoside and/or at least one linkage is a modified internucleoside linkage, or a pharmaceutically acceptable salt thereof.

In some embodiments, an IL-34 ASO comprises the nucleotide sequence of SEQ ID NO: 3, wherein at least one nucleoside is a chemically modified nucleoside. For example, in some embodiments, the third cytidine (from the 5' end) of SEQ ID NO: 3 may be substituted with a chemically modified nucleoside. In some embodiments, the third cytidine (from the 5' end) of SEQ ID NO: 3 is substituted for 5-methylcytidine, resulting in an IL-34 ASO comprising the nucleotide sequence of SEQ ID NO: 7. In some embodiments, a nucleoside other than the third cytidine (from the 5' end) of SEQ ID NO: 3 is substituted with a chemically modified nucleoside, resulting in an IL-34 ASO having a nucleotide sequence other than SEQ ID NO: 7. In some embodiments, the third cytidine (from the 5' end) of SEQ ID NO: 3 is substituted with a chemically modified nucleoside that is not 5-methylcytidine, resulting in an IL-34 ASO having a nucleotide sequence other than SEQ ID NO: 7.

In some embodiments, an IL-34 ASO comprises the nucleotide sequence of SEQ ID NO: 5, wherein at least one nucleoside is a chemically modified nucleoside. For example, in some embodiments, the fifth cytidine (from the 5' end) of SEQ ID NO: 5 may be substituted with a chemically modified nucleoside. In some embodiments the fifth cytidine (from the 5' end) of SEQ ID NO: 5 is substituted for 5-methylcytidine, resulting in an IL-34 ASO comprising the nucleotide sequence of SEQ ID NO: 8. In some embodiments a nucleoside other than the fifth cytidine (from the 5' end) of SEQ ID NO: 3 is substituted with a chemically modified nucleoside, resulting in an IL-34 ASO having a nucleotide sequence other than SEQ ID NO: 8. In some embodiments, the fifth cytidine (from the 5' end) of SEQ ID NO: 3 is substituted with a chemically modified nucleoside that is not 5-methylcytidine, resulting in an IL-34 ASO having a nucleotide sequence other than SEQ ID NO: 8.

IL-34 ASOs described herein also include IL-34 ASOs that include one or more LNA nucleotides. For example, IL-34 ASOs described herein include an IL-34 ASO that includes the nucleotide sequence of any of the following:

5'-cttTGGGCXGCACCAGCttc-3' (SEQ ID NO: 9), wherein c is LNA cytidine, t is LNA thymidine, and X is 5-methylcytidine;

5'-ctttGGGCXGCACCAGcttc-3' (SEQ ID NO: 10), wherein c is LNA cytidine, t is LNA thymidine, and X is 5-methylcytidine;

5'-cttTGGGCcgCACCAGCttc-3' (SEQ ID NO: 11), wherein c is LNA cytidine, t is LNA thymidine, and g is LNA guanosine;

5'-cttTGGGCcGCACCAGCttc-3' (SEQ ID NO: 12), wherein c is LNA cytidine and t is LNA thymidine;

5'-ggcXGCACCAGCttc-3' (SEQ ID NO: 13), wherein c is LNA cytidine, t is LNA thymidine, g is LNA guanosine, and X is 5-methylcytidine;

5'-cttTGGGCXGCACcag-3' (SEQ ID NO: 14), wherein c is LNA cytidine, t is LNA thymidine, g is LNA guanosine, a is LNA adenosine, and X is 5-methylcytidine; and 5'-tgaCCXGGAAGCAgtt-3' (SEQ ID NO: 15), wherein a is LNA adenosine, t is LNA thymidine, g is LNA guanosine, and X is 5-methylcytidine, or a pharmaceutically acceptable salt thereof.

In some embodiments, an IL-34 ASO comprises the nucleotide sequence of SEQ ID NO: 3, wherein at least one nucleoside is an LNA. For example, in some embodiments, the first and twentieth nucleosides of SEQ ID NO: 3 (relative to the 5' end) are each independently substituted with LNA cytidine; the second, third, eighteenth, and nineteenth nucleosides of SEQ ID NO: 3 are each independently substituted with LNA thymidine; and the ninth nucleoside of SEQ ID NO: 3 is substituted with 5-methylcytidine, resulting in an IL-34 ASO comprising the nucleotide sequence of SEQ ID NO: 9.

In another embodiment, the first, seventeenth, and twentieth nucleosides of SEQ ID NO: 3 (relative to the 5' end) are each independently substituted with LNA cytidine; the second, third, fourth, eighteenth, and nineteenth nucleosides of SEQ ID NO: 3 are each independently substituted with LNA thymidine; and the ninth nucleoside of SEQ ID NO: 3 is substituted with 5-methylcytidine, resulting in an IL-34 ASO comprising the nucleotide sequence of SEQ ID NO: 10.

In another embodiment, the first, ninth, and twentieth nucleosides of SEQ ID NO: 3 (relative to the 5' end) are each independently substituted with LNA cytidine; the second, third, eighteenth, and nineteenth nucleosides of SEQ ID NO: 3 are each independently substituted with LNA thymidine; and the tenth nucleoside of SEQ ID NO: 3 is substituted with LNA guanosine, resulting in an IL-34 ASO comprising the nucleotide sequence of SEQ ID NO: 11.

In yet another embodiment, the first, ninth, and twentieth nucleosides of SEQ ID NO: 3 (relative to the 5' end) are each independently substituted with LNA cytidine; and the second, third, eighteenth, and nineteenth nucleosides of SEQ ID NO: 3 are each independently substituted with LNA thymidine, resulting in an IL-34 ASO comprising the nucleotide sequence of SEQ ID NO: 12.

In other embodiments, one or more nucleoside(s) in SEQ ID NO: 3 may be substituted with LNA nucleotides other than those substituted in any one of SEQ ID NO: 9, 10, 11, or 12. In other embodiments, SEQ ID NO: 3 may be substituted with LNA nucleotides at one or more positions other than those substituted in any one of SEQ ID NO: 9, 10, 11, or 12.

In particular embodiments, an IL-34 ASO includes 2'-MOE nucleosides and the sequence of the IL-34 ASO is selected from one of the following:

5'-CxTxTxTxGxGGCXGCACCAGxCxTxTxCx-3' (SEQ ID NO: 16), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine;

5'-TxCxCxAxTxGACCXGGAAGCxAxGxTxTx-3' (SEQ ID NO: 17), wherein Cx is 2'-O-(2-methoxyethyl)cytidine, Tx is 2'-O-(2-methoxyethyl)thymidine, Gx is 2'-O-(2-methoxyethyl)guanosine, Ax is 2'-O-(2-methoxyethyl)adenosine, and X is 5-methylcytidine;

5'-CxTxTxTxGxGxGCXGCACCAxGxCxTxTxCx-3' (SEQ ID NO: 18), wherein Cx is 2'-O-(2-methoxyethyl)cytidine, Tx is 2'-O-(2-methoxyethyl)thymidine, Gx is 2'-O-(2-methoxyethyl)guanosine, Ax is 2'-O-(2-methoxyethyl)adenosine, and X is 5-methylcytidine;

5'-TxCxCxAxTxGxACCXGGAAGxCxAxGxTxTx-3' (SEQ ID NO: 19), wherein Cx is 2'-O-(2-methoxyethyl)cytidine, Tx is 2'-O-(2-methoxyethyl)thymidine, Gx is 2'-O-(2-methoxyethyl)guanosine, Ax is 2'-O-(2-methoxyethyl)adenosine, and X is 5-methylcytidine;

5'-CxTxTxTxGxGxGxCxXGxCxAxCxCxAxGxCxTxTxCx-3' (SEQ ID NO: 20), wherein Cx is 2'-O-(2-methoxyethyl)cytidine, Tx is 2'-O-(2-methoxyethyl)

thymidine, Gx is 2'-O-(2-methoxyethyl)guanosine, Ax is 2'-O-(2-methoxyethyl)adenosine, and X is 5-methylcytidine; and 5'-TxCxCxAxTxGxAxCxCxXGxGxAxAxGxCxAxGx-TxTx-3' (SEQ ID NO: 21), wherein Cx is 2'-O-(2-methoxyethyl)cytidine, Tx is 2'-O-(2-methoxyethyl)thymidine, Gx is 2'-O-(2-methoxyethyl)guanosine, Ax is 2'-O-(2-methoxyethyl)adenosine, and X is 5-methylcytidine, or a pharmaceutically acceptable salt thereof.

Additionally, in some embodiments, an IL-34 ASO includes 2'-OMe nucleosides and the sequence of the IL-34 ASO is selected from one of the following:

5'-CyTyTyTyGyGGCXGCACCAGyCyTyTyCy-3' (SEQ ID NO: 22), wherein Cy is 2'-O-methylcytidine, Ty is 2'-O-methylthymidine, Gy is 2'-O-methylguanosine, and X is 5-methylcytidine; and 5'-TyCyCyAyTyGACCXGGAAGCyAyGyTyTy-3' (SEQ ID NO: 23), wherein Cy is 2'-O-methylcytidine, Ty is 2'-O-methylthymidine, Gy is 2'-O-methylguanosine, Ay is 2'-O-methyladenosine, and X is 5-methylcytidine, or a pharmaceutically acceptable salt thereof.

For example, in some embodiments, an IL-34 ASO comprises the nucleotide sequence of SEQ ID NO: 3, wherein at least one nucleoside is a 2'-OMe nucleoside. For example, in some embodiments, the first, seventeenth and twentieth nucleosides of SEQ ID NO: 3 (relative to the 5' end) are each independently substituted with 2'-O-methylcytidine; the second, third, fourth, eighteenth, and nineteenth nucleosides of SEQ ID NO: 3 are each independently substituted with 2'-O-methylthymidine; the fifth and sixteenth nucleosides of SEQ ID NO: 3 are each independently substituted with 2'-O-methylguanosine; and the ninth nucleoside of SEQ ID NO: 3 is substituted with 5-methylcytidine, resulting in an IL-34 ASO comprising the nucleotide sequence of SEQ ID NO: 22.

In other embodiments, one or more nucleoside(s) in SEQ ID NO: 3 may be substituted with 2'-OMe nucleosides other than those substituted in SEQ ID NO: 22. In still other embodiments, SEQ ID NO: 3 may be substituted with 2'-OMe nucleosides at one or more positions other than those substituted in SEQ ID NO: 22.

In some embodiments, an IL-34 ASO comprises the nucleotide sequence of SEQ ID NO: 5, wherein at least one nucleoside is a 2'-OMe nucleoside. For example, in some embodiments, the first, fifth, nineteenth, and twentieth nucleosides of SEQ ID NO: 5 (relative to the 5' end) are each independently substituted with 2'-O-methylthymidine; the second, third, and sixteenth nucleosides of SEQ ID NO: 5 are each independently substituted with 2'-O-methylcytidine; the fourth and seventeenth nucleosides of SEQ ID NO: 5 are each independently substituted with 2'-O-methyladenosine; the eighteenth nucleoside of SEQ ID NO: 5 is substituted with 2'-O-methylguanosine; and the tenth nucleoside of SEQ ID NO: 5 is substituted with 5-methylcytidine, resulting in an IL-34 ASO comprising the nucleotide sequence of SEQ ID NO: 23.

In other embodiments, one or more nucleoside(s) in SEQ ID NO: 5 may be substituted with 2'-OMe nucleosides other than those substituted in SEQ ID NO: 23. In still other embodiments, SEQ ID NO: 5 may be substituted with 2'-OMe nucleosides at one or more positions other than those substituted in SEQ ID NO: 23.

IL-34 ASOs described herein can include a phosphate backbone where one or more of the oligonucleoside linkages is a modified internucleoside linkage. For example, in some embodiments, an IL-34 ASO described herein may comprise at least one phosphate linkage. IL-34 ASOs described herein may include one or more modified internucleoside linkages selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, an aminoalkylphosphoramidate linkage, a thiophosphoramidate linkage, a thionoalkylphosphonate linkage, a thionoalkylphosphotriester linkage, a thiophosphate linkage, a selenophosphate linkage, and a boranophosphate linkage. In some embodiments of IL-34 ASOs described herein, at least one internucleoside linkage of the nucleotide sequence is a phosphorothioate linkage. For example, in some embodiments of IL-34 ASOs described herein, one, two, three, or more internucleoside linkages of the nucleotide sequence is a phosphorothioate linkage. In preferred embodiments of IL-34 ASOs described herein, all internucleoside linkages of the nucleotide sequence are phosphorothioate linkages. Thus, in some embodiments, all of the nucleotide linkages of an IL-34 ASO of any of SEQ ID NOs: 1-23 or SEQ ID NOs: 40-43 are phosphorothioate linkages. For example, in some embodiments, all of the nucleotide linkages of an IL-34 ASO of SEQ ID NO: 3 are phosphorothioate linkages. In another example, in some embodiments, all of the nucleotide linkages of an IL-34 ASO of SEQ ID NO: 7 are phosphorothioate linkages. In some embodiments, one or more of the nucleotide linkages of an IL-34 ASO of any of SEQ ID NOs: 1-23 or SEQ ID NOs: 40-43 are phosphorothioate linkages. For example, in some embodiments, one or more of the nucleotide linkages of an IL-34 ASO of SEQ ID NO: 3 are phosphorothioate linkages. In another example, in some embodiments, one or more of the nucleotide linkages of an IL-34 ASO of SEQ ID NO: 7 are phosphorothioate linkages.

It is contemplated that in some embodiments, a disclosed IL-34 ASO, or a pharmaceutically acceptable salt thereof, may optionally have at least one modified nucleobase, e.g., 5-methylcytosine, and/or at least one methylphosphonate nucleotide, which is placed, for example, either at only one of the 5' or 3' ends or at both 5' and 3' ends or along the oligonucleotide sequence.

Contemplated IL-34 ASOs may optionally include at least one modified sugar. For example, the sugar moiety of at least one nucleotide constituting the oligonucleotide is a ribose in which the 2'-OH group may be replaced by any one group selected from the group consisting of OR, R, R'OR, SH, SR, $NH_2$, $NR_2$, $N_3$, CN, F, Cl, Br, and I (wherein R is an alkyl or aryl and R' is an alkylene).

Antisense oligonucleotides can be designed such that the targeting portion of the incorporated nucleotide sequence of each antisense oligonucleotide is completely or almost completely complementary to the IL-34 mRNA sequence, or portion thereof; or the mRNA sequence of an IL-34 interaction partner or a portion thereof. Incorporation of such complementary or nearly complementary nucleotide sequences allows one to engineer antisense oligonucleotides with a high degree of specificity for a given target. Specificity can be assessed via measurement of parameters such as dissociation constant, or other criteria such as changes in protein or RNA expression levels or other assays that measure IL-34 activity or expression. In some embodiments, the IL-34 ASOs disclosed herein are IL-34 inhibitors.

In some embodiments, polynucleotides complementary to IL-34, or a portion thereof, disclosed herein are IL-34 inhibitors comprising IL-34 small interfering RNAs (siRNAs).

Small interfering RNAs (siRNAs) are double-stranded RNA molecules of approximately 20-25 base pairs in length (but which can also be, for example, 18-30 base pairs in length) that take advantage of RNAi machinery (e.g., Drosha and RISC) to bind and target mRNA for degradation. siRNAs are not dependent upon plasmids or vectors for expression, and can generally be delivered directly to a target cell, for instance, by transfection. IL-34 siRNAs are double-stranded RNA sequences that include an RNA sequence complementary to an IL-34 mRNA sequence, and which prevent IL-34 protein translation.

In some embodiments, the IL-34 siRNA is 17, 18, 19, 20, 21, 22, 23, 24, 25, 26, 27, 28, 29, 30, 20-25, 20-30, or 25-30 nucleotides in length. In some embodiments the IL-34 siRNA is from 20-25 nucleotides in length. In some embodiments, the IL-34 siRNA is no more than 20, 25, or 30 nucleotides in length.

In some embodiments, IL-34 siRNAs described herein include siRNAs that include the nucleotide sequence of any one of SEQ ID NOs: 1-23 or SEQ ID NOs: 40-43, for example, the nucleotide sequence of any one of SEQ ID NOs: 1-8, or a pharmaceutically acceptable salt thereof.

In some embodiments, the IL-34 comprises modified nucleotides. In some embodiments, one or more cytidines are replaced with 5-methylcytidine.

In some embodiments, IL-34 siRNAs described herein can include a phosphate backbone where one or more of the oligonucleoside linkages is a modified internucleoside linkage. For example, in some embodiments, an IL-34 siRNAs described herein may comprise at least one phosphate linkage. IL-34 siRNAs described herein may include one or more modified internucleoside linkages selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, an aminoalkylphosphoramidate linkage, a thiophosphoramidate linkage, a thionoalkylphosphonate linkage, a thionoalkylphosphotriester linkage, a thiophosphate linkage, a selenophosphate linkage, and a boranophosphate linkage. In some embodiments of IL-34 siRNAs s described herein, at least one internucleoside linkage of the nucleotide sequence is a phosphorothioate linkage. For example, in some embodiments of IL-34 siRNAs described herein, one, two, three, or more internucleoside linkages of the nucleotide sequence is a phosphorothioate linkage. In preferred embodiments of IL-34 siRNAs described herein, all internucleoside linkages of the nucleotide sequence are phosphorothioate linkages. Thus, in some embodiments, all of the nucleotide linkages of an IL-34 siRNAs of any of SEQ ID NOs: 1-23 or SEQ ID NOs: 40-43 are phosphorothioate linkages. For example, in some embodiments, all of the nucleotide linkages of an IL-34 siRNAs of SEQ ID NO: 3 are phosphorothioate linkages. In another example, in some embodiments, all of the nucleotide linkages of an IL-34 siRNAs of SEQ ID NO: 7 are phosphorothioate linkages. In some embodiments, one or more of the nucleotide linkages of an IL-34 siRNAs of any of SEQ ID NOs: 1-23 or SEQ ID NOs: 40-43 are phosphorothioate linkages. For example, in some embodiments, one or more of the nucleotide linkages of an IL-34 siRNAs of SEQ ID NO: 3 are phosphorothioate linkages. In another example, in some embodiments, one or more of the nucleotide linkages of an IL-34 siRNAs of SEQ ID NO: 7 are phosphorothioate linkages.

Peptide nucleic acids (PNAs) are short, artificially synthesized polymers with a structure that mimics DNA or RNA. PNAs include a backbone composed of repeating N-(2-aminoethyl)-glycine units linked by peptide bonds. IL-34 PNAs described herein can be used as antisense therapeutics that bind to IL-34 RNA sequences with high specificity and inhibit IL-34 gene expression.

Locked nucleic acids (LNAs) are oligonucleotide sequences that include one or more modified RNA nucleotides in which the ribose moiety is modified with an extra bridge connecting the 2' oxygen and 4' carbon. LNAs are believed to have higher Tm's than analogous oligonucleotide sequences. IL-34 LNAs described herein can be used as antisense therapeutics that bind to IL-34 RNA sequences with high specificity and inhibit IL-34 gene expression.

Morpholino oligomers are oligonucleotide compounds that include DNA bases attached to a backbone of methylenemorpholine rings linked through phosphorodiamidate groups. Morpholino oligomers of the present invention can be designed to bind to specific IL-34 RNA sequences of interest (for example, IL-34 mRNA or IL-34 pre-mRNA sequences of interest), thereby preventing gene expression. IL-34 morpholino oligomers described herein can be used as antisense therapeutics that bind to IL-34 mRNA sequences with high specificity and inhibit IL-34 gene expression. IL-34 morpholino oligomers described herein can also be used to bind IL-34 pre-mRNA sequences, altering IL-34 pre-mRNA splicing and IL-34 gene expression.

Small hairpin RNAs (shRNAs) are generally RNA molecules with a hairpin-like structure that can be used to silence gene expression. shRNAs are generally expressed from plasmids encoding the shRNA sequence, and can be expressed from viral vectors to allow lentiviral, adenoviral, or adeno-associated viral expression. Without being bound by theory, it is believed that shRNA inhibits gene expression by taking advantage of RNA interference (RNAi) processes. In brief, the shRNA transcript is processed by Drosha and Dicer, and then loaded onto the RNA-induced silencing complex (RISC), allowing targeting of specific mRNA, and either mRNA degradation or repression of protein translation. IL-34 shRNAs described herein can inhibit gene expression of IL-34.

MicroRNAs (miRNAs) are small non-coding RNA molecule containing about 22 nucleotides that function in RNA silencing and post-transcriptional regulation of gene expression. miRNAs include sequences that are complementary to portions of an mRNA sequence. miRNAs are produced from long, single-stranded RNA molecules exhibiting highly specific stem—loop structures. Artificial miRNAs are designed by replacing the mature 21 nucleotide sequence of naturally occurring miRNA sequences with 21 nucleotide sequences from a target, for example, an IL-34 mRNA target.

In some embodiments, the polynucleotide complementary to IL-34, or a portion thereof, described herein can include chemical modifications that promote stabilization of an oligonucleotide's terminal 5'-phosphate and phosphatase-resistant analogs of 5'-phosphate. Chemical modifications that promote oligonucleotide terminal 5'-phosphate stabilization or which are phosphatase-resistant analogs of 5'-phosphate include, but are not limited to, 5'-methyl phosphonate, 5'-methylenephosphonate, 5'-methylenephosphonate analogs, 5'-E-vinyl phosphonate (5'-E-VP), 5'-phosphorothioate, and 5'-C-methyl analogs. Chemical modifications that promote ASO terminal 5'-phosphate stabilization and phosphatase-resistant analogues of 5'-phosphate are described in Khvorova and Watts, (2017) "The chemical evolution of oligonucleotide therapies of clinical utility" *Nat Biotechnol.,* 35(3):238-48, the contents of which are incorporated by reference herein.

In some embodiments described herein, polynucleotides complementary to IL-34, or a portion thereof, can include chemically modified nucleosides, for example, 2'-O-methyl ribonucleosides, for example, 2'-O-methylcytidine, 2'-O-methylguanosine, 2'-O-methyluridine, 2'-O-methylthymidine, and/or 2'-O-methyladenosine. Polynucleotides complementary to IL-34, or a portion thereof, described herein can include one or more chemically modified bases, including a 5-methylpyrimidine, for example, 5-methylcytosine, and/or a 5-methylpurine, for example, 5-methylguanine. Polynucleotides complementary to IL-34, or a portion thereof, described herein can include any of the following chemically modified nucleosides: 5-methyl-2'-O-methylcytidine, 5-methyl-2'-O-methylthymidine, 5-methylcytidine, 5-methyluridine, and/or 5-methyl 2'-deoxycytidine.

2'-OMe nucleotides are found naturally in tRNA and other small RNAs. Incorporation of 2'-OMe nucleotides into oligonucleotide sequences prevents nuclease degradation and increases stability against hydrolysis. Incorporation of 2'-Me modification in oligonucleotides generally increases the $T_m$ of RNA-RNA duplexes by 1-4° C. per addition.

Introduction of a 2'-MOE group generally increases the $T_m$ of the resulting oligonucleotide by about 1.1° C. and improves the resistance to degradation by nuclease. Additionally, 2'-MOE oligos are often used in gapmer compounds to preserve the RNase H-mediated degradation of target mRNA strands.

Polynucleotides complementary to IL-34, or a portion thereof, described herein can include a phosphate backbone where one or more of the oligonucleoside linkages is a phosphate linkage. Polynucleotides complementary to IL-34, or a portion thereof, described herein may include a modified oligonucleotide backbone, where one or more of the nucleoside linkages of the nucleotide sequence is selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, an aminoalkylphosphoramidate linkage, a thiophosphoramidate linkage, a thionoalkylphosphonate linkage, a thionoalkylphosphotriester linkage, a thiophosphate linkage, a selenophosphate linkage, and a boranophosphate linkage. In some embodiments of polynucleotides complementary to IL-34, or a portion thereof, described herein, at least one internucleoside linkage of the nucleotide sequence is a phosphorothioate linkage. For example, in some embodiments of polynucleotides complementary to IL-34, or a portion thereof, described herein, one, two, three, or more internucleoside linkages of the nucleotide sequence is a phosphorothioate linkage. In some embodiments, polynucleotides complementary to IL-34, or a portion thereof, described herein, all internucleoside linkages of the nucleotide sequence are phosphorothioate linkages. Thus, in some embodiments, all of the nucleotide linkages of a polynucleotide complementary to IL-34, or a portion thereof, of any of SEQ ID NOs: 1-23 or SEQ ID NOs: 40-43 are phosphorothioate linkages. In some embodiments, one or more of the nucleotide linkages of a polynucleotide complementary to IL-34, or a portion thereof, of any of SEQ ID NOs: 1-23 or SEQ ID NOs: 40-43 are phosphorothioate linkages. For example, an IL-34 siRNA described herein, can include 1, 2, 3, 4, 5, 6, 7, 8, 9, 10, 11, 12, 13, 14, 15, 16, 17, 18, 19, or more phosphorothioate linkages. In some embodiments, all of the nucleotide linkages of an IL-34 siRNA of any of SEQ ID NOs: 1-8 are phosphorothioate linkages.

Autoimmune and Inflammatory Disease

Provided herein, in some embodiments, are methods for treating an autoimmune or inflammatory disease, comprising administering a polynucleotide complementary to IL-34, or a portion thereof (e.g., ASOs comprising SEQ ID NO: 40-43, or a pharmaceutically acceptable salt thereof). In some embodiments of the disclosure, an effective amount of a disclosed polynucleotide complementary to IL-34, or a portion thereof, for example an IL-34 antisense oligonucleotide, may be administered to a patient in need thereof to treat an inflammatory disease, for example, to inhibit inflammatory cytokine production in cells of a patient suffering from an inflammatory disease, and/or to reduce or inhibit an IL-34 mediated inflammatory response. Disclosed herein, in certain embodiments, are methods of treating inflammatory disorders related to IL-34 activities in a patient in need thereof comprising administering to the patient an antisense compound disclosed herein.

"Inflammatory disease" as used herein, refers to a number of acute and chronic inflammatory disorders including but not limited to inflammatory bowel disease, rheumatoid arthritis, psoriasis, osteoarthritis, pouchitis, diabetes (type I and II), tissue or organ rejection, multiple sclerosis, periodontal inflammation (e.g., periodontitis), pigmented villonodular synovitis, hepatitis, sinusitis, colon cancer (e.g., colorectal cancer, colitis-associated colon cancer, sporadic colorectal cancer), coronary artery disease, Sjogren's syndrome (SS), obesity, chronic inflammation, pulmonary sarcoidosis, skin lesions, a CNS inflammatory disease, or an autoimmune disease.

Rheumatoid arthritis (RA) is characterized by chronic, synovial inflammation affecting multiple joints that causes inflammation, swelling, and pain in an around the joints. Left untreated, RA can lead to damage to the cartilage in a joint and bone erosion around the damaged cartilage, and leads to extra-articular lesions. RA can also affect other tissues throughout the body and cause problems in organs such as the skin, mouth, lungs, heart, and eyes. In some embodiments, IL-34 levels are elevated in patients with active RA and in experimental models of inflammatory arthritis.

Provided herein are methods of treating, reducing the risk of developing, or delaying the onset of rheumatoid arthritis in a subject in need thereof comprising administering a disclosed polynucleotide (e.g., a polynucleotide complementary to IL-34, or a portion thereof) or a pharmaceutical composition thereof.

Osteoarthritis (OA) is a degenerative joint disease and is characterized by is a disease of part or the entire joint involving synovial fibrosis and inflammation. OA is associated with clinical symptoms of pain, hyperalgesia, and stiffness. Pathological changes to the synovium can accelerate the progression of OA.

Provided herein are methods of treating, reducing the risk of developing, or delaying the onset of osteoarthritis or synovial fibrosis in a subject in need thereof comprising administering a disclosed polynucleotide (e.g., a polynucleotide complementary to IL-34, or a portion thereof) or a pharmaceutical composition thereof.

In some embodiments, methods of treating skin lesions associated with lupus in a patient in need thereof are provided comprising administering a disclosed polynucleotide or a pharmaceutical composition thereof. In some embodiments, treating skin lesions associated with lupus comprises at least one effect selected from reducing the number of skin lesions, reducing the rate of formation of skin lesions, and reducing the severity of skin lesions. Methods of treating lupus and/or lupus nephritis in a patient suffering therefrom are provided, that include administering a disclosed polynucleotide or a pharmaceutical composition thereof. In some embodiments, methods of slowing the progression of a kidney condition associated with lupus are provided.

Provided herein are methods of treating, reducing the risk of developing, or delaying the onset of a CNS inflammatory disease in a subject in need thereof comprising administering a disclosed polynucleotide (e.g., a polynucleotide complementary to IL-34, or a portion thereof) or a pharmaceutical composition thereof. CNS inflammatory disease that can be treated in this manner include multiple sclerosis, experimental autoimmune encephalomyelitis, Alzheimer's disease, amyotrophic lateral sclerosis (ALS), and Parkinson's disease.

Also provided herein are methods of treating, reducing the risk of developing, or delaying the onset of an autoimmune disease in a subject in need thereof comprising administering a disclosed polynucleotide (e.g., a polynucleotide complementary to IL-34, or a portion thereof) or a pharmaceutical composition thereof. The methods include treating a subject with or at risk of developing an autoimmune disease. Autoimmune diseases that can be treated in this manner include rheumatoid arthritis, osteoarthritis, pouchitis, type I diabetes, asthma, chronic obstructive pulmonary disease (COPD), and idiopathic pulmonary fibrosis.

Inflammatory Bowel Disease

Provided herein, in some embodiments, are methods for treating an inflammatory bowel disease in a patient in need thereof, comprising administering a disclosed polynucleotide (e.g., a polynucleotide complementary to IL-34, or a portion thereof, such as SEQ ID NO: 40-43, or a pharmaceutically acceptable salt thereof) or a pharmaceutical composition thereof. Disclosed herein, in certain embodiments, are methods comprising administering a disclosed compound. "Inflammatory bowel disease," as used herein, refers to a number of chronic inflammatory diseases including Crohn's disease, inflammatory Crohn's disease, fibrostricturing Crohn's disease, gastroduodenal Crohn's disease, Crohn's (granulomatous) colitis, ulcerative colitis, collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, and indeterminate colitis. Crohn's disease and ulcerative colitis are the two most common forms of inflammatory bowel disease. Inflammatory bowel diseases are autoimmune diseases of the digestive system. Crohn's disease may be localized to any portion of the gastrointestinal tract, including the terminal ileum, and may impact all cell types of the gastrointestinal tract. Ulcerative colitis is localized to the colon and rectum, and affects cells of the mucosa only.

Inflammatory Crohn's disease is characterized by abnormal immune response that causes excess gastrointestinal inflammation. Inflammatory Crohn's disease most often affects the intestinal walls, including portions of the small and/or large intestine, for example, the ileum and the colon. Inflammatory Crohn's disease is also associated with development of thick and swollen tissue, as well as ulcers. Mutations in genes that play a role in immune system function (e.g., NOD2, ATG16L1, IL23R, and IRGM) are associated with Crohn's disease, as are genes associated with proper autophagy.

Fibrostricturing Crohn's disease is a form of Crohn's disease that includes the occurrence of fibrostenotic lesions/fibrotic strictures of the gastrointestinal tract. Fibrotic strictures are more often associated with Crohn's disease of the ileum, as opposed to the colon. Inflammation generally precedes the development strictures. Strictures can be associated with any of the following symptoms: abdominal cramping, abdominal pain, abdominal bloating and distension, loss of appetite, fatigue, nausea, vomiting, and constipation. More than 50% of patients that suffer from Crohn's disease experience fibrostenosis.

Fibrotic strictures are associated with cell surface IL-17A receptor expression and increased collagen production, including collagen subtypes I, III, and V. Fibrotic strictures are also associated with co-occurrence of fistulas. Strictures are histologically characterized by the presence of a mixture of inflammatory and mesenchymal cells with deposition of an excess of extracellular matrix (ECM). Activated mesenchymal cells of the intestine accumulate ECM components, including fibronectin and collagen (for example, collagen types III and IV). Disorganized smooth muscle proliferation and excess ECM deposition are believed to modify the mechanical properties of stenotic bowel tissue, resulting in increased stiffness and narrowing of the intestinal tract associated with fibrotic strictures. The presence of fibrotic strictures results in intestinal tissue abnormalities in both the mucosal, submucosal, and muscular layers of the intestinal wall.

In some embodiments the cell is an intestinal cell, for example, an intestinal stromal cell, an intestinal epithelial cell, an intestinal stem cell, a secretory cell, an enterocyte, a Goblet cell, an enteroendocrine cell, a Paneth cell, a transit amplifying cell, a microfold cell, a cup cell, or a tuft cell. In some embodiments, the cell forms part of an intestinal fibrostricture. In the aforementioned embodiments, subject can be a subject in need of treatment of an inflammatory disease or fibrosis, for example, inflammatory Crohn's disease or fibrostricturing Crohn's disease. In some embodiments, methods described herein can be used to inhibit expression of one or more collagens in a cell of a subject, for example, a type I collagen, a type II collagen, a type III collagen, a type IV collagen, a type V collagen, a type VI collagen, a type VII collagen, a type VIII collagen, a type IX collagen, a type X collagen, a type XI collagen, a type XII collagen, a type XIII collagen, a type XIV collagen, a type XV collagen, a type XVI collagen, a type XVII collagen, a type XVIII collagen, a type XIX collagen, a type XX collagen, a type XXI collagen, a type XXII collagen, a type XXIII collagen, a type XXIV collagen, a type XXV collagen, a type XXVI collagen, a type XXVII collagen, a type XXVIII collagen, or a type XXIX collagen. For example, in embodiments described herein, the collagen is COL1A1, COL1A2II, COL2A1, COL3A1, COL4A1, COL4A2, COL4A3, COL4A4, COL4A5, COL4A6, COL5A1, COL5A2, COL5A3, COL6A1, COL6A2, COL6A3, COL6A5, COL7A1, COL8A1, COL8A2, COL9A1, COL9A2, COL9A3, COL10A1, COL11A1, COL11A2, COL12A1, COL13A1, COL14A1, COL15A1, COL16A1, COL17A1, COL18A1, COL19A1, COL20A1, COL21A1, COL22A1, COL23A1, COL24A1, COL25A1, EMID2, COL27A1, COL28A1, or COL29A1. In particular embodiments, the collagen is COL1A1 (collagen 1A), COL3A1 (collagen 3A), or a mixture thereof.

Both environmental and genetic factors are believed to play a role in inflammatory bowel diseases, although the identity of such factors is not well-defined. For example, habitual smoking doubles the risk of developing Crohn's disease. Environmental components may include alterations in flora of the gut which are affected by exposure to ingested foods and medications.

Inflammatory bowel diseases are associated with symptoms including abdominal pain, vomiting, diarrhea, rectal bleeding, severe cramps, muscle spasms, weight loss, malnutrition, fever, anemia, skin lesions, joint pain, eye inflammation, liver disorders, arthritis, pyoderma gangrenosum, primary sclerosing cholangitis, and non-thyroidal illness syndrome, and treating these symptoms using a disclosed antisense compound is also contemplated in an embodiment, for example, treating children suffering from ulcerative colitis who may also suffer from growth defects.

Intestinal Fibrosis

Provided herein, in some embodiments, are methods for treating an intestinal fibrosis in a patient in need thereof, comprising administering a disclosed polynucleotide (e.g., a polynucleotide complementary to IL-34, or a portion thereof, such as SEQ ID NO: 40-43, or a pharmaceutically acceptable salt thereof) or a pharmaceutical composition thereof. Intestinal fibrosis commonly results from the reaction of intestinal tissue to inflammation, such as chronic inflammation caused by inflammatory bowel disease (IBD). In IBD, increased levels of SMAD7 block anti-inflammatory gene expression mediated via TGF-β pathway activation and Smad2/3 phosphorylation. Myofibroblasts exposed to increased TGF-β signaling produce increased amounts of collagen. In the context of Crohn's disease, persistent and chronic inflammation promotes fibrotic processes, resulting in the formation of strictures, including small bowel and colonic strictures.

Intestinal fibrosis can be identified by any of a number of imaging techniques, such as contrast-enhanced ultrasonography. See, e.g., Quaia et al. The value of small bowel wall contrast enhancement after sulfur hexafluoride-filled microbubble injection to differentiate inflammatory from fibrotic strictures in patients with Crohn's disease. *Ultrasound Med. Biol.* 38, 1324-1332 (2012); Nylund et al. Quantitative contrast-enhanced ultrasound comparison between inflammatory and fibrotic lesions in patients with Crohn's disease. *Ultrasound Med. Biol.* 39, 1197-1206 (2013); Stidham et al. Ultrasound elasticity imaging for detecting intestinal fibrosis and inflammation in rats and humans with Crohn's disease. *Gastroenterology* 141, 819-826 (2011). MRI techniques such as magnetization transfer MII can also be used. See, e.g., Maccioni et al. Value of T2-weighted magnetic resonance imaging in the assessment of wall inflammation and fibrosis in Crohn's disease. *Abdom. Imaging* 37, 944-957 (2012); Adler et al. Magnetization transfer helps detect intestinal fibrosis in an animal model of Crohn disease. *Radiology* 259, 127-135 (2011); Pazahr et al. Magnetization transfer for the assessment of bowel fibrosis in patients with Crohn's disease: initial experience. *Magn. Reson. Mat. Phys. Biol. Med.* 26, 291-301 (2013).

Fibrosis

Provided herein, in some embodiments, are methods for treating a fibrosis in a patient in need thereof, comprising administering a disclosed polynucleotide (e.g., a polynucleotide complementary to IL-34, or a portion thereof, such as SEQ ID NO: 40-43, or a pharmaceutically acceptable salt thereof) or a pharmaceutical composition thereof. Disclosed herein, in certain embodiments, are methods of preventing or treating fibrosis, such as hepatic fibrosis, pulmonary fibrosis, synovial fibrosis, and/or intestinal fibrosis, form part of this disclosure. For example, a method of preventing or treating hepatic fibrosis is provided comprising administering to a patient in need thereof a polynucleotide complementary to IL-34, or a portion thereof, disclosed herein. Alternatively, a method of preventing or treating intestinal fibrosis is provided comprising administering to a patient in need thereof a polynucleotide complementary to IL-34, or a portion thereof, disclosed herein. Alternatively, a method of preventing or treating pulmonary fibrosis is provided comprising administering to a patient in need thereof a polynucleotide complementary to IL-34, or a portion thereof, disclosed herein. Alternatively, a method of preventing or treating synovial fibrosis is provided comprising administering to a patient in need thereof a polynucleotide complementary to IL-34, or a portion thereof, disclosed herein.

Patients treated using an above method may or may not have detectable fibrosis. In some embodiments, the patient has at least about a 5%, 10%, 20%, 30%, 40% or even 50% or more reduction in the amount of fibrosis present in the patient after administering an IL-34 antisense oligonucleotide, after e.g., 1 day, 2 days, 1 week, 1 month or 6 months or more. Administering such a polynucleotide complementary to IL-34, or a portion thereof, for example an IL-34 antisense oligonucleotide, may be on, e.g., at least a daily basis. The compound may be administered orally. The delay of clinical manifestation of fibrosis in a patient as a consequence of administering a polynucleotide complementary to IL-34, or a portion thereof, for example an IL-34 antisense oligonucleotide, disclosed here may be at least e.g., 6 months, 1 year, 18 months or even 2 years or more as compared to a patient who is not administered a polynucleotide complementary to IL-34, or a portion thereof, such as one disclosed herein.

A patient in need may have hepatic fibrosis that has developed into cirrhosis. A patient at risk of hepatic fibrosis may include those patients with hepatitis B, hepatitis C or nonalcoholic steatohepatitis (NASH). NASH is included in the spectrum of nonalcoholic fatty liver diseases, including steatosis and cirrhosis. NASH is a component of the metabolic syndrome, which is characterized by obesity, type 2 diabetes mellitus, and dyslipidemia, and can eventually lead to hepatocellular carcinoma.

Methods of treating disorders associated with hepatic fibrosis are also provided, such as the treatment of at least one of: certain storage diseases and inborn errors of metabolism, such as, alpha 1-antitrypsin deficiency, copper storage diseases (e.g., Wilson's disease), fructosemia, galactosemia, glycogen storage diseases (e.g., Types III, IV, VI, IX and X), iron-overload syndromes (e.g., hemochromatosis), lipid abnormalities (e.g. Gaucher's disease), peroxisomal disorders (e.g., Zellweger syndrome), and tyrosinemia; bacterial infections (e.g., brucellosis); parasitic infections (e.g., echinococcosis); NASH; viral infections (e.g., hepatitis B or hepatitis C, including chronic hepatitis B or C); Budd-Chiari syndrome; heart failure; hepatic veno-occlusive disease; and portal vein thrombosis. Methods of treating congenital hepatic fibrosis are also contemplated. The composition may be administered orally.

Abuse of drugs and/or alcohol has been implicated in cases of hepatic fibrosis. Contemplated herein are methods of treating hepatic fibrosis in a patient with a history of drug and/or alcohol abuse. For example, a patient with a history of abusing at least one of the following: alcohol, amiodarone, chlorpromazine, isoniazid, methotrexate, methyldopa, oxyphenisatin and, tolbutamide.

A patient at risk of intestinal fibrosis may include those patients with ulcerative colitis, inflammatory bowel disease, or Crohn's disease. A patient at risk may also include those patients with an early age at diagnosis of Crohn's or colitis, extensive and/or severe of colonic disease, patients with the presence of primary sclerosing cholangitis, and/or patient's having a family history of cancer.

Methods of treating disorders associated with intestinal fibrosis are also provided, such as the treatment of at least one of: ulcerative colitis, an inflammatory bowel disease, or Crohn's disease.

Contemplated herein are methods of preventing or treating renal fibrosis, cardiac fibrosis, endomyocardial fibrosis, idiopathic pulmonary fibrosis, synovial fibrosis, myelofibrosis, retroperitoneal fibrosis, or nephrogenic systemic fibrosis, comprising administering to a patient in need thereof, a pharmaceutical preparation comprising a polynucleotide complementary to IL-34, or a portion thereof, for example an IL-34 antisense oligonucleotide, such as an IL-34 antisense oligonucleotide disclosed herein.

The polynucleotide complementary to IL-34, or a portion thereof, of the invention, including, for example, IL-34 ASOs, can be used alone or in combination with each other whereby at least two polynucleotides complementary to IL-34, or a portion thereof, of the invention are used together in a single composition or as part of a treatment regimen. The polynucleotides complementary to IL-34, or a portion thereof of the invention may also be used in combination with other drugs for treating drug and/or alcohol abuse, renal fibrosis, cardiac fibrosis, endomyocardial fibrosis, idiopathic pulmonary fibrosis, myelofibrosis, retroperitoneal fibrosis, or nephrogenic systemic fibrosis, drug and/or alcohol abuse.

Cancer

Provided herein, in some embodiments, are methods for treating cancer in a patient in need thereof, comprising administering a disclosed polynucleotide (e.g., a polynucleotide complementary to IL-34, or a portion thereof, such as SEQ ID NO: 40-43, or a pharmaceutically acceptable salt thereof) or a pharmaceutical composition thereof. In some embodiments, the cancer may be a primary cancer or a metastatic cancer. In some embodiments, the cancer is any cancer that comprises cells expressing IL-34 at an abnormal level. In some embodiments, the cancer is any cancer that is associated with altered IL-34 expression, e.g., elevated IL-34 expression.

Treatment and Evaluation

A "patient" or "subject" as described herein, refers to any animal at risk for, suffering from or diagnosed for an inflammatory and/or fibrotic disease, including, but not limited to, mammals, primates, and humans. In certain embodiments, the patient may be a non-human mammal such as, for example, a cat, a dog, or a horse. A patient may be an individual diagnosed with a high risk of developing an inflammatory and/or fibrotic disease, someone who has been diagnosed with an inflammatory and/or fibrotic disease, someone who previously suffered from an inflammatory and/or fibrotic disease, or an individual evaluated for symptoms or indications of an inflammatory and/or fibrotic disease, for example, IL-34 expression signal.

A "patient in need," as used herein, refers to a patient suffering from any of the symptoms or manifestations of an inflammatory and/or fibrotic disease, a patient who may suffer from any of the symptoms or manifestations of an inflammatory and/or fibrotic disease, or any patient who might benefit from a method of the disclosure for treating an inflammatory and/or fibrotic disease. A patient in need may include a patient who is diagnosed with a risk of developing an inflammatory and/or fibrotic disease, a patient who has suffered from an inflammatory and/or fibrotic disease in the past, or a patient who has previously been treated for an inflammatory and/or fibrotic disease. Of particular relevance are individuals that suffer from an inflammatory and/or fibrotic disease associated with increased levels of IL-34 expression or activity.

The terms "treat", "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. preventing the disease from increasing in severity or scope; (c) relieving the disease, i.e. causing partial or complete amelioration of the disease; or (d) preventing relapse of the disease, i.e. preventing the disease from returning to an active state following previous successful treatment of symptoms of the disease or treatment of the disease.

An "effective amount" or a "pharmaceutically effective amount," as used herein, refers to the amount of an agent that is sufficient to at least partially treat a condition when administered to a patient. The therapeutically effective amount will vary depending on the severity of the condition, the route of administration of the component, and the age, weight, etc. of the patient being treated. Accordingly, an effective amount of a disclosed IL-34 antisense oligonucleotide is the amount of the IL-34 antisense oligonucleotide necessary to treat an inflammatory and/or fibrotic disease in a patient such that administration of the agent prevents an inflammatory and/or fibrotic disease from occurring in a subject, prevents an inflammatory and/or fibrotic disease progression (e.g., prevents the onset or increased severity of symptoms of inflammatory bowel disease such as rectal bleeding, anemia, or gastrointestinal inflammation), or relieves or completely ameliorates some or all associated symptoms of an inflammatory and/or fibrotic disease, e.g., causes regression of the disease.

Efficacy of treatment may be evaluated by means of evaluation of gross symptoms associated with an inflammatory and/or fibrotic disease, analysis of tissue histology, biochemical assay, imaging methods such as, for example, magnetic resonance imaging, or other known methods. For instance, efficacy of treatment may be evaluated by analyzing gross symptoms of the disease such as changes in abdominal pain, vomiting, diarrhea, rectal bleeding, cramps, muscle spasms, weight loss, malnutrition, fever, anemia or other aspects of gross pathology associated with an inflammatory disease following administration of a disclosed IL-34 antisense oligonucleotide to a patient suffering from an inflammatory disease.

Efficacy of treatment may also be evaluated at the tissue or cellular level, for example, by means of obtaining a tissue biopsy (e.g., a gastrointestinal tissue biopsy) and evaluating gross tissue or cell morphology or staining properties. Biochemical assays that examine protein or RNA expression may also be used to evaluate efficacy of treatment. For instance, one may evaluate IL-34, IL-6, IL-8, TNF-alpha, or levels of another protein or gene product indicative of an inflammatory and/or fibrotic disease, inflammatory cytokine production, or an IL-34 mediated inflammatory response in dissociated cells or non-dissociated tissue via immunocytochemical, immunohistochemical, Western blotting, or Northern blotting methods, or methods useful for evaluating RNA levels such as quantitative or semi-quantitative polymerase chain reaction. One may also evaluate the presence or level of expression of useful biomarkers found in fecal matter, plasma, or serum to evaluate disease state and efficacy of treatment.

In evaluating efficacy of treatment, suitable controls may be chosen to ensure a valid assessment. For instance, one can compare symptoms evaluated in a patient with an inflammatory and/or fibrotic disease following administration of a disclosed polynucleotide complementary to IL-34, or a portion thereof, for example an IL-34 antisense oligonucleotide, to those symptoms in the same patient prior to treatment or at an earlier point in the course of treatment or in another patient not diagnosed with the inflammatory and/or fibrotic disease. Alternatively, one may compare the results of biochemical or histological analysis of gastrointestinal tissue following administration of a disclosed polynucleotide complementary to IL-34, or a portion thereof, for example an IL-34 antisense oligonucleotide, with those of gastrointestinal tissue from the same patient or from an individual not diagnosed with the inflammatory and/or fibrotic disease or from the same patient prior to administration of the polynucleotide complementary to IL-34, or a portion thereof. Additionally, one may compare blood, serum, cell, or fecal samples following administration of the polynucleotide complementary to IL-34, or a portion thereof, for example an IL-34 antisense oligonucleotide, with comparable samples from an individual not diagnosed with the inflammatory and/or fibrotic disease or from the same patient prior to administration of the polynucleotide complementary to IL-34, or a portion thereof.

Validation of IL-34 inhibition may be determined by direct or indirect assessment of IL-34 expression levels or activity. For instance, biochemical assays that measure IL-34 protein or RNA expression may be used to evaluate overall IL-34 inhibition. For instance, one may measure IL-34 protein levels in gastrointestinal tissue by Western blot to evaluate overall IL-34 levels. One may also measure IL-34 mRNA levels by means of Northern blot or quantitative polymerase chain reaction to determine overall IL-34 inhibition. One may also evaluate IL-34 protein levels or levels of another protein indicative of IL-34 signaling activity in dissociated cells, non-dissociated tissue, blood, serum, or fecal matter via immunocytochemical or immunohistochemical methods.

IL-34 inhibition may also be evaluated indirectly by measuring parameters such as macrophage or monocyte generation or proliferation, or measuring alterations in other parameters correlated with changes in IL-34 activity, including MAP kinase phosphorylation and other indicators of signaling activation of the IL-34 receptor—the macrophage colony stimulating factor receptor (M-CSFR-1, also known as MCSFR-1, M-CSFR1, and CSF1R). For instance, one may measure levels of active MAPK1 or MAPK3 phosphorylation in cells of a patient treated with a disclosed polynucleotide complementary to IL-34, or a portion thereof, for example an IL-34 antisense oligonucleotide, as an indication of IL-34 activity in the cells. One may also evaluate the presence or level of expression of useful biomarkers found in plasma, blood, fecal matter or tissue to evaluate efficacy of IL-34 inhibition.

Methods of treatment disclosed herein include methods of inhibiting inflammatory cytokine production. "Inflammatory cytokine production" refers to the expression of cytokines that initiate and/or promote an inflammatory cytokine response. An "inflammatory cytokine response" refers to an immune response that may be characterized by granulocyte recruitment, lymphocyte recruitment, systemic inflammation (especially of the gastrointestinal tract or a portion or portions thereof), fever, tissue destruction, shock, and/or death. An inflammatory cytokine response may be characterized by binding of individual cytokines to their cognate cell surface receptor (e.g., IL-34 binding to CSF1R) and subsequent cascades of intracellular signaling that alter cell functions and gene expression. Inflammatory cytokines include, but are not limited to IL-1, IL-6, IL-8, IL-34, and TNF-alpha. Expression of inflammatory cytokines may occur in, for example, macrophages, monocytes, propia lamina mononuclear cells, or other cells of the gastrointestinal tract or cells of the immune system. Methods of inhibiting inflammatory cytokine production include methods that reduce expression levels of some or all inflammatory cytokines in a patient suffering from an inflammatory disease. Methods of inhibiting inflammatory cytokine production also include methods that reduce expression levels of some or all inflammatory cytokines in cells of a patient suffering from an inflammatory disease.

Methods of the disclosure for inhibiting inflammatory cytokine production include methods of reducing or inhibiting an IL-34 mediated inflammatory response. An "IL-34 mediated inflammatory response," as used herein, refers to an inflammatory response initiated, facilitated, or promoted by IL-34 expression or IL-34 signaling activity. An IL-34 mediated inflammatory response may result in expression of inflammatory cytokines including, but not limited to, IL-34, IL-6, IL-8, or TNF-alpha, and activation of inflammatory cytokine signaling. Additionally, an IL-34 mediated inflammatory response may be characterized by granulocyte recruitment, lymphocyte recruitment, systemic inflammation (especially of the gastrointestinal tract or a portion or portions thereof), fever, tissue destruction, shock, and/or death. An IL-34 mediated inflammatory response may also be characterized by activation of IL-34 signaling, for instance, binding of IL-34 to CSF1R and phosphorylation of downstream MAP kinases. Reducing or inhibiting an IL-34 mediated inflammatory response refers to alleviating any or all of the cellular and systemic changes associated with an IL-34 mediated inflammatory response. For example, a reduction in inflammatory cytokine production, immune cell recruitment, or tissue inflammation would indicate reducing or inhibiting of an IL-34 mediated inflammatory response.

The disclosure also provides methods of inhibiting IL-34 in cells of a patient suffering from an inflammatory and/or fibrotic disease. IL-34 may be inhibited in any cell in which IL-34 expression or activity occurs, including cells of the gastrointestinal tract, immune system, and blood. Cells of the gastrointestinal tract (including cells of the intestinal wall, the stomach, duodenum, jejunum, large intestine, small intestine, ileum, colon, rectum and anal canal), include columnar epithelial cells, intestinal stromal cells, mucosal epithelial cells, zymogenic cells, neck mucus cells, parietal cells, gastrin cells, Goblet cells, Paneth cells, oligomucus cells, and villus absorptive cells. Cells of the immune system include leukocytes, phagocytes (e.g., macrophages, neutrophils, and dendritic cells), monocytes, mast cells, eosinophils, basophils, natural killer cells, innate cells, lymphocytes, B cells, and T cells. Blood cells include red blood cells (erythrocytes) and white blood cells (leukocytes, monocytes, and platelets).

Pharmaceutical Compositions and Routes of Administration

Provided herein, in some embodiments, are pharmaceutical compositions comprising polynucleotides complementary to IL-34, or a portion thereof, disclosed herein, or a pharmaceutically acceptable salt thereof, and/or a pharmaceutically acceptable excipient.

In some embodiments, the polynucleotide is an IL-34 antisense oligonucleotide (ASO). In some embodiments, the IL-34 ASO is a gapmer ASO. In some embodiments, the IL-34 ASO gapmer includes one or more 2'-MOE nucleosides. In some embodiments, the sequence of the IL-34 ASO is selected from one of the following:

5'-CxTxTxTxGGGCXGCACCAGCxTxTxCx-3' (SEQ ID NO: 40), wherein Cx is 2'-O-(2-methoxyethyl) cytidine, Tx is 2'-O-(2-methoxyethyl)thymidine, and X is 5-methylcytidine;

5'-CxTxTxTGGGCXGCACCAGCTxTxCx-3' (SEQ ID NO: 41), wherein Cx is 2'-O-(2-methoxyethyl)cytidine, Tx is 2'-O-(2-methoxyethyl)thymidine, and X is 5-methylcytidine;

5'-TxCxCxAxTGACCXGGAAGCAxGxTxTx-3' (SEQ ID NO: 42), wherein Cx is 2'-O-(2-methoxyethyl) cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; and 5'-TxCxCxATGACCXGGAAGCAGxTxTx-3' (SEQ ID NO: 43), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine.

As used herein the term "pharmaceutical composition" means, for example, a mixture containing a specified amount of a therapeutic compound, e.g., a therapeutically effective amount, of a therapeutic compound in a pharmaceutically acceptable excipient to be administered to a mammal, e.g., a human, in order to treat an inflammatory and/or fibrotic disease.

In some embodiments, a disclosed pharmaceutical composition is useful for treating or preventing an inflammatory disease (e.g., rheumatoid arthritis or osteoarthritis). In some embodiments, a disclosed pharmaceutical composition is useful for treating or preventing a fibrotic disease. In some embodiments, a disclosed pharmaceutical composition is useful for treating or preventing a cancer.

As used herein, "pharmaceutically acceptable excipient" refers to a substance that aids the administration of an active agent to and/or absorption by a subject and can be included in the compositions of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with polynucleotide complementary to IL-34, or a portion thereof, of the invention. For examples of excipients, see Martin, Remington's Pharmaceutical Sciences, 15th Ed., Mack Publ. Co., Easton, PA (1975).

In one embodiment, a disclosed polynucleotide or a pharmaceutical composition thereof may be administered by one or several routes, including intraarticularly, rectally, topically, parenterally, orally, pulmonarily, intratracheally, intranasally, transdermally, or intraduodenally. The term parenteral as used herein includes subcutaneous injections, intrapancreatic administration, intravenous, intramuscular, intraperitoneal, intrasternal injection or infusion techniques. In some embodiments, a disclosed polynucleotide or a pharmaceutical composition thereof is administered intraarticularly. In some embodiments, a disclosed polynucleotide or a pharmaceutical composition thereof is administered rectally. In some embodiments, a disclosed polynucleotide or a pharmaceutical composition thereof is administered subcutaneously. In some embodiments, a disclosed polynucleotide or a pharmaceutical composition thereof is administered orally. In some embodiments, a disclosed polynucleotide or a pharmaceutical composition thereof may be administered directly to the gastrointestinal system, or specific regions of the gastrointestinal system (e.g., the ileum, colon, or rectum) via parenteral administration.

Pharmaceutical compositions containing a polynucleotide complementary to IL-34, or a portion thereof, disclosed herein, can be presented in a dosage unit form and can be prepared by any suitable method. A pharmaceutical composition should be formulated to be compatible with its intended route of administration. Useful formulations can be prepared by methods well known in the pharmaceutical art. For example, see Remington's Pharmaceutical Sciences, 18th ed. (Mack Publishing Company, 1990).

Pharmaceutical formulations, for example, are sterile. Sterilization can be accomplished, for example, by filtration through sterile filtration membranes. Where the composition is lyophilized, filter sterilization can be conducted prior to or following lyophilization and reconstitution.

Parenteral Administration

The pharmaceutical compositions of the disclosure can be formulated for parenteral administration, e.g., formulated for injection via the intravenous, intramuscular, subcutaneous, intralesional, or intraperitoneal routes. The preparation of an aqueous composition, such as an aqueous pharmaceutical composition containing a disclosed polynucleotide complementary to IL-34, or a portion thereof, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In addition, sterile, fixed oils may be employed as a solvent or suspending medium. For this purpose, any bland fixed oil can be employed including synthetic mono- or diglycerides. In addition, fatty acids such as oleic acid can be used in the preparation of injectables. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In one embodiment, a disclosed polynucleotide complementary to IL-34, or a portion thereof, may be suspended in a carrier or excipient fluid comprising 1% (w/v) sodium carboxymethylcellulose and 0.1% (v/v) TWEEN™ 80. Under ordinary conditions of storage and use, these preparations contain a preservative to prevent the growth of microorganisms.

Injectable preparations, for example, sterile injectable aqueous or oleaginous suspensions may be formulated according to the known art using suitable dispersing or wetting agents and suspending agents. Generally, dispersions are prepared by incorporating the various sterilized active ingredients into a sterile vehicle which contains the basic dispersion medium and the required other ingredients from those enumerated above. Sterile injectable solutions of the disclosure may be prepared by incorporating a disclosed polynucleotide complementary to IL-34, or a portion thereof, for example an IL-34 antisense oligonucleotide, in the required amount of the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The injectable formulations can be sterilized, for example, by filtration through a bacteria-retaining filter.

The preparation of more, or highly concentrated solutions for intramuscular injection is also contemplated. In this regard, the use of DMSO as solvent is preferred as this will result in extremely rapid penetration, delivering high concentrations of the disclosed IL-34 antisense oligonucleotide to a small area.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium 10 carbonate, sodium acetate, sodium biphosphate and the like, in amounts sufficient to maintain the pH at between about pH 6 and pH 8, and for example, between about pH 7 and pH 7.5. Suitable tonicity agents are dextran 40, dextran 70, dextrose, glycerin, potassium chloride, propylene glycol, sodium chloride, and the like, such that the sodium chloride equivalent of the solution is in the range 0.9 plus or minus 0.2%. Suitable antioxidants and stabilizers include sodium bisulfate, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

Oral Administration

In some embodiments, contemplated herein are compositions suitable for oral delivery of a disclosed polynucleotide complementary to IL-34, or a portion thereof, e.g., tablets that include an enteric coating, e.g., a gastro-resistant coating, such that the compositions may deliver the polynucleotide to, e.g., the gastrointestinal tract of a patient. For example, such administration may result in a topical effect, substantially topically applying the polynucleotide complementary to IL-34, or a portion thereof, directly to an affected portion of the gastrointestinal tract of a patient. Such administration, may, in some embodiments, substantially avoid unwanted systemic absorption of the polynucleotide complementary to IL-34, or a portion thereof.

For example, a tablet for oral administration is provided that comprises granules (e.g., is at least partially formed from granules) that include a disclosed polynucleotide complementary to IL-34, or a portion thereof, for example an IL-34 antisense oligonucleotide, e.g., an antisense oligonucleotide that includes the nucleotide sequence of any one of SEQ ID NOs: 1-23 or SEQ ID NOs: 40-43, and pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a disclosed polynucleotide complementary to IL-34, or a portion thereof, for example an IL-34 antisense oligonucleotide, e.g., an antisense oligonucleotide that includes the nucleotide sequence of any one of SEQ ID NOs: 1-23 or SEQ ID NOs: 40-43, and a pharmaceutically acceptable salt, and a pharmaceutically acceptable filler. For example, a disclosed polynucleotide complementary to IL-34, or a portion thereof, for example an IL-34 antisense oligonucleotide, and a filler may be blended together, optionally, with other excipients, and formed into granules. In some embodiments, the intragranular phase may be formed using wet granulation, e.g., a liquid (e.g., water) is added to the blended polynucleotide complementary to IL-34, or a portion thereof, and filler, and then the combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

A disclosed formulation may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pre-gelatinized starch, calcium carbonate, and others including combinations thereof.

In some embodiments, a disclosed formulation may include an intragranular phase and/or a extragranular phase that includes a binder, which may generally function to hold the ingredients of the pharmaceutical formulation together. Exemplary binders of the disclosure may include, but are not limited to, the following: starches, sugars, cellulose or modified cellulose such as hydroxypropyl cellulose, lactose, pre-gelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated formulation includes an intra-granular phase comprising a disclosed polynucleotide complementary to IL-34, or a portion thereof, for example an IL-34 antisense oligonucleotide, and excipients chosen from: mannitol, microcrystalline cellulose, hydroxypropylmethyl cellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated formulation may include a lubricant, e.g., an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive track. Enteric coatings may include a polymer that disintegrates at different rates according to pH. Enteric coatings may include for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

Exemplary enteric coatings include Opadry® AMB, Acryl-EZE®, Eudragit® grades. In some embodiments, an enteric coating may comprise about 5% to about 10%, about 5% to about 20%, 8 to about 15%, about 8% to about 20%, about 10% to about 20%, or about 12 to about 20%, or about 18% of a contemplated tablet by weight. For example, enteric coatings may include an ethylacrylate-methacrylic acid copolymer.

For example, in a contemplated embodiment, a tablet is provided that comprises or consists essentially of about 0.5% to about 70%, e.g., about 0.5% to about 10%, or about 1% to about 20%, by weight of a disclosed polynucleotide complementary to IL-34, or a portion thereof, for example an IL-34 antisense oligonucleotide, or a pharmaceutically acceptable salt thereof. Such a tablet may include for example, about 0.5% to about 60% by weight of mannitol, e.g., about 30% to about 50% by weight mannitol, e.g., about 40% by weight mannitol; and/or about 20% to about 40% by weight of microcrystalline cellulose, or about 10% to about 30% by weight of microcrystalline cellulose. For example, a disclosed tablet may comprise an intragranular phase that includes about 30% to about 60%, e.g. about 45% to about 65% by weight, or alternatively, about 5 to about 10% by weight of a disclosed polynucleotide complementary to IL-34, or a portion thereof, for example an IL-34 antisense oligonucleotide, about 30% to about 50%, or alternatively, about 5% to about 15% by weight mannitol, about 5% to about 15% microcrystalline cellulose, about 0% to about 4%, or about 1% to about 7% hydroxypropylmethylcellulose, and about 0% to about 4%, e.g. about 2% to about 4% sodium starch glycolate by weight.

In another contemplated embodiment, a pharmaceutical tablet formulation for oral administration of a disclosed polynucleotide complementary to IL-34, or a portion thereof, for example an IL-34 antisense oligonucleotide, comprises an intra-granular phase, wherein the intra-granular phase includes a disclosed polynucleotide complementary to IL-34, or a portion thereof, or a pharmaceutically acceptable salt thereof (such as a sodium salt), and a pharmaceutically acceptable filler, and which may also include an extra-granular phase, that may include a pharmaceutically acceptable excipient such as a disintegrant. The extra-granular phase may include components chosen from microcrystalline cellulose, magnesium stearate, and mixtures thereof. The pharmaceutical composition may also include an enteric coating of about 12% to 20% by weight of the tablet. For example, a pharmaceutically acceptable tablet for oral use may comprise about 0.5% to 10% by weight of a disclosed polynucleotide complementary to IL-34, or a portion thereof, for example an IL-34 antisense oligonucleotide, or a pharmaceutically acceptable salt thereof, about 30% to 50% by weight mannitol, about 10% to 30% by weight microcrystalline cellulose, and an enteric coating comprising an ethylacrylate-methacrylic acid copolymer.

In another example, a pharmaceutically acceptable tablet for oral use may comprise an intra-granular phase, comprising about 5 to about 10% by weight of a disclosed polynucleotide complementary to IL-34, or a portion thereof, for example an IL-34 antisense oligonucleotide, or a pharmaceutically acceptable salt thereof, about 40% by weight mannitol, about 8% by weight microcrystalline cellulose, about 5% by weight hydroxypropylmethyl cellulose, and about 2% by weight sodium starch glycolate; an extra-granular phase comprising about 17% by weight microcrystalline cellulose, about 2% by weight sodium starch glycolate, about 0.4% by weight magnesium stearate; and an enteric coating over the tablet comprising an ethylacrylate-methacrylic acid copolymer.

In some embodiments the pharmaceutical composition may contain an enteric coating comprising about 13% or about 15%, 16%, 17% or 18% by weight, e.g., AcyrlEZE® (see, e.g., PCT Publication No. WO2010/054826, which is hereby incorporated by reference in its entirety).

The rate at which point the coating dissolves and the active ingredient is released is its dissolution rate. In an embodiment, a contemplated tablet may have a dissolution profile, e.g., when tested in a USP/EP Type 2 apparatus (paddle) at 100 rpm and 37° C. in a phosphate buffer with a pH of 7.2, of about 50% to about 100% of the polynucleotide complementary to IL-34, or a portion thereof, releasing after about 120 minutes to about 240 minutes, for example after 180 minutes. In another embodiment, a contemplated tablet may have a dissolution profile, e.g., when tested in a USP/EP Type 2 apparatus (paddle) at 100 rpm and 37° C. in diluted HCl with a pH of 1.0, where substantially none of the polynucleotide complementary to IL-34, or a portion thereof, is released after 120 minutes. A contemplated tablet, in another embodiment, may have a dissolution profile, e.g., when tested in USP/EP Type 2 apparatus (paddle) at 100 rpm and 37° C. in a phosphate buffer with a pH of 6.6, of about 10% to about 30%, or not more than about 50%, of the polynucleotide complementary to IL-34, or a portion thereof, releasing after 30 minutes.

Contemplated formulations, e.g., tablets, in some embodiments, when orally administered to the patient may result in minimal plasma concentration of the polynucleotide complementary to IL-34, or a portion thereof, for example an IL-34 antisense oligonucleotide, in the patient. In another embodiment, disclosed formulations, when orally administered to a patient, topically deliver to the colon or rectum of a patient, e.g., to an affected or diseased site of a patient.

In some embodiments, methods provided herein may further include administering at least one other agent that is directed to treatment of diseases and disorders disclosed herein. In one embodiment, contemplated other agents may be co-administered (e.g., sequentially or simultaneously).

Agents contemplated include immunosuppressive agents including glucocorticoids, cytostatics, antibodies, agents acting on immunophilins, interferons, opioids, TNF binding proteins, mycophenolate, and small biological agents. For example, contemplated immunosuppressive agents include, but are not limited to: tacrolimus, cyclosporine, pimecrolimus, sirolimus, everolimus, mycophenolic acid, fingolimod, dexamethasone, fludarabine, cyclophosphamide, methotrexate, azathioprine, leflunomide, teriflunomide, anakinra, antithymocyte globulin, anti-lymphocyte globulin, muromonab-CD3, afutuzumab, rituximab, teplizumab, efalizumab, daclizumab, basiliximab, adalimumab, infliximab, certolizumab pegol, natalizumab, and etanercept. Other contemplated agents include antibiotics, anti-diarrheals, laxatives, pain relievers, iron supplements, and calcium or vitamin D or B-12 supplements.

Dosage and Frequency of Administration

Provided herein, in some embodiments, are exemplary dosages of pharmaceutical compositions for use in treating fibrosis, for example pulmonary fibrosis, synovial fibrosis, or intestinal fibrosis in a patient in need thereof, comprising administering a polynucleotide complementary to IL-34, or a portion thereof, for example an IL-34 antisense composition (e.g., ASOs comprising SEQ ID NO: 40-43, or a pharmaceutically acceptable salt thereof). Exemplary formulations include dosage forms that include or consist essentially of about 35 mg to about 500 mg of a disclosed polynucleotide complementary to IL-34, or a portion thereof, for example an IL-34 antisense oligonucleotide. For example, formulations that include about 35 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg of a disclosed polynucleotide complementary to IL-34, or a portion thereof, for example an IL-34 antisense oligonucleotide, are contemplated herein. In one embodiment, a formulation may include about 40 mg, 80 mg, or 160 mg of a disclosed polynucleotide complementary to IL-34, or a portion thereof, for example an IL-34 antisense oligonucleotide. In some embodiments, a formulation may include at least 100 μg of a disclosed polynucleotide complementary to IL-34, or a portion thereof, for example an IL-34 antisense oligonucleotide. For example, formulations may include about 0.1 mg, 0.2 mg, 0.3 mg, 0.4 mg, 0.5 mg, 1 mg, 5 mg, 10 mg, 15 mg, 20 mg, or 25 mg of a disclosed polynucleotide complementary to IL-34, or a portion thereof, for example an IL-34 antisense oligonucleotide. The amount administered will depend on variables such as the type and extent of disease or indication to be treated, the overall health and size of the patient, the in vivo potency of the polynucleotide complementary to IL-34, or a portion thereof, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 40 mg to 160 mg. Dosing frequency can vary, depending on factors such as route of administration, dosage amount and the disease being treated. Exemplary dosing frequencies are once per day, once per week and once every two weeks. In some embodiments, dosing is once per day for 7 days.

Diagnostic Methods

The disclosure also provides a method of diagnosing a patient with an inflammatory and/or fibrotic disease that relies upon detecting levels of IL-34 expression signal in one or more biological samples of a patient. As used herein, the term "IL-34 expression signal" can refer to any indication of IL-34 gene expression, or gene or gene product activity. IL-34 gene products include RNA (e.g., mRNA), peptides, and proteins. Indices of IL-34 gene expression that can be assessed include, but are not limited to, IL-34 gene or chromatin state, IL-34 gene interaction with cellular components that regulate gene expression, IL-34 gene product expression levels (e.g., IL-34 RNA expression levels, IL-34 protein expression levels), or interaction of IL-34 RNA or protein with transcriptional, translational, or post-translational processing machinery. Indices of IL-34 gene product activity include, but are not limited to, assessment of IL-34 signaling activity (e.g., assessment of CSF1R activation or MAPK1/MAPK3 phosphorylation) and assessment of IL-34 receptor binding (e.g., CSF1R binding).

Detection of IL-34 expression signal may be accomplished through in vivo, in vitro, or ex vivo methods. In a preferred embodiment, methods of the disclosure may be carried out in vitro. Methods of detecting may involve detection in blood, serum, fecal matter, tissue, or cells of a patient. Detection may be achieved by measuring IL-34 expression signal in whole tissue, tissue explants, cell cultures, dissociated cells, cell extract, or body fluids, including blood or serum. Contemplated methods of detection include assays that measure levels of IL-34 gene product expression such as Western blotting, FACS, ELISA, other quantitative binding assays, cell or tissue growth assays, Northern blots, quantitative or semi-quantitative polymerase chain reaction, medical imaging methods (e.g., MRI), or immunostaining methods (e.g., immunohistochemistry or immunocytochemistry).

LISTING OF EXEMPLARY EMBODIMENTS

The invention is further described by the following non-limiting exemplary embodiments:

Embodiment 1. A polynucleotide, comprising a nucleotide sequence according to:

```
a.
                                    (SEQ ID NO: 3)
5'-CTTTGGGCCGCACCAGCTTC-3',
or b.
                                    (SEQ ID NO: 5)
5'-TCCATGACCCGGAAGCAGTT-3',
``` wherein at least one cytidine of the nucleotide sequence is chemically modified, and at least one nucleoside is a 2'-O-(2-methoxyethyl) (2'-MOE) nucleoside;

or a pharmaceutically acceptable salt thereof.

Embodiment 2. The polynucleotide of embodiment 1, wherein no more than 10 nucleosides are chemically modified.

Embodiment 3. The polynucleotide of embodiment 1 or 2, comprising six 2'-MOE nucleosides.

Embodiment 4. The polynucleotide of embodiment 1 or 2, comprising eight 2'-MOE nucleosides.

Embodiment 5. The polynucleotide of any one of embodiments 1-4, comprising a nucleotide sequence selected from the group consisting of:
- a. 5'-CxTxTxTxGGGCXGCACCAGCxTxTxCx-3' (SEQ ID NO: 40), wherein Cx is 2'-O-(2-methoxyethyl) cytidine, Tx is 2'-O-(2-methoxyethyl)thymidine, and X is 5-methylcytidine;
- b. 5'-CxTxTxTGGGCXGCACCAGCTxTxCx-3' (SEQ ID NO: 41), wherein Cx is 2'-O-(2-methoxyethyl) cytidine, Tx is 2'-O-(2-methoxyethyl)thymidine, and X is 5-methylcytidine;
- c. 5'-TxCxCxAxTGACCXGGAAGCAxGxTxTx-3' (SEQ ID NO: 42), wherein Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; and
- d. 5'-TxCxCxATGACCXGGAAGCAGxIxIx-3' (SEQ ID NO: 43), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine;

or a pharmaceutically acceptable salt thereof.

Embodiment 6. The polynucleotide of any one of embodiments 1-5, wherein the polynucleotide is complementary to IL-34.

Embodiment 7. The polynucleotide of any one of embodiments 1-6, wherein the polynucleotide is an IL-34 antisense oligonucleotide.

Embodiment 8. The polynucleotide of any one of embodiments 1-7, wherein the polynucleotide is an IL-34 siRNA.

Embodiment 9. The polynucleotide of any one of embodiments 1-8, wherein at least one internucleoside linkage of the polynucleotide is selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, and an aminoalkylphosphoramidate linkage, a thiophosphoramidate linkage, thionoalkylphosphonate linkage, a thionoalkylphosphotriester linkage, a thiophosphate linkage, a selenophosphate linkage, and a boranophosphate linkage.

Embodiment 10. The polynucleotide of embodiment 9, wherein at least one internucleoside linkage of the polynucleotide is a phosphorothioate linkage.

Embodiment 11. The polynucleotide of any one of embodiments 1-10, wherein all internucleoside linkages of the polynucleotide are phosphorothioate linkages.

Embodiment 12. The polynucleotide of any one of embodiments 1-11, wherein the polynucleotide is 20, 21, 22, 23, 24, 25, 26, 27, 28, 29, or 30 nucleotides in length.

Embodiment 13. The polynucleotide of any one of embodiments 1-11, wherein the polynucleotide is 20 nucleotides in length or 20-25, 20-30, 20-35, 25-30, 25-35, or 30-35 nucleotides in length.

Embodiment 14. The polynucleotide of any one of embodiments 1-13, wherein the polynucleotide is no more than 20, 25, or 30 nucleotides in length.

Embodiment 15. The polynucleotide of any one of embodiments 1-13, wherein the polynucleotide is from 20 to 25 nucleotides in length.

Embodiment 16. The polynucleotide of any one of embodiments 1-13, wherein the polynucleotide is 20 nucleotides in length.

Embodiment 17. A pharmaceutical composition, comprising (a) a polynucleotide of any one of embodiments 1-16, or a pharmaceutically acceptable salt thereof, and (b) a pharmaceutically acceptable excipient.

Embodiment 18. The pharmaceutical composition of embodiment 17, wherein the pharmaceutical composition is suitable for topical, parenteral, oral, pulmonary, intratracheal, intranasal, transdermal, or intraduodenal administration.

Embodiment 19. A method of treating an inflammatory disease in a patient in need thereof, the method comprising administering to the patient in need thereof an effective amount of a polynucleotide of any one of embodiments 1-16, or a pharmaceutically acceptable salt thereof, or a pharmaceutical composition of any one of embodiments 17-18.

Embodiment 20. The method of embodiment 19, wherein the inflammatory disease is associated with altered IL-34 expression.

Embodiment 21. The method of embodiment 19 or 20, wherein the inflammatory disease is associated with elevated IL-34 expression.

Embodiment 22. The method any one of embodiments 19-21, wherein the inflammatory disease is rheumatoid arthritis.

Embodiment 23. The method any one of embodiments 19-21, wherein the inflammatory disease is osteoarthritis.

Embodiment 24. The method of any one of embodiments 19-23, wherein the method inhibits inflammatory cytokine production in cells of the patient.

Embodiment 25. The method of any one of embodiments 19-24, wherein the method reduces or inhibits an IL-34 mediated inflammatory response in cells of the patient.

Embodiment 26. The method of any one of embodiments 19-25, wherein the method reduces or inhibits IL-34-mediated macrophage colony-stimulating factor receptor (M-CSFR-1) signaling in cells of the patient.

Embodiment 27. The method of any one of embodiments 24-26, wherein the cell is an intestinal cell.

Embodiment 28. The method of any one of embodiments 24-26, wherein the cell is an intestinal stromal cell.

Embodiment 29. The method of any one of embodiments 24-26, wherein the cell forms part of an intestinal fibrostricture.

Embodiment 30. A method of reducing or eliminating a fibrotic stricture in a patient suffering from an inflammatory disease, the method comprising administering an effective amount of a polynucleotide of any one of embodiments 1-16, or a pharmaceutically acceptable salt thereof, or a pharmaceutical composition of any one of embodiments 17-18.

Embodiment 31. The method of embodiment 27, wherein the fibrotic stricture is located in the intestine.

Embodiment 32. The method of embodiment 30 or 31, wherein the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, Sjogren's syndrome (SS), obesity, chronic inflammation, pulmonary sarcoidosis, skin lesions, a CNS inflammatory disease, and an autoimmune disease.

Embodiment 33. The method of embodiment 32, wherein the inflammatory disease is a rheumatoid arthritis.

Embodiment 34. The method of embodiment 32, wherein the inflammatory disease is an osteoarthritis.

Embodiment 35. The method of embodiment 32, wherein the inflammatory disease is an inflammatory bowel disease.

Embodiment 36. The method of embodiment 32, wherein the inflammatory bowel disease is selected from the group consisting of Crohn's disease, gastroduodenal Crohn's disease, Crohn's (granulomatous) colitis, inflammatory Crohn's disease, fibrostricturing Crohn's disease, ulcerative colitis, collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, and indeterminate colitis.

Embodiment 37. The method of embodiment 30, wherein the inflammatory bowel disease is inflammatory Crohn's disease.

Embodiment 38. The method of embodiment 30, wherein the inflammatory bowel disease is fibrostricturing Crohn's disease.

Embodiment 39. A method for preventing or treating fibrosis, the method comprising administering to a patient in need thereof a therapeutically effective amount of a polynucleotide of any one of embodiments 1-16, or a pharmaceutically acceptable salt thereof, or a pharmaceutical composition of any one of embodiments 17-18.

Embodiment 40. The method of embodiment 39, wherein the fibrosis is intestinal fibrosis.

Embodiment 41. The method of embodiment 39, wherein the fibrosis is pulmonary fibrosis.

Embodiment 42. The method of embodiment 39, wherein the fibrosis is synovial fibrosis.

Embodiment 43. The method of embodiment 39, wherein the fibrosis is selected from the group consisting of renal fibrosis, cardiac fibrosis, endomyocardial fibrosis, myelofibrosis, retroperitoneal fibrosis, and nephrogenic systemic fibrosis.

Embodiment 44. The method of any one of embodiments 39-43, wherein the patient is suffering from rheumatoid arthritis.

Embodiment 45. The method of any one of embodiments 39-43, wherein the patient is suffering from osteoarthritis.

Embodiment 46. The method of any one of embodiments 39-43, wherein the patient is suffering from Crohn's disease.

Embodiment 47. The method of any one of embodiments 19-46, wherein the polynucleotide is administered intraarticularly, rectally, topically, parenterally, orally, pulmonarily, intratracheally, intranasally, transdermally, or intraduodenally.

Embodiment 48. The method of embodiment 47, wherein the polynucleotide is administered intraarticularly.

Embodiment 49. The method of embodiment 47, wherein the polynucleotide is administered rectally.

Embodiment 50. The method of embodiment 47, wherein the polynucleotide is administered orally.

Embodiment 51. Use of a polynucleotide of any one of embodiments 1-17, or a pharmaceutically acceptable salt thereof, in the manufacture of a medicament for treating an inflammatory disease.

Embodiment 52. The use of embodiment 51, wherein the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, or Sjogren's syndrome (SS), obesity, chronic inflammation, pulmonary sarcoidosis, skin lesions, a CNS inflammatory disease, and an autoimmune disease.

Embodiment 53. The use of any one of embodiments 51-52, wherein the patient is suffering from rheumatoid arthritis.

Embodiment 54. The use of any one of embodiments 51-52, wherein the patient is suffering from osteoarthritis.

Embodiment 55. The use of any one of embodiments 51-52, wherein the patient is suffering from Crohn's disease.

Embodiment 56. The use of embodiment 52, wherein the inflammatory disease is an inflammatory bowel disease.

Embodiment 57. The use of embodiment 56, wherein the inflammatory bowel disease is selected from the group consisting of Crohn's disease, inflammatory Crohn's disease, fibrostricturing Crohn's disease, gastroduodenal Crohn's disease, Crohn's (granulomatous) colitis, ulcerative colitis, collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, and indeterminate colitis.

Embodiment 58. The use of embodiment 57, wherein the inflammatory bowel disease is inflammatory Crohn's disease.

Embodiment 59. The use of embodiment 57, wherein the inflammatory bowel disease is fibrostricturing Crohn's disease.

Embodiment 60. A polynucleotide of any one of embodiments 1-17, or a pharmaceutically-acceptable salt thereof, for use as a medicament.

Embodiment 61. The polynucleotide of embodiment 60 for use in treating an inflammatory disease in a patient in need thereof.

Embodiment 62. The polynucleotide of embodiment 61, wherein the inflammatory disease is rheumatoid arthritis or osteoarthritis.

Embodiment 63. A polynucleotide of any one of embodiments 1-17, or a pharmaceutically-acceptable salt thereof, for use in the treatment of an inflammatory disease.

Embodiment 64. The polynucleotide for use as embodied in embodiment 63, wherein the inflammatory disease is selected from the group consisting of an inflammatory bowel disease, rheumatoid arthritis, psoriasis, osteoarthritis, pouchitis, diabetes (type I and II), tissue or organ rejection, multiple sclerosis, periodontal inflammation, periodontitis, pigmented villonodular synovitis, hepatitis, sinusitis, colon cancer, colorectal cancer, colitis-associated colon cancer, sporadic colorectal cancer, coronary artery disease, or Sjogren's syndrome (SS), obesity, chronic inflammation, pulmonary sarcoidosis, skin lesions, a CNS inflammatory disease, and an autoimmune disease.

Embodiment 65. The polynucleotide for use as embodied in embodiment 64, wherein the inflammatory disease is rheumatoid arthritis.

Embodiment 66. The polynucleotide for use as embodied in embodiment 64, wherein the inflammatory disease is osteoarthritis.

Embodiment 67. The polynucleotide for use as embodied in embodiment 64, wherein the inflammatory disease is an inflammatory bowel disease.

Embodiment 68. The polynucleotide for use as embodied in embodiment 67, wherein the inflammatory bowel disease is selected from the group consisting of Crohn's disease, inflammatory Crohn's disease, fibrostricturing Crohn's disease, gastroduodenal Crohn's disease, Crohn's (granulomatous) colitis, ulcerative colitis, collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, and indeterminate colitis.

Embodiment 69. The polynucleotide for use as embodied in embodiment 68, wherein the inflammatory bowel disease is inflammatory Crohn's disease.

Embodiment 70. The polynucleotide for use as embodied in embodiment 68, wherein the inflammatory bowel disease is fibrostricturing Crohn's disease.

Embodiment 71. A polynucleotide of any one of embodiments 1-17, or a pharmaceutically-acceptable salt thereof, for use in the treatment of fibrosis.

Embodiment 72. The polynucleotide for use as embodied in embodiment 71, wherein the fibrosis is intestinal fibrosis.

Embodiment 73. The polynucleotide for use as embodied in embodiment 71, wherein the fibrosis is pulmonary fibrosis.

Embodiment 74. The polynucleotide for use as embodied in embodiment 71, wherein the fibrosis is synovial fibrosis.

Embodiment 75. The polynucleotide for use as embodied in embodiment 71, wherein the fibrosis is selected from the group consisting of renal fibrosis, cardiac fibrosis, endomyocardial fibrosis, myelofibrosis, retroperitoneal fibrosis, and nephrogenic systemic fibrosis.

Embodiment 76. The polynucleotide for use as embodied in any one of embodiments 60-75, wherein the polynucleotide is to be administered intraarticularly, rectally, topically, parenterally, orally, pulmonarily, intratracheally, intranasally, transdermally, or intraduodenally.

Embodiment 77. The polynucleotide for use as embodied in embodiments 76, wherein the polynucleotide is to be administered intraarticularly.

Embodiment 78. The polynucleotide for use as embodied in embodiments 76, wherein the polynucleotide is to be administered rectally.

Embodiment 79. The polynucleotide for use as embodied in embodiment 76, wherein the polynucleotide is to be administered orally.

Embodiment 80. The polynucleotide for use as embodied in any one of embodiments 60-79, wherein the patient is a human.

EXAMPLES

The disclosure is further illustrated by the following examples. The examples are provided for illustrative purposes only, and are not to be construed as limiting the scope or content of the disclosure in any way.

Example 1: Design and Evaluation of IL-34 of 3-14-3 and 4-12-4 Antisense Oligonucleotides IL-34 antisense oligonucleotides of SEQ ID NOs: 40-43 complementary to mouse and human IL-34 mRNA sequences are designed and produced by commercial manufacturers.

Knockdown of IL-34 expression are evaluated in HT-29 human and RAW 264.7 mouse cell lines. HT-29 cells (ATCC Manassas, Virginia, USA) are cultured in McCoy's 5A (Lonza, Verviers, Belgium) supplemented with 10% FBS, 1% P/S (all from Lonza) and maintained at 37° C. with 5% $CO_2$ in a humidified incubator. Murine RAW264.7 macrophages (ATCC Manassas, Virginia, USA) are cultured in Dulbecco's modified Eagle's medium (1 g/L of glucose) with 10% FBS, 1% P/S and 1% non-essential amino acid (NEA) (all from Lonza) and maintained at 37° C. with 5% $CO_2$ in a humidified incubator. The murine colon carcinoma cell line MC-38 (ABMGood, Richmond, Canada) is cultured in DMEM medium supplemented with 10% FBS and 1% P/S and maintained at 37° C. with 5% CO2 in a humidified incubator.

Cells are either left untreated or transfected with a specific IL-34 ASO or scrambled ASO using Opti-MEM medium and Lipofectamine 3000 reagent (Life Technologies, Milan, Italy) according to the manufacturer's instructions. Total RNA and protein are extracted.

Knockdown is evaluated by real-time polymerase chain reaction (RT-PCR) in HT-29 cells. RT-PCR wis performed as follows: a constant amount of RNA (0.5 μg/sample) is retro-transcribed into complementary DNA (cDNA). 1 μl of cDNA/sample is then amplified using the following protocol: denaturation for 1 minute at 95° C.; annealing for 30 seconds at 60° C., followed by 30 seconds of extension at 72° C. The following primer sequences are used: IL-34 forward, 5'-ACAGGAGCCGACTTCAGTAC-3' (SEQ ID NO: 29); IL-34 reverse, 5'-ACCAAGACCCACAGA-TACCG-3' (SEQ ID NO: 30); β-actin forward, 5'-AA-GATGACCCAGATCATGTTTGAGACC-3' (SEQ ID NO: 31); and β-actin reverse, 5'-AGCCAGTCCAGACGCAG-GAT-3' (SEQ ID NO: 32). mRNA expression is calculated relative to β-Actin mRNA expression.

HT-29 cells are transfected with human IL-34 ASOs of SEQ ID NO: 40, 41, 42, or 43, or a scrambled negative control oligonucleotide (SRC AS; 5'-AACACGTC-TATACGC-3' (SEQ ID NO: 33)) for 24 hours. IL-34 transcripts are evaluated by RT-PCR and values are normalized to β-actin.

Knockdown is also evaluated by Western blotting in HT-29 cells and RAW 264.7 cells. Western blotting is performed as follows: following transfection, cells are lysed on ice in buffer containing 10 mM HEPES (pH 7.9), 10 mM KCl, 0.1 mM EDTA, 0.2 mM EGTA, and 0.5% Nonidet P40 supplemented with 1 mM dithiothreitol, 10 mg/ml aprotinin, 10 mg/ml leupeptin, 1 mM phenylmethylsulfonyl fluoride, 1 mM Na3VO4 and 1 mM NaF. Lysates are clarified by centrifugation at 4° C., 12.000×g for 30 minutes, and separated on 10% sodium dodecyl sulphate-polyacrylamide gel electrophoresis. IL-34 is detected using mouse anti human IL-34 antibody (1:1,000 final dilution; Abcam Cambridge, UK), in combination with horseradish peroxidase (HRP)-conjugated secondary IgG monoclonal antibody (1:20,000 final dilution; Dako, Milan, Italy). HRP reaction is detected with a sensitive enhanced chemiluminescence kit (Pierce, Rockford, IL). After the analysis, blots are stripped and probed with mouse anti-human β-actin antibody (1:5,000 final dilution; Sigma-Aldrich), followed by HRP-conjugated secondary IgG monoclonal antibody (1:20,000 final dilution; Dako).

IL-34 knockdown by IL-34 ASOs is further evaluated in fibrostricturing Crohn's disease and cancer associated fibroblasts. Intestinal fibroblasts are isolated from intestinal colon cancer or fibrostricturing CD (FS CD) explants. Fibroblasts are used freshly or between passages 3 and 8. Fibroblasts are cultured in DMEM high glucose with UltraGlutamine supplemented with 10% FBS, 1% P/S (Lonza) and maintained at 37° C. with 5% $CO_2$ in a humidified incubator.

Fibroblasts are detached using Trypsin/EDTA solution evaluated for knockdown of IL-34.

Example 2: Design and Evaluation of IL-34 Gapmer Antisense Oligonucleotides

This example describes the evaluation of the capability of antisense oligonucleotides (ASOs) complementary to the IL-34 mRNA transcripts, to knock-down IL-34 expression in the HT-29 and AGS gastrointestinal cancer cell lines as well as in Lamina Propria Mononuclear Cells (LPMCs) isolated from the inflamed colonic tissue of patients affected by ulcerative colitis (UC).

Antisense oligonucleotides complementary to human, mouse, cynomolgus monkey (and other species) IL-34 mRNA transcripts were designed. The designed ASOs are single strand oligodeoxyribonucleotides, which target the same sequence in IL-34 mRNA and are modified to have a fully phosphorothioate backbone and 2'-O-methoxyethyl (2'-MOE) sugar modifications at the 5' and 3' ends.

Four different ASOs were evaluated (SEQ ID NOs: 17, 19, 42 and 43) as described below. The sequences of the test ASOs are shown in TABLE 1, with X=5-methylcytidine; Cx=2'-O-MOE cytidine; Tx:=2'-O-MOE thymidine; Gx=2'-O-MOE guanosine; and Ax=2'-O-MOE adenosine.

TABLE 1

| Seq ID NO: | Sequence | Description |
|---|---|---|
| 17 | 5'-TxCxCxAxTxGACCX GGAAGCxAxGxTxTx-3' | 5-10-5 MOE gapmer |
| 19 | 5'-TxCxCxAxTxGxACC XGGAAGxCxAxGxTxT x-3' | 6-8-6 MOE gapmer |
| 42 | 5'-TxCxCxAxTGACCXG GAAGCAxGxTxTx-3' | 4-12-4 MOE gapmer |
| 43 | 5'-TxCxCxATGACCXGG AAGCAGxTxTx-3' | 3-14-3 MOE gapmer |

The colorectal cancer cell line HT-29 and the gastric cancer cell line AGS (ATCC, Manassas, USA) were cultured in McCoy's 5A and RPMI 1640 media respectively (Lonza, Verviers, Belgium), supplemented with 10% FBS, 1% P/S (Lonza), and maintained at 37° C. with 5% $CO_2$ in a humidified incubator.

Lamina propria mononuclear cells (LPMCs) were isolated from biopsies taken from the inflamed colonic tissue of patients with ulcerative colitis (UC) as previously described in Dinallo et al., *J Crohns Colitis.* 2019 May 27; 13(6):772-784. LPMCs were resuspended in RPMI 1640 supplemented with 10% FBS, 1% P/S and maintained at 37° C. with 5% $CO_2$ in a humidified incubator. To assess the ability of IL-34 ASOs to downregulate IL-34 expression, HT-29, AGS, and UC patient-derived LPMCs were transfected with either the test IL-34 ASOs or a control of relevant scrambled antisense oligonucleotide (all used at the concentration of 200 nM) for 24 hours using Opti-MEM medium and Lipofectamine 3000 reagent (Life Technologies, Milan, Italy) according to the manufacturer's instructions. At the end, cells were collected and total RNA extracted using a PureLink mRNA Mini Kit (Thermo Fisher Scientific, Waltham, USA), according to the manufacturer's instructions. A constant amount of RNA was reverse transcribed into complementary DNA (cDNA) and amplified by real-time PCR using the following protocol: denaturation for 1 minute at 95° C.; annealing for 30 seconds at 60° C., followed by 30 seconds of extension at 72° C. Primer sequences were as follows: IL-34: forward, 5'-ACAGGAGCCGACTTCAGTAC-3' (SEQ ID NO: 29); reverse, 5'-ACCAAGACCCACAGATACCG-3'(SEQ ID NO: 30); β-actin: forward, 5'-AAGATGACCCAGAT-CATGTTTGAGACC-3'(SEQ ID NO: 31); reverse, 5'-AGCCAGTCCAGACGCAGGAT-3'(SEQ ID NO: 32). RNA expression was calculated relative to the housekeeping β-actin gene on the base of the ΔΔCt algorithm.

Figure 2:
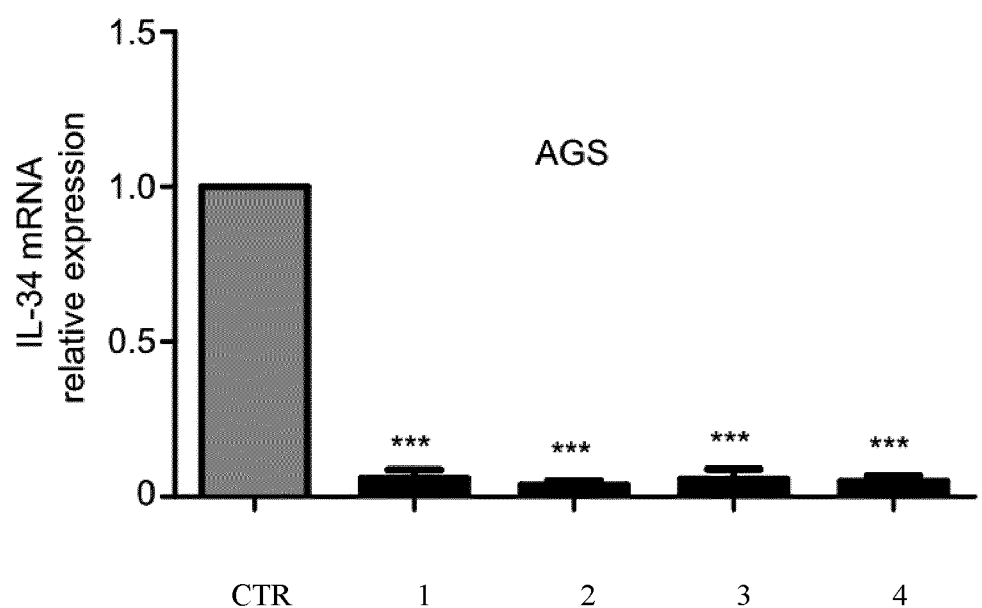
FIG. 2 shows the results of the IL-34 ASOs on the modulation of IL-34 expression in cultured AGS cells. IL-34 RNA transcripts were evaluated by real-time PCR. Levels are normalized to β-actin. (CTR=scrambled ASO, 1=SEQ ID NO: 17, 2=SEQ ID NO: 19, 3=SEQ ID NO: 42, 4=SEQ ID NO: 43). Values are mean±SEM of four experiments. Differences among groups were compared using 1-way analysis of variance followed by the Dunnett's post hoc test. IL-34 ASOs vs CTR, ***P<0.001.
Figure 3:
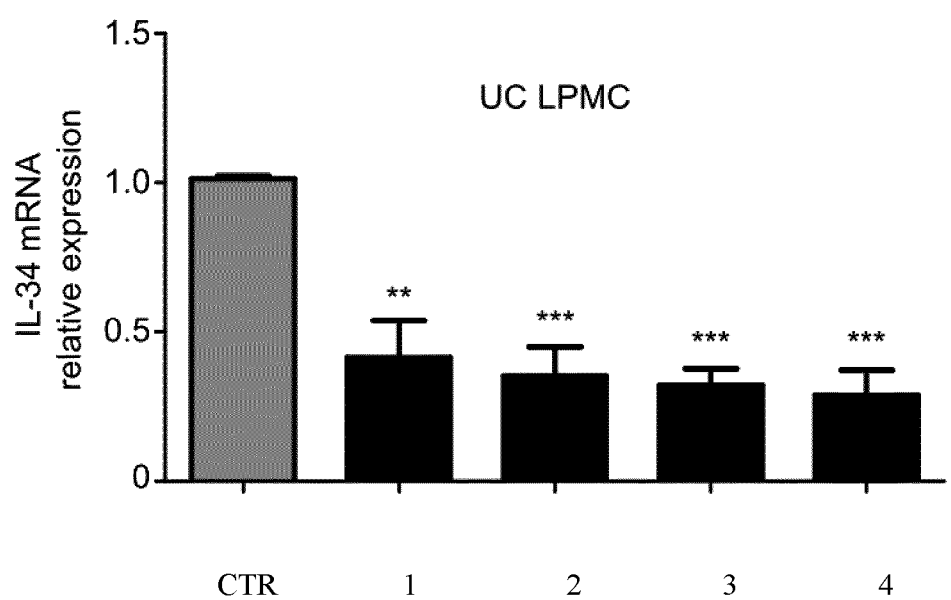
FIG. 3 shows the results of the IL-34 ASOs on the modulation of IL-34 expression in UC patient-derived LPMCs. IL-34 RNA transcripts were evaluated by real-time PCR. Levels are normalized to β-actin. (CTR=scrambled ASO, 1=SEQ ID NO: 17, 2=SEQ ID NO: 19, 3=SEQ ID NO: 42, 4=SEQ ID NO: 43). Values are mean±SEM of three experiments. Differences among groups were compared using 1-way analysis of variance followed by the Dunnett's post hoc test. IL-34 ASOs vs CTR, P<0.01, *P<0.001.

FIG. 1, FIG. 2, and FIG. 3 show the analysis of IL-34 transcripts in HT-29 cells, AGS cells, and LPMCs in conditions treated with CTR=scrambled ASO, 1=SEQ ID NO: 17, 2=SEQ ID NO: 19, 3=SEQ ID NO: 42, 4=SEQ ID NO: 43. The results show that all four IL-34 ASOs significantly reduced IL-34 RNA transcripts in HT-29 cells, AGS cells, and LPMCs as compared to the control. The data indicate that the four gapmer IL-34 ASOs are capable of efficiently down-regulating IL-34 expression in human cancer and immune cells and may be useful in relevant preclinical and clinical settings.

Example 3: Knockdown of IL-34 Expression by IL-34 Antisense Oligonucleotides

The ability of IL-34 ASOs to knockdown IL-34 expression is evaluated in HT-29 cells (human colon adenocarcinoma cell line), THP-1 cells (human leukemia monocytic cell line), RAW 264.7 cells (murine macrophage cell line), and MC-38 cells (murine colon adenocarcinoma cell line).

HT-29 cells (ATCC HTB-38, Manassas, USA) are cultured in McCoy's 5A and RPMI 1640 medium, supplemented with 10% fetal bovine serum (FBS), 1% penicillin/streptomycin (P/S), and maintained at 37° C. with 5% $CO_2$ in a humidified incubator.

THP-1 cells (ATCC TIB-202) are grown in RPMI 1640 medium supplemented with 10 FBS and 1% P/S. To induce macrophage differentiation, cells are treated with 100 ng/mL phorbol 12-myristate 13-acetate (PMA) for 24 hours and maintained at 37° C. with 5% $CO_2$ in a humidified incubator.

RAW 264.7 cells (ATCC TIB-71) are cultured in Dulbecco's modified Eagle's medium (DMEM) supplemented with 10% FBS, 1% P/S and 1% non-essential amino acids (NEAA) (Lonza) and maintained at 37° C. with 5% $CO_2$ in a humidified incubator.

MC-38 cells (ABMGood, Richmond, Canada) are cultured in DMEM medium supplemented with 10% FBS and 1% P/S and maintained at 37° C. with 5% $CO_2$ in a humidified incubator.

Cells are either left untreated or transfected with a test IL-34 ASO or a control of scrambled ASO using Opti-MEM medium and Lipofectamine 3000 reagent in the presence or absence of specific pro-inflammatory stimuli, such as lipopolysaccharides (LPS), peptidoglycan (PGN), and poly I:C.

Cells are then collected and total RNA extracted for analysis with RT-qPCR performed as follows: a constant amount of RNA is retro-transcribed into complementary DNA (cDNA). 1 μL of cDNA/sample is then amplified using the following protocol: denaturation for 1 minute at 95° C.; annealing for 30 seconds at 60° C., followed by 30 seconds of extension at 72° C. The following primer sequences are used: IL-34 forward, 5'-ACAGGAGCCGACTTCAGTAC-3' (SEQ ID NO: 29); IL-34 reverse, 5'-ACCAAGACC-CACAGATACCG-3' (SEQ ID NO: 30); β-actin forward, 5'-AAGATGACCCAGATCATGTTTGAGACC-3' (SEQ ID NO: 31); and β-actin reverse, 5'-AGCCAGTCCA- GACGCAGGAT-3' (SEQ ID NO: 32). mRNA expression is calculated relative to the housekeeping gene β-Actin mRNA expression on the base of the ΔΔCt algorithm.

IL-34 protein knockdown is evaluated by Western blotting performed as follows: following transfection, cells are lysed on ice in a buffer containing 10 mM HEPES (pH 7.9), 10 mM KCl, 0.1 mM EDTA, 0.2 mM EGTA, and 0.5% Nonidet P40 supplemented with 1 mM dithiothreitol, 10 mg/ml aprotinin, 10 mg/ml leupeptin, 1 mM phenylmethylsulfonyl fluoride, 1 mM Na3VO4 and 1 mM NaF. Lysates are clarified by centrifugation at 4° C., 12,000×g for 30 minutes, and separated on 10% sodium dodecyl sulphate-polyacrylamide gel electrophoresis. IL-34 is detected using either a mouse anti human IL-34 antibody or a rabbit anti-human IL-34 antibody, in combination with horseradish peroxidase (HRP)-conjugated secondary IgG monoclonal antibody. HRP reaction is detected with a sensitive enhanced chemiluminescence kit. After the analysis, blots are stripped and probed with mouse anti-β-actin antibody, followed by HRP-conjugated secondary IgG monoclonal antibody. Computer-assisted scanning densitometry is used to analyze the intensity of the immunoreactive bands.

The results of the transfection of the cells with the IL-34 ASOs results in decreased IL-34 RNA and protein expression.

Example 4: Knockdown of IL-34 Expression by IL-34 Antisense Oligonucleotides in Intestinal Fibroblasts IL-34 knockdown by IL-34 ASOs is further evaluated in colorectal cancer (CRC)-associated fibroblasts and fibrostricturing Crohn's disease (FS CD)-derived fibroblasts.

Human intestinal fibroblasts are isolated from explants derived from the affected tissue of patients with CRC and FS CD and phenotypically as previously described. In all the experiments, fibroblasts are used freshly or up to passage 8 and are detached using a Trypsin/EDTA solution. The human fibroblasts are cultured in DMEM high glucose with UltraGlutamine supplemented with 10% FBS, 1% P/S and maintained at 37° C. with 5% $CO_2$ in a humidified incubator.

Cells are either left untreated or transfected with a test IL-34 ASO or a control of scrambled antisense oligonucleotides. Total RNAs are extracted for analysis using RT-qPCR as described in Example 3. IL-34 ASOs result in decreased IL-34 RNA expression compared to the control.

The effect of IL-34 ASOs on collagen synthesis in the fibroblasts is also evaluated. In brief, $5 \times 10^4$ fibroblasts are plated into each well of a 12-well plate, left to adhere for 24 hours, and then either left untreated or transfected with a test IL-34 ASO or a control of scrambled ASOs for 24-48 hours. Transfection efficiency is determined by Western blotting. After 48 hours, cell-free supernatants are collected and analyzed for collagen content by a commercially available ELISA kit. IL-34 ASOs reduces both COL1A1 and COL3A1 protein synthesis in the fibroblasts compared to the control.

The effect of IL-34 ASOs on cell death is also evaluated. To score cell death, fibroblasts are washed in PBS, stained with FITC—annexin V antibody and incubated with 5 mg/mL PI for 20 min at 4° C. Fluorescence is measured using a flow cytometer. AV−/PI-cells are considered to be viable cells, AV+/PI− cells are considered to be apoptotic, and secondary necrotic cells are characterized by AV+/PI+ staining. Transfection of FS CD fibroblasts with the IL-34 ASOs does not affect cell viability.

IL-34 knockdown in fibroblasts by IL-34 ASOs results in decreased collagen production without having a significant effect on cell viability.

Example 5: Knockdown of IL-34 Expression by IL-34 Antisense Oligonucleotides

This example illustrates knockdown of expression of IL-34 by IL-34 antisense oligonucleotides in vitro in human synovial sarcoma cell line SW982 and in human fibroblast-like synoviocytes HFLS-RA.

SW982 cells are grown in Leibovitz's L15 Medium supplemented with 100 U/mL penicillin, 100 μg/mL streptomycin, and 10% fetal bovine serum (FBS). Cell cultures are maintained in a humidified atmosphere of 95% air and 5% $CO_2$ at 37°. Their activation is induced by 24 h of pre-treatment with 10 ng/mL TNFα.

HFSL-RA cells are cultured in Synoviocyte growth medium kit (basal medium with growth supplements) and maintained at 37° C., 5% $CO_2$ in a humidified incubator.

Cells are either left untreated or transfected with a test IL-34 ASO or a control of scrambled antisense oligonucleotides. Total RNAs are extracted for analysis using RT-qPCR as described in Example 3. IL-34 protein knockdown is evaluated by Western blotting as described in Example 3.

IL-34 ASOs result in decreased IL-34 RNA and protein expression compared to the control.

Example 6: Evaluation of IL-34 Antisense Oligonucleotides In Vivo in Colitis Model This example illustrates of IL-34 knockdown by IL-34 ASO in vivo in a mouse model of TNBS-induced colitis.

IL-34 ASOs are dissolved in phosphate buffered saline. For oral administration, the ASOs are diluted in bicarbonate solution pH 9.5; for i.p. and rectal administration the ASOs are diluted in PBS.

Female Balb/c mice at 7-9 weeks old are used for the TNBS-induced colitis model. To induce colitis in the mice, 2 mg of 2,4,6-trinitrobenzenesulfonic acid (TNBS) in 45% ethanol is administered to lightly anesthetized mice through a 3.5F catheter inserted into the rectum. The catheter tip is inserted 4 cm proximal to the anal verge, and 150 μL of fluid is slowly instilled into the colon, after which the mouse is held in a vertical position for 30 seconds. After 24 h of TNBS induction, mice in the treatment group receive the test IL-34 ASO or a control.

Weight changes are recorded daily to assess the induction and progression of colitis, and tissues are collected for histologic study and protein analysis. Mice are euthanized at Day 5.

For histologic studies, tissues removed from mice after euthanasia are fixed in 10% formalin solution (Sigma Aldrich), embedded in paraffin, cut into tissue sections and stained with Haematoxylin and Eosin. Stained sections are examined for evidence of colitis using different criteria such as the presence of lymphocyte infiltration, elongation and/or distortion of crypts, frank ulceration and thickening of the bowel wall. The degree of inflammation on microscopic cross-sections of the colon is graded from 0 to 4 as follows:
  0: no evidence of inflammation;
  1: low level of lymphocyte infiltration with infiltration seen in a <10% high-power field (hpf), no structural changes observed;
  2: moderate lymphocyte infiltration with infiltration seen in <10-25% hpf, crypt elongation, bowel wall thickening which does not extend beyond mucosal layer;

3: high level of lymphocyte infiltration with infiltration seen in <25-50% hpf, thickening of bowel wall which extends beyond mucosal layer;

4: marked degree of lymphocyte infiltration with infiltration seen in >50% hpf, high vascular density, crypt elongation with distortion, transmural bowel wall-thickening with ulceration.

Mice have reduced colitis after treatment with the IL-34 ASOs.

Example 7: Evaluation of IL-34 Antisense Oligonucleotides In Vivo in Arthritis Model This example illustrates knockdown of expression of IL-34 by IL-34 antisense oligonucleotides IL-34 ASO in vivo in collagen-induced arthritis (CIA) animal models.

IL-34 ASOs are dissolved in phosphate buffered saline. For oral administration the ASOs are diluted in bicarbonate solution pH 9.5; for i.p and rectal administration the ASOs are diluted in PBS.

DBA/1 mice at 8-12 weeks of age are used. The animals are challenged with bovine type-II collagen emulsified with Complete Freund's adjuvant (CFA) on Day 0 (0.1 mg/0.1 mL/mouse, intradermally (ID) at the base of the tail) and boosted i.d. on Day 21 with collagen emulsified with IFA instead of CFA (0.1 mg/0.1 mL/mouse). Animals are stratified into groups of 10 each, based on the volume of two hind paws on Day 29. ASOs and vehicle are administered by intra-articular injection at different dosing schedule from Day 29 to Day 42. Control article dexamethasone (0.3 mg/kg) is administered orally. Arthritis is assessed by using a qualitative severity score system and hind paw volume (mL) measured with a plethysmometer on Days 21, 23, 25, 27, 29, 31, 33, 35, 37, 39, 41 and 43. Additional analyses that can be performed include hind paw harvest and weight at termination, biomarkers (protein and/or mRNA), and histopathology.

Alternatively, female Lewis rats weighing 180±20 g are used. The animals are challenged with porcine type-II collagen with incomplete Freund's adjuvant on Day 1 (0.2 mg/0.2 mL/rat, subcutaneously (SC) at the base of the tail) and booster on Day 7 (0.1 mg/0.1 mL/rat, SC). Animals are stratified into groups of 6 each, based on the volume of two hind paws on Day 16 and then dosing begins on Day 17. Control article dexamethasone (0.3 mg/kg) is administered orally once a day for 14 consecutive days from Day 17 to Day 30. ASOs and vehicle are administered by intra-articular injection. Arthritis is assessed by using a qualitative severity score system and hind paw volume (mL) measured with a plethysmometer on Days 1, 7, 10, 14, 16, 18, 20, 22, 24, 26, 28 and 30. Additional analyses that can be performed include biomarkers (protein and/or mRNA) and histopathology.

Animals treated with IL-34 ASOs show reduced arthritis.

EQUIVALENTS

The disclosure can be embodied in other specific forms with departing from the essential characteristics thereof. The foregoing embodiments therefore are to be considered illustrative rather than limiting on the disclosure described herein. The scope of the disclosure is indicated by the appended claims rather than by the foregoing description, and all changes that come within the meaning and range of equivalency of the claims are intended to be embraced therein.

SEQUENCE LISTING

X is 5-methylcytidine; Ax is 2'-O-(2-methoxyethyl)adenosine; Cx is 2'-O-(2-methoxyethyl)cytidine; Gx is 2'-O-(2-methoxyethyl)guanosine; Tx is 2'-O-(2-methoxyethyl)thymidine; Ay is 2'-O-methyladenosine; Cy is 2'-O-methylcytidine; Gy is 2'-O-methylguanosine; Ty is 2'-O-methylthymidine

| SEQ ID NO | Sequence |
|---|---|
| 1 | 5'-CTCACCAAGACCCACAG-3' |
| 2 | 5'-GGCTTTGGGCCGCACCAGCT-3' |
| 3 | 5'-CTTTGGGCCGCACCAGCTTC-3' |
| 4 | 5'-TGGGCCGCACCAGCTTCAGG-3' |
| 5 | 5'-TCCATGACCCGGAAGCAGTT-3' |
| 6 | 5'-TGTTTCATGTACTGAAG-3' |
| 7 | 5'-CTTTGGGCXGCACCAGCTTC-3' |
| 8 | 5'-TCCATGACCXGGAAGCAGTT-3' |
| 9 | 5'-cttTGGGCXGCACCAGCttc-3' |
| 10 | 5'-ctttGGGCXGCACCAGcttc-3' |
| 11 | 5'-cttTGGGCcgCACCAGCttc-3' |
| 12 | 5'-cttTGGGCcGCACCAGCttc-3' |
| 13 | 5'-ggcXGCACCAGCttc-3' |
| 14 | 5'-cttTGGGCXGCACcag-3' |
| 15 | 5'-tgaCCGGAAGCAgtt-3' |
| 16 | 5'-CxTxTxTxGxGGCXGCACCAGCxTxTxCx-3' |
| 17 | 5'-TxCxCxAxTxGACCXGGAAGCxAxGxTxTx-3' |
| 18 | 5'-CxTxTxTxGxGxGCXGCACCAxGxCxTxTxCx-3' |
| 19 | 5'-TxCxCxAxTxGxACCXGGAAGCxAxGxTxTx-3' |
| 20 | 5'-CxTxTxTxGxGxGxCxXGxCxAxCxCxAxGxCxTxTxCx-3' |
| 21 | 5'-TxCxCxAxTxGxAxCxCxXGxGxAxAxGxCxAxGxTxTx-3' |
| 22 | 5'-CyTyTyTyGyGGCXGCACCAGyCyTyTyCy-3' |
| 23 | 5'-TyCyCyAyTyGACCXGGAAGCyAyGyTyTy-3' |
| 24 | CATCAGACGGGAAGCCTGGACTGTGGGTTGGGGGCAGCCTC AGCCTCTCCAACCTGGCACCCACTGCCCGTGGCCCTTAGGC ACCTGCTTGGGGTCCTGGAGCCCCTTAAGGCCACCAGCAAA TCCTAGGAGACCGAGTCTTGGCACGTGAACAGAGCCAGATT TCACACTGAGCAGCTGCAGTCGGAGAAATCAGAGAAAGCGT CACCCAGCCCCAGATTCCGAGGGGCCTGCCAGGGACTCTCT CCTCCTGCTCCTTGGAAAGGAAGACCCCGAAAGACCCCCAA GCCACCGGCTCAGACCTGCTTCTGGGCTGCCATGGGACTTG CGGCCACCGCCCCCCGGCTGTCCTCCACGCTGCCGGGCAGA TAAGGGCAGCTGCTGCCCTTGGGGCACCTGCTCACTCCCGC AGCCCAGCCACTCCTCCAGGGCCAGCCCTTCCCTGACTGAG TGACCACCTCTGCTGCCCCGAGGCCATGTAGGCCGTGCTTA GGCCTCTGTGGACACACTGCTGGGGACGGCGCCTGAGCTCT CAGGGGGACGAGGAACACCACCATGCCCCGGGGCTTCACCT GGCTGCGCTATCTTGGGATCTTCCTTGGCGTGGCCTTGGGG AATGAGCCTTTGGAGATGTGGCCCTTGACGCAGAATGAGGA GTGCACTGTCACGGGTTTTCTGCGGGACAAGCTGCAGTACA GGAGCCGACTTCAGTACATGAAACACTACTTCCCCATCAAC |

| SEQ ID NO | Sequence |
|---|---|
|  | TACAAGATCAGTGTGCCTTACGAGGGGGTGTTCAGAATCGC<br>CAACGTCACCAGGCTGAGGGCCCAGGTGAGCGAGCGGGAGC<br>TGCGGTATCTGTGGGTCTTGGTGAGCCTCAGTGCCACTGAG<br>TCGGTGCAGGACGTGCTGCTCGAGGGCCACCCATCCTGGAA<br>GTACCTGCAGGAGGTGCTGCTCGAGGGCCACCCATCCTGGAA<br>AGGGCCTCACGGATGTGGAGGTCAGCCCCAAGGTGGAATCC<br>GTGTTGTCCCTCTTGAATGCCCCAGGGCCAAACCTGAAGCT<br>GGTGCGGCCCAAAGCCCTGCTGGACAACTGCTTCCGGGTCA<br>TGGGAGCTGCTGTACTGCTCCTGCTGTAAACAAAGCTCCGTC<br>CTAAACTGGCAGGACTGTGAGGTGCCAAGTCCTCAGTCTTG<br>CAGCCCAGAGCCCTCATTGCAGTATGCGGCCACCCAGCTGT<br>ACCCTCCGCCCCGTGGTCCCCAGCTCCCCGCCTCACTCC<br>ACGGGCTCGGTGAGGCCGGTCAGGGCACAGGGCGAGGGCCT<br>CTTGCCCTGAGCACCCTGGATGGTGACTGCGGATAGGGGCA<br>GCCAGACCAGCTCCCACAGGAGTTCAACTGGGTCTGAGACT<br>TCAAGGGTGGTGGTGGGAGCCCCCCTTGGGAGAGGACCCC<br>TGGGAAGGGTGTTTTTCCTTTGAGGGGGATTCTGTGCCACA<br>GCAGGGCTCAGCTTCCTGCCTTCCATAGCTGTCATGGCCTC<br>ACCTGGAGCGGAGGGGACCTGGGGACCTGAAGGTGGATGGG<br>GACACAGCTCCTGGCTTCTCCTGGTGCTGCCCTCACTGTCC<br>CCCCGCCTAAAGGGGTACTGAGCCTCCTGTGGCCCGCAGC<br>AGTGAGGGCACAGCTGTGGGTTGCAGGGGAGACAGCCAGCA<br>CGGCGTGGCCATTCTATGACCCCCAGCCTGGCAGACTGGG<br>GAGCTGGGGCAGAGGGCGGTGCCAAGTGCCACATCTTGCC<br>ATAGTGGATGCTCTTCCAGTTTCTTTTTTCTATTAAACACC<br>CCACTTCCTTTGAAAAAAAAAAAAAAAAAA<br>(NM_001172771.1 Homo sapiens interleukin<br>34 (IL34), transcript variant 2, mRNA) |
| 25 | CTCGAAGCTCGGCGTCTGTGATGGTCTACGGGGCTTTCGAG<br>GTGATCAGGCAGCGTCAGTCTTCAGCCGCTAAGCCGAGAAG<br>GAGTCAGTCAGAGAGCCTTGGGCCAGAGTTCCAGGGGCTCT<br>GGGAGTGGCTGCCAGAGCCAGATTTCACACTGAGCAGCTGC<br>AGTCGGAGAAATCAGAGAAAGCGTCACCCAGCCCCAGATTC<br>CGAGGGGCCTGCCAGGGACTCTCTCCTCCTGCTCCTTGGAA<br>AGGAAGACCCCGAAAGACCCCCAAGCCACCGGCTCAGACCT<br>GCTTCTGGGCTGCCATGGGACTTGCGGCCACCGCCCCCGG<br>CTGTCCTCCACGCTGCCGGGCAGATAAGGGCAGCTGCTGCC<br>CTTGGGGCACCTGCTCACTCCCGCAGCCCAGCCACTCCTCC<br>AGGGCCAGCCCTTCCCTGACTGAGTGACCACCTCTGCTGCC<br>CCGAGGCCATGTAGGCCGTGCTTAGGCCTCTGTGGACACAC<br>TGCTGGGGACGGCGCCTGAGCTCTCAGGGGACGAGGAACA<br>CCACCATGCCCCGGGGCTTCACCTGGCTGCGCTATCTTGGG<br>ATCTTCCTTGGCGTGGCCTTGGGGAATGAGCCTTTGGAGAT<br>GTGGCCCTTGACGCAGAATGAGGAGTGCACTGTCACGGGTT<br>TTCTGCGGGACAAGCTGCAGTACAGGAGCCGACTTCAGTAC<br>ATGAAACACTTCCCCATCAACTACAAGATCAGTGTGC<br>TTACGAGGGGGTGTTCAGAATCGCCAACGTCACCAGGCTGC<br>AGAGGGCCCAGGTGAGCGAGCGGGAGCTGCGGTATCTGTGG<br>GTCTTGGTGAGCCTCAGTGCCACTGAGTCGGTGCAGGACGT<br>GCTGCTCGAGGGCCACCCATCCTGGAAGTACCTGCAGGAGG<br>TGGAGACGCTGCTGCTGAATGTCCAGCAGGGCCTCACGGAT<br>GTGGAGGTCAGCCCCAAGGTGGAATCCGTGTTGTCCCTCTT<br>GAATGCCCCAGGGCCAAACCTGAAGCTGGTGCGGCCCAAAG<br>CCCTGCTGGACAACTGCTTCCGGGTCATGGGAGCTGCTGTAC<br>TGCTCCTGCTGTAAACAAAGCTCCGTCCTAAACTGGCAGGA<br>CTGTGAGGTGCCAAGTCCTCAGTCTTGCAGCCCAGAGCCCT<br>CATTGCAGTATGCGGCCACCCAGCTGTACCCTCCGCCCCG<br>TGGTCCCCAGCTCCCGCCTCACTCCACGGGCTCGGTGAG<br>GCCGGTCAGGGCACAGGGCGAGGGCCTCTTGCCCTGAGCAC<br>CCTGGATGGTGACTGCGGATAGGGGCAGCCAGACCAGCTCC<br>CACAGGAGTTCAACTGGGTCTGAGACTTCAAGGGTGGTGG<br>TGGGAGCCCCCCTTGGGAGAGGACCCCTGGGAAGGGTGTTT<br>TTCCTTTGAGGGGGATTCTGTGCCACAGCAGGGCTCAGCTT<br>CCTGCCTTCCATAGCTGTCATGGCCTCACCTGGAGCGGAGG<br>GGACCTGGGGACCTGAAGGTGGATGGGGACACAGCTCCTGG<br>CTTCTCCTGGTGCTGCCCTCACTGTCCCCCCGCCTAAAGGG<br>GGTACTGAGCCTCCTGTGGCCCGCAGCAGTGAGGGCACAGC<br>TGTGGGTTGCAGGGGAGACAGCCAGCACGGCGTGGCCATTC<br>TATGACCCCCAGCCTGGCAGACTGGGGAGCTGGGGCAGA<br>GGGCGGTGCCAAGTGCCACATCTTGCCATAGTGGATGCTCT<br>TCCAGTTTCTTTTTTCTATTAAACACCCCACTTCCTTTGGA<br>AAAAAAAAAAAAAAA<br>(NM_001172772.1 Homo sapiens interleukin<br>34 (IL34), transcript variant 3, mRNA) |
| 26 | CATCAGACGGGAAGCCTGGACTGTGGGTTGGGGGCAGCCTC<br>AGCCTCTCCAACCTGGCACCCACTGCCCGTGGCCCTTAGGC<br>ACCTGCTTGGGGTCCTGGAGCCCCTTAAGGCCACCAGCAAA<br>TCCTAGGAGACCGAGTCTTGGCACGTGAACAGAGCCAGATT<br>TCACACTGAGCAGCTGCAGTCGGAGAAATCAGAGAAAGCGT<br>CACCCAGCCCCAGATTCCGAGGGGCCTGCCAGGGACTCTCT<br>CCTCCTGCTCCTTGGAAAGGAAGACCCCGAAAGACCCCCAA<br>GCCACCGGCTCAGACCTGCTTCTGGGCTGCCATGGGACTTG<br>CGGCCACCGCCCCCGGCTGTCCTCCACGCTGCCGGGCAGA<br>TAAGGGCAGCTGCTGCCCTTGGGGCACCTGCTCACTCCCGC<br>AGCCCAGCCACTCCTCCAGGGCCAGCCCTTCCCTGACTGAG<br>TGACCACCTCTGCTGCCCCGAGGCCATGTAGGCCGTGCTTA<br>GGCCTCTGTGGACACACTGCTGGGGACGGCGCCTGAGCTCT<br>CAGGGGGACGAGGAACACCACCATGCCCCGGGGCTTCACCT<br>GGCTGCGCTATCTTGGGATCTTCCTTGGCGTGGCCTTGGGG<br>AATGAGCCTTTGGAGATGTGGCCCTTGACGCAGAATGAGGA<br>GTGCACTGTCACGGGTTTTCTGCGGGACAAGCTGCAGTACA<br>GGAGCCGACTTCAGTACATGAAACACTTCCCCATCAAC<br>TACAAGATCAGTGTGCCTTACGAGGGGGTGTTCAGAATCGC<br>CAACGTCACCAGGCTGCAGAGGGCCCAGGTGAGCGAGCGGG<br>AGCTGCGGTATCTGTGGGTCTTGGTGAGCCTCAGTGCCACT<br>GAGTCGGTGCAGGACGTGCTGCTCGAGGGCCACCCATCCTG<br>GAAGTACCTGCAGGAGGTGGAGACGCTGCTGCTGAATGTCC<br>AGCAGGGCCTCACGGATGTGGAGGTCAGCCCCAAGGTGGAA<br>TCCGTGTTGTCCCTCTTGAATGCCCCAGGGCCAAACCTGAA<br>GCTGGTGCGGCCCAAAGCCCTGCTGGACAACTGCTTCCGGG<br>TCATGGGAGCTGCTGTACTGCTCCTGCTGTAAACAAAGCTCC<br>GTCCTAAACTGGCAGGACTGTGAGGTGCCAAGTCCTCAGTC<br>TTGCAGCCCAGAGCCCTCATTGCAGTATGCGGCCACCCAGC<br>TGTACCCTCCGCCCCGTGGTCCCCAGCTCCCCGCCTCAC<br>TCCACGGGCTCGGTGAGGCCGGTCAGGGCACAGGGCGAGGG<br>CCTCTTGCCCTGAGCACCCTGGATGGTGACTGCGGATAGGG<br>GCAGCCAGACCAGCTCCCACAGGAGTTCAACTGGGTCTGAG<br>ACTTCAAGGGTGGTGGTGGGAGCCCCCCTTGGGAGAGGAC<br>CCCTGGGAAGGGTGTTTTTCCTTTGAGGGGGATTCTGTGCC<br>ACAGCAGGGCTCAGCTTCCTGCCTTCCATAGCTGTCATGGC<br>CTCACCTGGAGCGGAGGGGACCTGGGGACCTGAAGGTGGAT<br>GGGGACACAGCTCCTGGCTTCTCCTGGTGCTGCCCTCACTG<br>TCCCCCCGCCTAAAGGGGTACTGAGCCTCCTGTGGCCCGC<br>AGCAGTGAGGGCACAGCTGTGGGTTGCAGGGGAGACAGCCA<br>GCACGGCGTGGCCATTCTATGACCCCCAGCCTGGCAGACT<br>GGGGAGCTGGGGCAGAGGGCGGTGCCAAGTGCCACATCTT<br>GCCATAGTGGATGCTCTTCCAGTTTCTTTTTTCTATTAAAC<br>ACCCCACTTCCTTTGGAAAAAAAAAAAAAAAAAA<br>(NM_152456.2 Homo sapiens interleukin 34<br>(IL34), transcript variant 1, mRNA) |
| 27 | TCTAGAAACAAATCTGAGCTGCTGTAGCGTGTGTCCCCCGC<br>CCTCCGAGAAGACTGTAGGCTGAACACACAACAGCCTGTCC<br>CACACAGCATTTACTGCCACAGCCCCCAAGGCACCTGCTCC<br>AGGCCTTGAGCTGCTCAAAGCTTCCGGCGACGGCGACTGTA<br>GAAGCCCACATCCTGGCAGGTGAGCAGAGCTAGACTTCACG<br>CTGAGCAGCTGCAGCCGAAGAAACCAGAGAAAGCGCCACCC<br>AGCCCCAGATTCCAAGAGGCCTGCCTGCTGGGGACTCCCTT<br>CTCTTCTTCCTCCTCCTCCTCTTCCTCCTCCTGAGACCCTC<br>AAAGTCACTGTCTCACACCAGTTCCTGAGCTGCAATGGGAC<br>TGGCAGCCACTGCCCCTGGCTGTCCTCCGCCCTGCCAAGC<br>AGATAGGGCGGTAGCTACCCCAGGATATCTGCCCCCTCTC<br>AGCCTGGACCAGCCCTTTCTGGACTTGGTGGCCACCCTTTGC<br>TGACCTAAGGCCATGTAGTCCCTGGCTCAGGCCTCTGGACA<br>CACTTCTGGGACAGTGCCTCTGCTCTCAGGGGCACCCAG<br>TGCACCACCATGCCCTGGGACTCGCCTGGCTATACTGTCT<br>TGGGATCCTACTTGACGTGCTTTGGGAAACAGAATTTGG<br>AGATATGACTCTGACCCAAGATAAGGAGTGTGACCTTACA<br>GGCTACCTTCGGGCAAGCTGCAGTACAAGAACCGGCTTCA<br>GTACATGAAACATTACTTCCCCATCAACTACAGGATTGCTG<br>TGCCTTATGAGGGGTACTCAGAGTGGCCAACATCACAAGG<br>CTGCAGAAGGCTCACGTGAGCTGAGCGAGAGCTTCGGTACCT<br>GTGGGTCTTGGTGAGTCTCAATGCCACTGAGTCTGTGATGG<br>ATGTACTTCTCGAGGGCCACCCGTCCTGGAAGTATCTACAG<br>GAGGTTCAGACATTGCTGGAGAACTACAGCGGAGCCTCAT<br>GGATGTGGAGATTGCCCTCACGTGGAAGCTGTGTTATCTC<br>TTCTGAGTACTCCAGGCCTAAGCCTGAAGCTGGTGCGGCCC<br>AAAGCCTTGCTGGACAACTGCTTCCGGGTCATGGAACTGCT |

| SEQ ID NO | Sequence |
|---|---|
| | GTACTGTTCTTGCTGTAAACAAAGCCCCATCTTAAAATGGC<br>AGGACTGCGAGCTGCCCAGGCTCCATCCCCACAGTCCGGGG<br>TCCTTGATGCAATGTACAGCTACAAATGTGTACCCTTTGTC<br>TCGGCAGACCCCCACCTCCCTGCCCGGATCCCCAAGCTCAA<br>GCCATGGCTCGTTGCCCTGAGCAATCTATGTATTGACCCTG<br>GGTCGGGCCACTGGATGCATTTCAGAAACTGGCCTGGATCT<br>GAGACCTTCCTGGATGGTGGGTAGGTAGCCCCTTTAGGAAA<br>GGCCTTCAGGGAAAGGCCTCCTGCCTTCTCTTCCACACCCA<br>GGCTTCCTGCCTTCTGGTGGTATCACGGAGCCTCAGGGGAG<br>GGATGTGGAGGGGAGGGCTGGTTGCTATCCCTTACAGCCAC<br>CTCTGCTTGTGGCCCGGTCCGAAATCTGCAAACACTGTTGC<br>CCCACAGGCGGGTGGCCAAGAACGACGGGGTGCCTCCTAGG<br>ATCCCAGGACTTACTGGGGCTTTTCAGTTGTGCTGACTGTG<br>GGGTGCTGGGCCGAGGACCAACCAAATGCCGTATCTTGCCA<br>TGACGATGCTCTTCTGGTTCCTTTTTCTATTAAATGGCCAT<br>TTATTTGGTTTGGCTTGCAAAAAAA<br>(NM_001135100.2 Mus musculus interleukin 34 (Il34), transcript variant 1, mRNA) |
| 28 | TCTAGAAACAAATCTGAGCTGCTGTAGCGTGTGTCCCCCGC<br>CCTCCGAGAAGACTGTAGGCTGAACACACAACAGCCTGTCC<br>CACACAGCATTTACTGCCACAGCCCCCAAGGCACCTGCTCC<br>AGGCCTTGAGCTGCTCAAAGCTTCCGGCGACGGCGACTGTA<br>GAAGCCCACATCCTGGCAGGTGAGCAGAGCTAGACTTCACG<br>CTGAGCAGCTGCAGCCGAAGAAACCAGAGAAAGCGCCACCC<br>AGCCCCAGATTCCAAGAGGGCCTGCCTGCTGGGGACTCCCTT<br>CTCTTCTTCCTCCTCCTCTTCCTCCTGAGACCCTC<br>AAAGTCACTGTCTCACACCAGTTCCTGAGCTGCAATGGGAC<br>TGGCAGCCACTGCCCCCTGGCTGTCCTCCGCCCTGCCAAGC<br>AGATAGGGCGGTAGCTACCCCAGGAGTATCTGCCCCCTCTC<br>AGCCTGGACCAGCCCTTTCTGGACTTGGTGGCCACCTTTGC<br>TGACCTAAGGCCATGTAGTCCCTGGCTCAGGCCTCTGGACA<br>CACTTCTGGGGACAGTGCCTCTGCTCTCAGGGGGCACCCAG<br>TGCACCACCATGCCCTGGGGACTCGCCTGGCTATACTGTCT<br>TGGGATCCTACTTGACGTGGCTTTGGGAAACAGAGAATTTGG<br>AGATATGGACTCTGACCCAAGATAAGGAGTGTGACCTTACA<br>GGCTACCTTCGGGGCAAGCTGCAGTACAAGAACCGGCTTCA<br>GTACATGAAACATTACTTCCCCATCAACTACAGGATTCATG<br>TGCCTTATGAGGGGGTACTCAGAGTGGCCAACATCACAAGG<br>CTGCAGAAGGCTCACGTGAGTGAGCGAGAGCTTCGGTACCT<br>GTGGGTCTTGGTGAGTCTCAATGCCACTGAGTCTGTGATGG<br>ATGTACTTCTCGAGGGCCACCCGTCCTGGAAGTATCTACAG<br>GAGGTTCAGACATTGCTGGAGAACGTACAGCGGAGCTCAT<br>GGCCGTTGGTGTACACCTGCCGGGACACGTACTTGTGACCC<br>TGCTCAGCCAGCTGCCTGGCCTCCCCAGCCCATGGGCAGA<br>TCATTTGACACCAGCTGGGAGCTTCTGATGATGAAAGGATG<br>TGGAGATTGGCCCTCACGTGGAACTGCAGCGAGCTGTTATCTTCTG<br>AGTACTCCAGGCCTAAGCCTGAAGCTGGTGCGGCCCAAAGC<br>CTTGCTGGACAACTGCTTCCGGGTCATGGAACTGCTGTACT<br>GTTCTTGCTGTAAACAAAGCCCCATCTTAAAATGGCAGGAC<br>TGCGAGCTGCCCAGGCTCCATCCCCACAGTCCGGGGTCCTT<br>GATGCAATGTACAGCTACAAATGTGTACCCTTTGTCTCGGC<br>AGACCCCCACCTCCCTGCCCGGATCCCCAAGCTCAAGCCAT<br>GGCTCGTTGCCCTGAGCAATCTATGTATTGACCCTGGGTCG<br>GCCACTGGATGCATTTCAGAAACTGGCCTGGATCTGAGAC<br>CTTCCTGGATGGTGGGTAGGTAGCCCCTTTAGGAAAGGCCT<br>TCAGGGAAAGGCCTCCTGCCTTCTCTTCCACACCCAGGCTT<br>CCTGCCTTCTGGTGGTATCACGGAGCCTCAGGGGAGGGATG<br>TGGAGGGGAGGGCTGGTTGCTATCCCTTACAGCCACCTCTG<br>CTTGTGGCCCGGTCCGAAATCTGCAAACACTGTTGCCCCAC<br>AGGCGGGTGGCCAAGAACGACGGGGTGCCTCCTAGGATCCC<br>AGGACTTACTGGGGCTTTTCAGTTGTGCTGACTGTGGGGTG<br>CTGGGCCGAGGACCAACCAAATGCCGTATCTTGCCATGACG<br>ATGCTCTTCTGGTTCCTTTTTCTATTAAATGGCCATTTATT<br>TGGTTTGGCTTGCAAAAAAA<br>(NM_029646.3 Mus musculus interleukin 34 (IL34), transcript variant 2, mRNA) |
| 29 | 5'-ACAGGAGCCGACTTCAGTAC-3' |
| 30 | 5'-ACCAAGACCCACAGATACCG-3' |
| 31 | 5'-AAGATGACCCAGATCATGTTTGAGACC-3' |
| 32 | 5'-AGCCAGTCCAGACGCAGGAT-3' |
| 33 | 5'-AACACGTCTATACGC-3' |
| 34 | 5'-CTGCTCAACTTTCTGCGAAG-3' |
| 35 | 5'-CTCATCTCCACATAGGTGTC-3' |
| 36 | 5'-GGACACAGAGGTTTCAGTGG-3' |
| 37 | 3'-GGTGACTTTGGAGACACAGG-5 |
| 38 | 5'-GGAGAATGTTGTGCAGTTTGC-3' |
| 39 | 3'-CGTTTGACGTGTTGTAAGAGG-5' |
| 40 | 5'-CxTxTxTxGGGCXGCACCAGCTxTxTxCx-3' |
| 41 | 5'-CxTxTxTGGGCXGCACCAGCTxTxCx-3' |
| 42 | 5'-TxCxCxAxTGACCXGGAAGCAxGxTxTx-3' |
| 43 | 5'-TxCxCxATGACCXGGAAGCAGxTxTx-3' |
| 44 | AGACGGGAAGCCTGGACTGTGGGTTGGGGGCAGCCTCAGCC<br>TCTCCAACCTGGCACCCACTGCCCGTGGCCCTTAGGCACCT<br>GCTTGGGGTCCTGGAGCCCCTTAAGGCCACCAGCAAATCCT<br>AGGAGACCGAGTCTTGGCACGTGAACAGAGCCAGATTTCAC<br>ACTGAGCAGCTGCAGTCGGAGAAATCAGAGAAAGCGTCACC<br>CAGCCCCAGATTCCGAGGGCCTGCCAGGGACTCTCTCCTC<br>CTGCTCCTTGGAAAGGAACCCCGAAAGACCCCCAAGCCA<br>CCGGCTCAGACCTGCTTCTGGGCTGCCATGGGACTTGCGGC<br>CACCGCCCCCGGCTGTCCTCCACGCTGCCGGGCAGATAAG<br>GGCAGCTGCTGCCCTTGGGCACCTGCTCACTCCCGCAGCC<br>CAGCCACTCCTCCAGGCCAGCCCTTCCCTGACTGAGTGAC<br>CACCTCTGCTGCCCCGAGGCCATGTAGGCCGTGCTTAGGCC<br>TCTGTGGACACACTGCTGGGGACGGCGCCTGAGCTCTCAGG<br>GGGACGAGGAACACCACCATGCCCCGGGGCTTCACCTGGCT<br>GCGCTATCTTGGGGATCTTCTTCCTTGGCGTGCGCCTTGGGGAATG<br>AGCCTTTGGAGATGTGCCCTTGACGCAGAATGAGGAGTGC<br>ACTGTCACGGGTTTCTGCGGGACAAGCTGCAGTACAGGAG<br>CCGACTTCAGTACATGAAACACTACTTCCCCATCAACTACA<br>GATCAGTGTGCCTTACGAGGGGTGTTCAGAATCGCCAAC<br>GTCACCAGGCTGCTGGAAGACCCCAGGTGAGCGAGCGGGAGCT<br>GCGGTATCTGTGGGCTTGGTGAGCCTCAGTGCCACTGAGT<br>CGGTGCAGGACGTGCTGCTCGAGGGCACCCATCCTGGAAG<br>TACCTGCAGGAGGTGGAGACGCTGCTGCTGAATGTCCAGCA<br>GGGCCTCACGGATCTGGAGGTGCACCCCAAGGTGGAATCCG<br>TGTTGTCCCTCTTGAATGCCCCAGGGCCCAAACCTGAAGCTG<br>GTGCGGCCCAAAGCCCTGCTGGACAACTGCTTCCGGGTCAT<br>GGAGCTGCTGTACTGCTCCTGCTGTAAACAAAGCTCCGTCC<br>TAAACTGGCAGGACTGTGAGGTGCCAAGTCCTCAGTCTTGC<br>AGCCCAGAGCCCTCATTGCAGTATGCGGCCACCCAGCTGTA<br>CCCTCCGCCCCGTGGTCCCCAGCTCCCGCCTCACTCCA<br>CGGGCTCGGTGAGGCCGGTCAGGGCACAGGGCGAGGGCCTC<br>TTGCCCTGAGCACCCTGGATGGTGACTGCGGATAGGGGCAG<br>CCAGACCAGCTCCCACAGGAGTTCAACTGGGTCTGAGACTT<br>CAAGGGGTGGTGGTGGGAGCCCCCTTGGGAGAGGACCCCT<br>GGGAAGGGTGTTTTTCCTTTGAGGGGGATTCTGTGCCACAG<br>CAGGGCTCAGCTTCCTGCCTTCCATAGCTGTCATGGCCTCA<br>CCTGGAGCGGAGGGACCTGGGGACCTGAAGGTGGATGGGG<br>ACACAGCTCCTGGCTTCTCCTGGTGCTGCCCTCACTGTCCC<br>CCCGCCTAAAGGGGTACTGAGCCTCCTGTGGCCCGCAGCA<br>GTGAGGGCACAGCTGTGGGTTGCAGGGGAGACAGCCAGCAC<br>GGCGTGGCCATTCTATGACCCCCCAGCCTGGCAGACTGGGG<br>AGCTGGGGGCAGAGGGCGGTGCCAAGTGCCACATCTTGCCA<br>TAGTGGATGCTCTTCCAGTTTCTTTTTTCTATTAAACACCC<br>CACTTCCTTTGG<br>NM 152456.3 Homo sapiens interleukin 34 (IL34), transcript variant 1, mRNA |
| 45 | AGACGGGAAGCCTGGACTGTGGGTTGGGGGCAGCCTCAGCC<br>TCTCCAACCTGGCACCCACTGCCCGTGGCCCTTAGGCACCT<br>GCTTGGGGTCCTGGAGCCCCTTAAGGCCACCAGCAAATCCT<br>AGGAGACCGAGTCTTGGCACGTGAACAGAGCCAGATTTCAC<br>ACTGAGCAGCTGCAGTCGGAGAAATCAGAGAAAGCGTCACC |

| SEQ ID NO | Sequence |
|---|---|
| | CAGCCCCAGATTCCGAGGGGCCTGCCAGGGACTCTCTCCTC<br>CTGCTCCTTGGAAAGGAAGACCCCGAAAGACCCCCAAGCCA<br>CCGGCTCAGACCTGCTTCTGGGCTGCCATGGGACTTGCGGC<br>CACCGCCCCCGGCTGTCCTCCACGCTGCCGGGCAGATAAG<br>GGCAGCTGCTGCCCTTGGGGCACCTGCTCACTCCCGCAGCC<br>CAGCCACTCCTCCAGGGCCAGCCCTTCCCTGACTGAGTGAC<br>CACCTCTGCTGCCCCGAGGCCATGTAGGCCGTGCTTAGGCC<br>TCTGTGGACACACTGCTGGGACGGCGCCTGAGCTCTCAGG<br>GGGACGAGGAACACCACCATGCCCCGGGGCTTCACCTGGCT<br>GCGCTATCTTGGGATCTTCCTTGGCGTGGCCTTGGGGAATG<br>AGCCTTTGGAGATGTGGCCCTTGACGCAGAATGAGGAGTGC<br>ACTGTCACGGGTTTTCTGCGGGACAAGCTGCAGTACAGGAG<br>CCGACTTCAGTACATGAAACACTACTTCCCCATCAACTACA<br>AGATCAGTGTGCCTTACGAGGGGGTGTTCAGAATCGCCAAC<br>GTCACCAGGCTGAGGGCCAGGTGAGCGAGCGGGAGCTGCG<br>GTATCTGTGGGTCTTGGTGAGCCTCAGTGCCACTGAGTCGG<br>TGCAGGACGTGCTGCTCGAGGGCCACCCATCCTGGAAGTAC<br>CTGCAGGAGGTGGAGACGCTGCTGCTGAATGTCCAGCAGGG<br>CCTCACGGATGTGGAGGTCAGCCCCAAGGTGGAATCCGTGT<br>TGTCCCTCTTGAATGCCCCAGGGCCAAACCTGAAGCTGGTG<br>CGGCCCAAAGCCCTGCTGGACAACTGCTTCCGGGTCATGGA<br>GCTGCTGTACTGCTCCTGCTGTAAACAAAGCTCCGTCCTAA<br>ACTGGCAGGACTGTGAGGTGCCAAGTCCTCAGTCTTGCAGC<br>CCAGAGCCCTCATTGCAGTATGCGGCCACCCAGCTGTACCC<br>TCCGCCCCCGTGGTCCCCCAGCTCCCCGCCTCACTCCACGG<br>GCTCGGTGAGGCCGGTCAGGGCACAGGGCGAGGGCCTCTTG<br>CCCTGAGCACCCTGGATGGTGACTGCGGATAGGGGCAGCCA<br>GACCAGCTCCCACAGGAGTTCAACTGGGTCTGAGACTTCAA<br>GGGGTGGTGGTGGGAGCCCCCCTTGGGAGAGGACCCCTGGG<br>AAGGGTGTTTTTCCTTTGAGGGGGATTCTGTGCCACAGGCA<br>GGCTCAGCTTCCTGCCTTCCATAGCTGTCATGGCCTCACCT<br>GGAGCGGAGGGGACCTGGGGACCTGAAGGTGGATGGGGACA<br>CAGCTCCTGGCTTCTCCTGGTGCTGCCCTCACTGTCCCCCC<br>GCCTAAAGGGGGTACTGAGCCTCCTGTGGCCCGCAGCAGTG<br>AGGGCACAGCTGTGGGTTGCAGGGGAGACAGCCAGCACGGC<br>GTGGCCATTCTATGACCCCCAGCCTGGCAGACTGGGGAGC<br>TGGGGGCAGAGGGCGGTGCCAAGTGCCACATCTTGCCATAG<br>TGGATGCTCTTCCAGTTTCTTTTTTCTATTAAACACCCCAC<br>TTCCTTTGG<br>NM_001172771.2 Homo sapiens interleukin<br>34 (IL34), transcript variant 2, mRNA |
| 46 | ATGATCAGAGATGTCTGCATGAGGAACAGAGGCTGCTTTGT<br>GGATTGGGGAGCTCCCCATTAGCGGAGGCAGAGCCAGATTT<br>CACACTGAGCAGCTGCAGTCGGAGAAATCAGAGAAAGCGTC<br>ACCCAGCCCCAGATTCCGAGGGGCCTGCCAGGGACTCTCTC<br>CTCCTGCTCCTTGGAAAGGAAGACCCCGAAAGACCCCCAAG<br>CCACCGGCTCAGACCTGCTTCTGGGCTGCCATGGGACTTGC<br>GGCCACCGCCCCCGGCTGTCCTCCACGCTGCCGGGCAGAT<br>AAGGGCAGCTGCTGCCCTTGGGGCACCTGCTCACTCCCGCA<br>GCCCAGCCACTCCTCCAGGGCCAGCCCTTCCCTGACTGAGT<br>GACCACCTCTGCTGCCCCGAGGCCATGTAGGCCGTGCTTAG<br>GCCTCTGTGGACACACTGCTGGGACGGCGCCTGAGCTCTC<br>AGGGGGACGAGGAACACCACCATGCCCCGGGGCTTCACCTG<br>GCTGCGCTATCTTGGGATCTTCCTTGGCGTGGCCTTGGGGA<br>ATGAGCCTTTGGAGATGTGGCCCTTGACGCAGAATGAGGAG<br>TGCACTGTCACGGGTTTTCTGCGGGACAAGCTGCAGTACAG<br>GAGCCGACTTCAGTACATGAAACACTACTTCCCCATCAACT<br>ACAAGATCAGTGTGCCTTACGAGGGGGTGTTCAGAATCGCC<br>AACGTCACCAGGCTGCAGAGGGCCAGGTGAGCGAGCGGGAGCT<br>GCGGTATCTGTGGGTCTTGGTGAGCCTCAGTGCCACTG<br>AGTCGGTGCAGGACGTGCTGCTCGAGGGCCACCCATCCTGG<br>AAGTACCTGCAGGAGGTGGAGACGCTGCTGCTGAATGTCCA<br>GCAGGGCCTCACGGATGTGGAGGTCAGCCCCAAGGTGGAAT<br>CCGTGTTGTCCCTCTTGAATGCCCCAGGGCCAAACCTGAAG<br>CTGGTGCGGCCCAAAGCCCTGCTGGACAACTGCTTCCGGGT<br>CATGGAGCTGCTGTACTGCTCCTGCTGTAAACAAAGCTCCG<br>TCCTAAACTGGCAGGACTGTGAGGTGCCAAGTCCTCAGTCT<br>TGCAGCCCAGAGCCCTCATTGCAGTATGCGGCCACCCAGCT<br>GTACCCTCCGCCCCCGTGGTCCCCCAGCTCCCCGCCTCACT<br>CCACGGGCTCGGTGAGGCCGGTCAGGGCACAGGGCGAGGGC<br>CTCTTGCCCTGAGCACCCTGGATGGTGACTGCGGATAGGGG<br>CAGCCAGACCAGCTCCCACAGGAGTTCAACTGGGTCTGAGA<br>CTTCAAGGGGTGGTGGTGGGAGCCCCCCTTGGGAGAGGACC<br>CCTGGGAAGGGTGTTTTTCCTTTGAGGGGGATTCTGTGCCA |
| | CAGCAGGGCTCAGCTTCCTGCCTTCCATAGCTGTCATGGCC<br>TCACCTGGAGCGGAGGGGACCTGGGGACCTGAAGGTGGATG<br>GGGACACAGCTCCTGGCTTCTCCTGGTGCTGCCCTCACTGT<br>CCCCCCGCCTAAAGGGGGTACTGAGCCTCCTGTGGCCCGCA<br>GCAGTGAGGGCACAGCTGTGGGTTGCAGGGGAGACAGCCAG<br>CACGGCGTGGCCATTCTATGACCCCCAGCCTGGCAGACTG<br>GGGAGCTGGGGCAGAGGGCGGTGCCAAGTGCCACATCTTG<br>CCATAGTGGATGCTCTTCCAGTTTCTTTTTTCTATTAAACA<br>CCCCACTTCCTTTGG<br>NM_001393493.1 Homo sapiens interleukin 34<br>(IL34), transcript variant 4, mRNA |
| 47 | ATGATCAGAGATGTCTGCATGAGGAACAGAGGCTGCTTTGT<br>GGATTGGGGAGCTCCCCATTAGCGGAGGCAGAGCCAGATTT<br>CACACTGAGCAGCTGCAGTCGGAGAAATCAGAGAAAGCGTC<br>ACCCAGCCCCAGATTCCGAGGGGCCTGCCAGGGACTCTCTC<br>CTCCTGCTCCTTGGAAAGGAAGACCCCGAAAGACCCCCAAG<br>CCACCGGCTCAGACCTGCTTCTGGGCTGCCATGGGACTTGC<br>GGCCACCGCCCCCGGCTGTCCTCCACGCTGCCGGGCAGAT<br>AAGGGCAGCTGCTGCCCTTGGGGCACCTGCTCACTCCCGCA<br>GCCCAGCCACTCCTCCAGGGCCAGCCCTTCCCTGACTGAGT<br>GACCACCTCTGCTGCCCCGAGGCCATGTAGGCCGTGCTTAG<br>GCCTCTGTGGACACACTGCTGGGACGGCGCCTGAGCTCTC<br>AGGGGGACGAGGAACACCACCATGCCCCGGGGCTTCACCTG<br>GCTGCGCTATCTTGGGATCTTCCTTGGCGTGGCCTTGGGA<br>ATGAGCCTTTGGAGATGTGGCCCTTGACGCAGAATGAGGAG<br>TGCACTGTCACGGGTTTTCTGCGGGACAAGCTGCAGTACAG<br>GAGCCGACTTCAGTACATGAAACACTACTTCCCCATCAACT<br>ACAAGATCAGTGTGCCTTACGAGGGGGTGTTCAGAATCGCC<br>AACGTCACCAGGCTGAGGGCCAGGTGAGCGAGCGGGAGCT<br>GCGGTATCTGTGGGTCTTGGTGAGCCTCAGTGCCACTGAGT<br>CGGTGCAGGACGTGCTGCTCGAGGGCCACCCATCCTGGAAG<br>TACCTGCAGGAGGTGGAGACGCTGCTGCTGAATGTCCAGCA<br>GGGCCTCACGGATGTGGAGGTCAGCCCCAAGGTGGAATCCG<br>TGTTGTCCCTCTTGAATGCCCCAGGGCCAAACCTGAAGCTG<br>GTGCGGCCCAAAGCCCTGCTGGACAACTGCTTCCGGGTCAT<br>GGAGCTGCTGTACTGCTCCTGCTGTAAACAAAGCTCCGTCC<br>TAAACTGGCAGGACTGTGAGGTGCCAAGTCCTCAGTCTTGC<br>AGCCCAGAGCCCTCATTGCAGTATGCGGCCACCCAGCTGTA<br>CCCTCCGCCCCCGTGGTCCCCCAGCTCCCCGCCTCACTCCA<br>CGGGCTCGGTGAGGCCGGTCAGGGCACAGGGCGAGGGCCTC<br>TTGCCCTGAGCACCCTGGATGGTGACTGCGGATAGGGGCAG<br>CCAGACCAGCTCCCACAGGAGTTCAACTGGGTCTGAGACTT<br>CAAGGGGTGGTGGTGGGAGCCCCCCTTGGGAGAGGACCCCT<br>GGGAAGGGTGTTTTTCCTTTGAGGGGGATTCTGTGCCACAG<br>CAGGGCTCAGCTTCCTGCCTTCCATAGCTGTCATGGCCTCA<br>CCTGGAGCGGAGGGGACCTGGGGACCTGAAGGTGGATGGGG<br>ACACAGCTCCTGGCTTCTCCTGGTGCTGCCCTCACTGTCCC<br>CCCGCCTAAAGGGGGTACTGAGCCTCCTGTGGCCCGCAGCA<br>GTGAGGGCACAGCTGTGGGTTGCAGGGGAGACAGCCAGCAC<br>GGCGTGGCCATTCTATGACCCCCAGCCTGGCAGACTGGGG<br>AGCTGGGGCAGAGGGCGGTGCCAAGTGCCACATCTTGGCCA<br>TAGTGGATGCTCTTCCAGTTTCTTTTTTCTATTAAACACCC<br>CACTTCCTTTGG<br>NM_001393495.1 Homo sapiens interleukin 34<br>(IL34), transcript variant 6, mRNA |
| 48 | CTCGAAGCTCGGCGTCTGTGATGGTCTACGGGCTTTCGAG<br>GTGATCAGGCAGCGTCAGTCTTCAGCCGCTAAGCCGAGAAG<br>GAGTCAGTCAGAGAGCTTGGGCCAGAGTTCCAGGGGCTCT<br>GGGAGTGGCTGCCAGAGCCAGATTTCACACTGAGCAGCTGC<br>AGTCGGAGAAATCAGAGAAAGCGTCACCCAGCCCCAGATTC<br>CGAGGGGCCTGCCAGGGACTCTCTCCTCCTGCTCCTTGGAA<br>AGGAAGACCCCGAAAGACCCCCAAGCCACCGGCTCAGACCT<br>GCTTCTGGGCTGCCATGGGACTTGCGGCCACCGCCCCCGG<br>CTGTCCTCCACGCTGCCGGGCAGATAAGGGCAGCTGCTGCC<br>CTTGGGGCACCTGCTCACTCCCGCAGCCCAGCCACTCCTCC<br>AGGGCCAGCCCTTCCCTGACTGAGTGACCACCTCTGCTGCC<br>CCGAGGCCATGTAGGCCGTGCTTAGGCCTCTGTGGACACAC<br>TGCTGGGACGGCGCCTGAGCTCTCAGGGGGACGAGGAACA<br>CCACCATGCCCCGGGGCTTCACCTGGCTGCGCTATCTTGGG<br>ATCTTCCTTGGCGTGGCCTTGGGGAATGAGCCTTTGGAGAT<br>GTGGCCCTTGACGCAGAATGAGGAGTGCACTGTCACGGGTT<br>TTCTGCGGGACAAGCTGCAGTACAGGAGCCGACTTCAGTAC<br>ATGAAACACTACTTCCCCATCAACTACAAGATCAGTGTGCC |

| SEQ ID NO | Sequence |
|---|---|
| | TTACGAGGGGGTGTTCAGAATCGCCAACGTCACCAGGCTGC AGAGGGCCCAGGTGAGCGAGCGGGAGCTGCGGTATCTGTGG GTCTTGGTGAGCCTCAGTGCCACTGAGTCGGTGCAGGACGT GCTGCTCGAGGGCCACCCATCCTGGAAGTACCTGCAGGAGG TGGAGACGTGCTGCTGAATGTCCAGCAGGGCCTCACGGAT GTGGAGGTCAGCCCCAAGGTGGAATCCGTGTTGTCCCTCTT GAATGCCCCAGGGCCAAACCTGAAGCTGGTGCGGCCCAAAG CCCTGCTGGACAACTGCTTCCGGGTCATGGAGCTGCTGTAC TGCTCCTGCTGTAAACAAAGCTCCGTCCTAAACTGGCAGGA CTGTGAGGTGCCAAGTCCTCAGTCTTGCAGCCCAGAGCCCT CATTGCAGTATGCGGCCACCCAGCTGTACCCTCCGCCCCCG TGGTCCCCAGCTCCCCGCCTCACTCCACGGGCTCGGTGAGG GCCGGTCAGGGCACAGGGCGAGGGCCTCTTGCCCTGAGCAC CCTGGATGGTGACTGCGATAGGGGCAGCCAGACCAGCTCC CACAGGAGTTCAACTGGGTCTGAGACTTCAAGGGGTGGTGG TGGGAGCCCCCTTGGGAGAGGACCCCTGGGAAGGGTGTTT TTCCTTTGAGGGGGATTCTGTGCCACAGCAGGGCTCAGCTT CCTGCCTTCCATAGCTGTCATGGCCTCACCTGGAGCGGAGG GGACCTGGGGACCTGAAGGTGGATGGGGACACAGCTCCTGG CTTCTCCTGGTGCTGCCCTCACTGTCCCCCCGCCTAAAGGG GGTACTGAGCCTCCTGTGGCCCGCAGCAGTGAGGGCACAGC TGTGGGTTGCAGGGGAGACAGCCAGCACGGCGTGGCCATTC TATGACCCCCAGCCTGGCAGACTGGGGAGCTGGGGCAGA GGGCGGTGCCAAGTGCCACATCTTGCCATAGTGGATGCTCT TCCAGTTTCTTTTTTCTATTAAACACCCCACTTCCTTTGG NM_001172772.2 *Homo sapiens* interleukin 34 (IL34), transcript variant 3, mRNA |
| 49 | ACACTGAGCAGCTGCAGTCGGAGAAATCAGAGAAAGCGTCA CCCAGCCCCAGATTCCGAGGGGCCTGCCAGGGACTCTCTCC TCCTGCTCCTTGGAAAGGAAGACCCCGAAAGACCCCCAAGC CACCGGCTCAGACCTGCTTCTGGGCTGCCATGGGACTTGCG GCCACCGCCCCCGGCTGTCCTCCACGCTGCCGGGCAGATA AGGGCAGCTGCTGCCCTTGGGCACCTGCTCACTCCCGCAG CCCAGCCACTCCTCCAGGGCCAGCCCTTCCTGACTGAGTG ACCACCTCTGCTGCCCCGAGGCCATGTAGGCCGTGCTTAGG CCTCTGTGGACACACTGCTGGGACGGCGCCTGAGCTCTCA GGGGGACGAGGAACACCACCATGCCCGGGGCTTCACCTGG CTGCGCTATCTTGGGATCTTCCTTGGCGTGGCCTTGGGGAA TGAGCCTTTGGAGATGTGGCCCTTGACGCAGAATGAGGAGT GCACTGTCACGGGTTTTCTGCGGGACAAGCTGCAGTACAGG AGCCGACTTCAGTACATGAAACACTACTTCCCCATCAACTA CAAGATCAGTGTGCCTTACGAGGGGGTGTTCAGAATCGCCA ACGTCACCAGGCTGCAGAGGGCCCAGGTGAGCGAGCGGGAG CTGCGGTATCTGTGGGTCTTGGTGAGCCTCAGTGCCACTGA GTCGGTGCAGGACGTGCTGCTCGAGGGCCACCCATCCTGGA AGTACCTGCAGGAGGTGGAGACGCTGCTGCTGAATGTCCAG CAGGGCCTCACGGATGTGGAGGTCAGCCCCAAGGTGGAATC CGTGTTGTCCCTCTTGAATGCCCCAGGGCCAAACCTGAAGC TGGTGCGGCCCAAAGCCCTGCTGGACAACTGCTTCCGGGTC ATGGAGCTGCTGTACTGCTCCTGCTGTAAACAAAGCTCCGT CCTAAACTGGCAGGACTGTGAGGTGCCAAGTCCTCAGTCTT GCAGCCCAGAGCCCTCATTGCAGTATGCGGCCACCCAGCTG TACCCTCCGCCCCCGTGGTCCCCAGCTCCCCGCCTCACTC CACGGGCTCGGTGAGGGCCGGTCAGGGCACAGGGCGAGGGC TCTTGCCCTGAGCACCCTGGATGGTGACTGCGATAGGGGC AGCCAGACCAGCTCCCACAGGAGTTCAACTGGGTCTGAGAC TTCAAGGGGTGGTGGTGGGAGCCCCCTTGGGAGAGGACCC CTGGGAAGGGTGTTTTCCTTTGAGGGGGATTCTGTGCCAC AGCAGGGCTCAGCTTCCTGCCTTCCATAGCTGTCATGGCCT CACCTGGAGCGGAGGGGACCTGGGGACCTGAAGGTGGATGG GGACACAGCTCCTGGCTTCTCCTGGTGCTGCCCTCACTGTC CCCCCGCCTAAAGGGGGTACTGAGCCTCCTGTGGCCCGCAG CAGTGAGGGCACAGCTGTGGGTTGCAGGGGAGACAGCCAGC ACGGCGTGGCCATTCTATGACCCCCAGCCTGGCAGACTGGG GAGCTGGGGCAGAGGGCGGTGCCAAGTGCCACATCTTGC CATAGTGGATGCTCTTCCAGTTTCTTTTTTCTATTAAACAC CCCACTTCCTTTGG NM_001393494.1 *Homo sapiens* interleukin 34 (IL34), transcript variant 5, mRNA |
| 50 | ACACTGAGCAGCTGCAGTCGGAGAAATCAGAGAAAGCGTCA CCCAGCCCCAGATTCCGAGGGGCCTGCCAGGGACTCTCTCC TCCTGCTCCTTGGAAAGGAAGACCCCGAAAGACCCCCAAGC CACCGGCTCAGACCTGCTTCTGGGCTGCCATGGGACTTGCG GCCACCGCCCCCGGCTGTCCTCCACGCTGCCGGGCAGATA AGGGCAGCTGCTGCCCTTGGGCACCTGCTCACTCCCGCAG CCCAGCCACTCCTCCAGGGCCAGCCCTTCCTGACTGAGTG ACCACCTCTGCTGCCCCGAGGCCATGTAGGCCGTGCTTAGG CCTCTGTGGACACACTGCTGGGACGGCGCCTGAGCTCTCA GGGGGACGAGGAACACCACCATGCCCGGGGCTTCACCTGG CTGCGCTATCTTGGGATCTTCCTTGGCGTGGCCTTGGGGAA TGAGCCTTTGGAGATGTGGCCCTTGACGCAGAATGAGGAGT GCACTGTCACGGGTTTTCTGCGGGACAAGCTGCAGTACAGG AGCCGACTTCAGTACATGAAACACTACTTCCCCATCAACTA CAAGATCAGTGTGCCTTACGAGGGGGTGTTCAGAATCGCCA ACGTCACCAGGCTGAGGGCCCAGGTGAGCGAGCGGGAGCTG CGGTATCTGTGGGTCTTGGTGAGCCTCAGTGCCACTGAGTC GGTGCAGGACGTGCTGCTCGAGGGCCACCCATCCTGGAAGT ACCTGCAGGAGGTGGAGACGCTGCTGCTGAATGTCCAGCAG GGCCTCACGGATGTGGAGGTCAGCCCCAAGGTGGAATCCGT GTTGTCCCTCTTGAATGCCCCAGGGCCAAACCTGAAGCTGG TGCGGCCCAAAGCCCTGCTGGACAACTGCTTCCGGGTCATG GAGCTGCTGTACTGCTCCTGCTGTAAACAAAGCTCCGTCCT AAACTGGCAGGACTGTGAGGTGCCAAGTCCTCAGTCTTGCA GCCCAGAGCCCTCATTGCAGTATGCGGCCACCCAGCTGTAC CCTCCGCCCCCAGCTCCCCGCCTCACTCCAC GGGCTCGGTGAGGCCGGTCAGGGCACAGGGCGAGGGCCTCT TGCCCTGAGCACCCTGGATGGTGACTGCGATAGGGGCAGC CAGACCAGCTCCCACAGGAGTTCAACTGGGTCTGAGACTTC AAGGGGTGGTGGTGGGAGCCCCCTTGGGAGAGGACCCTGG GGAAGGGTGTTTTTCCTTTGAGGGGGATTCTGTGCCACAGC AGGGCTCAGCTTCCTGCCTTCCATAGCTGTCATGGCCTCAC CTGGAGCGGAGGGGACCTGGGGACCTGAAGGTGGATGGGGA CACAGCTCCTGGCTTCTCCTGGTGCTGCCCTCACTGTCCCC CGCCTAAAGGGGTACTGAGCCTCCTGTGGCCCGCAGCAGT GAGGGCACAGCTGTGGGTTGCAGGGGAGACAGCCAGCACG GCGTGGCCATTCTATGACCCCCAGCCTGGCAGACTGGGGA GCTGGGGCAGAGGGCGGTGCCAAGTGCCACATCTTGCCAT AGTGGATGCTCTTCCAGTTTCTTTTTTCTATTAAACACCCC ACTTCCTTTGG NM_001393496.1 *Homo sapiens* interleukin 34 (IL34), transcript variant 7, mRNA |
| 51 | GGAAGGCGCTACAGACCCGCTGGCATAGTTAGCTGGGAGGG ACACTAAGATCAGATAGAGCAGGAAGGAAAGTGGTGTGGGG CGTGGGTGACTGAAGAGTCATTTTATCAAGTTGAAACCAGA ATCCAGGATGATTCGATCTCCTGAATGCCGGGCTGGAAAAC CCAGCAACGAGCTTTGAAAACATATCACCCGGACACCAGGG GCAGAGGCTGTTCTGGGCGGGAGGTTGTGCCTGCCCCACGG AGCGACAGAAGCGGGGAGACCAGACGTCGACCCTGAGGCGT GCCTCCTGGGGGCTCCAGTGGCCGGCATGGGATCTTGGGA TCTTCCTTGGCGTGGCCTTGGGGAATGAGCCTTTGGAGATG TGGCCCTTGACGCAGAATGAGGAGTGCACTGTCACGGGTTT TCTGCGGGACAAGCTGCAGTACAGGAGCCGACTTCAGTACA TGAAACACTACTTCCCCATCAACTACAAGATCAGTGTGCCT TACGAGGGGGTGTTCAGAATCGCCAACGTCACCAGGCTGCA GAGGGCCCAGGTGAGCGAGCGGGAGCTGCGGTATCTGTGGG TCTTGGTGAGCCTCAGTGCCACTGAGTCGGTGCAGGACGTG CTGCTCGAGGGCCACCCATCCTGGAAGTACCTGCAGGAGGT GGAGACGCTGCTGCTGAATGTCCAGCAGGGCCTCACGGATG TGGAGGTCAGCCCCAAGGTGGAATCCGTGTTGTCCCTCTTG AATGCCCCAGGGCCAAACCTGAAGCTGGTGCGGCCCAAAGC CCTGCTGGACAACTGCTTCCGGGTCATGGAGCTGCTGTACT GCTCCTGCTGTAAACAAAGCTCCGTCCTAAACTGGCAGGAC TGTGAGGTGCCAAGTCCTCAGTCTTGCAGCCCAGAGCCCTC ATTGCAGTATGCGGCCACCCAGCTGTACCCTCCGCCCCCGT GGTCCCCAGCTCCCCGCCTCACTCCACGGGCTCGGTGAGG CCGGTCAGGGCACAGGGCGAGGGCCTCTTGCCCTGAGCACC CTGGATGGTGACTGCGATAGGGGCAGCCAGACCAGCTCCC ACAGGAGTTCAACTGGGTCTGAGACTTCAAGGGGTGGTGGT GGGAGCCCCCTTGGGAGAGGACCCTGGGAAGGGTGTTTT TCCTTTGAGGGGGATTCTGTGCCACAGCAGGGCTCAGCTTC CTGCCTTCCATAGCTGTCATGGCCTCACCTGGAGCGGAGGG GACCTGGGGACCTGAAGGTGGATGGGGACACAGCTCCTGGC TTCTCCTGGTGCTGCCCTCACTGTCCCCCGCCTAAAGGGG GTACTGAGCCTCCTGTGGCCCGCAGCAGTGAGGGCACAGCT GTGGGTTGCAGGGGAGACAGCCAGCACGGCGTGGCCATTCT ATGACCCCCAGCCTGGCAGACTGGGGAGCTGGGGGCAGAG |

| SEQ ID NO | Sequence |
|---|---|
| | GGCGGTGCCAAGTGCCACATCTTGCCATAGTGGATGCTCTT<br>CCAGTTTCTTTTTTCTATTAAACACCCCACTTCCTTTGG<br>NM_001393497.1 Homo sapiens interleukin 34<br>(IL34), transcript variant 8, mRNA |
| 52 | GGAAGGCGCTACAGACCCGCTGGCATAGTTAGCTGGGAGGG<br>ACACTAAGATCAGATAGAGCAGGAAGGAAAGTGGTGTGGGG<br>CGTGGGTGACTGAAGAGTCATTTTATCAAGTTGAAACCAGA<br>ATCCAGGATGATTCGATCTCCTGAATGCCGGGCTGGAAAAC<br>CCAGCAACGAGCTTTGAAAACATATCACCCGGACACCAGGG<br>GCAGAGGCTGTTCTGGGCGGGAGGTTGTGCCTGCCCCACGG<br>AGCGACAGAAGCGGGGAGACCAGACGTCGACCCTGAGGCGT<br>GCCTCCTGGGGGCTCCAGTGGCCGGCATGGGATCTTGGGA<br>TCTTCCTTGGCGTGGCCTTGGGGAATGAGCCTTTGGAGATG<br>TGGCCCTTGACGCAGAATGAGGAGTGCACTGTCACGGGTTT<br>TCTGCGGGACAAGCTGCAGTACAGGAGCCGACTTCAGTACA<br>TGAAACACTACTTCCCCATCAACTACAAGATCAGTGTGCCT<br>TACGAGGGGTGTTCAGAATCGCCAACGTCACCAGGCTGAG<br>GGCCCAGGTGAGCGAGCGGGAGCTGCGGTATCTGTGGGTCT<br>TGGTGAGCCTCAGTGCCACTGAGTCGGTGCAGGACGTGCTG<br>CTCGAGGGCCACCCATCCTGGAAGTACCTGCAGGAGGTGGA<br>GACGCTGCTGCTGAATGTCCAGCAGGGCCTCACGGATGTGG<br>AGGTCAGCCCCAAGGTGGAATCCGTGTTGTCCCTCTTGAAT |

| SEQ ID NO | Sequence |
|---|---|
| | GCCCCAGGGCCAAACCTGAAGCTGGTGCGGCCCAAAGCCCT<br>GCTGGACAACTGCTTCCGGGTCATGGAGCTGCTGTACTGCT<br>CCTGCTGTAAACAAAGCTCCGTCCTAAACTGGCAGGACTGT<br>GAGGTGCCAAGTCCTCAGTCTTGCAGCCCAGAGCCCTCATT<br>GCAGTATGCGGCCACCCAGCTGTACCCTCCGCCCCCGTGGT<br>CCCCCAGCTCCCCGCCTCACTCCACGGGTCGGTGAGGCCG<br>GTCAGGGCACAGGGCGAGGGCCTCTTGCCCTGAGCACCCTG<br>GATGGTGACTGCGGATAGGGGCAGCCAGACCAGCTCCCACA<br>GGAGTTCAACTGGGTCTGAGACTTCAAGGGGTGGTGGTGGG<br>AGCCCCCCTTGGGAGAGGACCCCTGGGAAGGGTGTTTTTCC<br>TTTGAGGGGATTCTGTGCCACAGCAGGGCTCAGCTTCCTG<br>CCTTCCATAGCTGTCATGGCCTCACCTGGAGCGGAGGGGAC<br>CTGGGGACCTGAAGGTGGATGGGGACACAGCTCCTGGCTTC<br>TCCTGGTGCTGCCCTCACTGTCCCCCCGCCTAAAGGGGGTA<br>CTGAGCCTCCTGTGGCCCGCAGCAGTGAGGGCACAGCTGTG<br>GGTTGCAGGGGAGACAGCCAGCACGGCGTGGCCATTCTATG<br>ACCCCCCAGCCTGGCAGACTGGGGAGCTGGGGGCAGAGGGC<br>GGTGCCAAGTGCCACATCTTGCCATAGTGGATGCTCTTCCA<br>GTTTCTTTTTTCTATTAAACACCCCACTTCCTTTGG<br>NM_001393498.1 Homo sapiens interleukin<br>34 (IL34), transcript variant 9, mRNA |

The invention claimed is:

1. A polynucleotide that is complementary to IL-34 comprising a nucleotide sequence selected from the group consisting of:
   a. 5'-CxTxTxTxGGGCXGCACCAGCxTxTxCx-3' (SEQ ID NO: 40), wherein Cx is 2'-O-(2-methoxyethyl)cytidine, Tx is 2'-O-(2-methoxyethyl)thymidine, and X is 5-methylcytidine;
   b. 5'-CxTxTxTGGGCXGCACCAGCTXTxCx-3' (SEQ ID NO: 41), wherein Cx is 2'-O-(2-methoxyethyl)cytidine, Tx is 2'-O-(2-methoxyethyl)thymidine, and X is 5-methylcytidine;
   c. 5'-TxCxCxAxTGACCXGGAAGCAxGxTxTx-3' (SEQ ID NO: 42), wherein Cx is 2'-O-(2-methoxyethyl)cytidine, Ax is 2'-O-(2-methoxyethyl)adenosine, Tx is 2'-O-(2-methoxyethyl)thymidine, Gx is 2'-O-(2-methoxyethyl)guanosine, and X is 5-methylcytidine; or
   d. 5'-TxCxCxATGACCXGGAAGCAGxTxTx-3' (SEQ ID NO: 43), wherein Cx is 2'-O-(2-methoxyethyl)cytidine, Tx is 2'-O-(2-methoxyethyl)thymidine, Gx is 2'-O-(2-methoxyethyl)guanosine, and X is 5-methylcytidine;
   or a pharmaceutically acceptable salt thereof.

2. The polynucleotide of claim 1, wherein the polynucleotide is an IL-34 antisense oligonucleotide.

3. The polynucleotide of claim 1, wherein the polynucleotide is part of an IL-34 siRNA complex.

4. The polynucleotide of claim 1, wherein at least one internucleoside linkage of the polynucleotide is selected from the group consisting of a phosphorothioate linkage, a phosphorodithioate linkage, a phosphotriester linkage, an alkylphosphonate linkage, an aminoalkylphosphotriester linkage, an alkylene phosphonate linkage, a phosphinate linkage, a phosphoramidate linkage, and an aminoalkylphosphoramidate linkage, a thiophosphoramidate linkage, thionoalkylphosphonate linkage, a thionoalkylphosphotriester linkage, a thiophosphate linkage, a selenophosphate linkage, and a boranophosphate linkage.

5. A pharmaceutical composition, comprising (a) a polynucleotide of claim 1, or a pharmaceutically acceptable salt thereof, and (b) a pharmaceutically acceptable excipient.

6. A method of treating an inflammatory bowel disease in a patient in need thereof, the method comprising administering to the patient in need thereof an effective amount of a polynucleotide of claim 1, or a pharmaceutically acceptable salt thereof, or a pharmaceutical composition of claim 5.

7. A method of reducing or eliminating a fibrotic stricture in a patient suffering from an inflammatory bowel disease, the method comprising administering an effective amount of a polynucleotide of claim 1, or a pharmaceutically acceptable salt thereof.

8. The method of claim 7, wherein the fibrotic stricture is located in the intestine.

9. The method of claim 7, wherein the inflammatory bowel disease is inflammatory Crohn's disease or fibrostricturing Crohn's disease.

10. The method of claim 6, wherein the polynucleotide is administered intraarticularly, rectally, topically, parenterally, orally, pulmonarily, intratracheally, intranasally, transdermally, or intraduodenally.

11. The method of claim 6, wherein the patient is a human.

* * * * *